(12) United States Patent
Porteus

(10) Patent No.: US 12,129,471 B2
(45) Date of Patent: Oct. 29, 2024

(54) MATERIALS AND METHODS FOR TREATMENT OF HUMAN GENETIC DISEASES INCLUDING HEMOGLOBINOPATHIES

(71) Applicant: Vertex Pharmaceuticals Incorporated, Boston, MA (US)

(72) Inventor: Matthew Hebden Porteus, Stanford, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 15/550,954

(22) PCT Filed: Feb. 23, 2016

(86) PCT No.: PCT/IB2016/000286
§ 371 (c)(1),
(2) Date: Aug. 14, 2017

(87) PCT Pub. No.: WO2016/135559
PCT Pub. Date: Sep. 1, 2016

(65) Prior Publication Data
US 2018/0200387 A1    Jul. 19, 2018

Related U.S. Application Data

(60) Provisional application No. 62/119,774, filed on Feb. 23, 2015.

(51) Int. Cl.
| | | |
|---|---|---|
| *C12N 15/63* | (2006.01) | |
| *A61K 48/00* | (2006.01) | |
| *A61P 7/06* | (2006.01) | |
| *C12N 15/09* | (2006.01) | |
| *C12N 15/113* | (2010.01) | |

(52) U.S. Cl.
CPC ............ *C12N 15/63* (2013.01); *A61K 48/005* (2013.01); *A61P 7/06* (2018.01); *C12N 15/09* (2013.01); *C12N 15/113* (2013.01); *C12N 2310/10* (2013.01); *C12N 2310/20* (2017.05); *C12N 2320/11* (2013.01)

(58) Field of Classification Search
CPC ..... C12N 15/09; C12N 15/63; C12N 2320/11
See application file for complete search history.

(56) References Cited

U.S. PATENT DOCUMENTS

| | | | |
|---|---|---|---|
| 9,738,693 B2 | 8/2017 | Telford et al. | |
| 9,840,538 B2 | 12/2017 | Telford et al. | |
| 10,738,305 B2 | 8/2020 | Porteus | |
| 11,268,077 B2 | 3/2022 | Chakraborty et al. | |
| 2014/0093913 A1* | 4/2014 | Cost ................... | C07K 14/4702 435/69.1 |
| 2015/0044772 A1 | 2/2015 | Zhao et al. | |
| 2015/0152436 A1 | 6/2015 | Musunuru et al. | |
| 2015/0166969 A1 | 6/2015 | Takeuchi et al. | |
| 2016/0289675 A1 | 10/2016 | Ryan et al. | |
| 2018/0021413 A1 | 1/2018 | Porteus | |
| 2018/0030438 A1 | 2/2018 | Porteus et al. | |
| 2018/0094033 A1 | 4/2018 | Telford et al. | |
| 2018/0112213 A1 | 4/2018 | Welstead et al. | |
| 2018/0119140 A1 | 5/2018 | Porteus et al. | |
| 2018/0179521 A1 | 6/2018 | Rahdar et al. | |
| 2018/0273609 A1 | 9/2018 | Porteus | |
| 2019/0256829 A1 | 8/2019 | Chakraborty et al. | |
| 2021/0009998 A1 | 1/2021 | Porteus | |
| 2021/0180091 A1 | 6/2021 | Chakraborty et al. | |
| 2021/0317450 A9 | 10/2021 | Porteus | |
| 2022/0259578 A1 | 8/2022 | Chakraborty et al. | |

FOREIGN PATENT DOCUMENTS

| | | |
|---|---|---|
| CN | 104284669 A | 1/2015 |
| EP | 3262172 A2 | 9/2016 |
| WO | WO 2013/126794 A1 | 8/2013 |
| WO | WO 2013/169398 A2 | 11/2013 |
| WO | WO 2013/176772 A1 | 11/2013 |
| WO | WO 2014/036219 A2 | 3/2014 |
| WO | WO 2015/183026 A1 | 5/2014 |
| WO | WO 2014/085593 A1 | 6/2014 |
| WO | WO 2014/093712 A1 | 6/2014 |
| WO | WO 2014/186585 A2 | 11/2014 |
| WO | WO 2014/197748 A2 | 12/2014 |
| WO | WO 2015/006498 A2 | 1/2015 |
| WO | WO 2015/006747 A2 | 1/2015 |

(Continued)

OTHER PUBLICATIONS

Printout from en.wikipedia.org/wiki/Endonuclease. Printed Aug. 9, 2019. pp. 1-6 (Year: 2019).*
Maeder and Gersbach. Molecular Therapy 24(3):430-446, 2016. (Year: 2016).*
Howden (printout from cosmosmagazine.com/biology/crispr-gene-editing...2017. pp. 1-4 (Year: 2017).*
Printout from en.wikipedia.org/wiki/Endonuclease; pp. 1/1-1/6, printed Jun. 3, 2021 (Year: 2021).*
International Search Report and Written Opinion mailed Jul. 2, 2019 for International Application No. PCT/IB2019/000183.

(Continued)

*Primary Examiner* — Marcia S Noble
(74) *Attorney, Agent, or Firm* — McNeill Baur PLLC

(57) ABSTRACT

The present application provides materials and methods for treating hemoglobinopathies. More specifically, the application provides methods for producing progenitor cells that are genetically modified via genome editing to increase the production of fetal hemoglobin (HbF), as well as modified progenitor cells (including, for example, CD34+ human hematopoietic stem cells) producing increased levels of HbF, and methods of using such cells for treating hemoglobinopathies such as sickle cell anemia and β-thalassemia.

14 Claims, 26 Drawing Sheets

Specification includes a Sequence Listing.

(56) References Cited

FOREIGN PATENT DOCUMENTS

| | | | |
|---|---|---|---|
| WO | WO 2015/026885 A1 | 2/2015 |
| WO | WO 2015/113063 A1 | 7/2015 |
| WO | WO 2015/148863 A2 | 10/2015 |
| WO | WO 2016/135557 A2 | 9/2016 |
| WO | WO 2016/135558 A2 | 9/2016 |
| WO | WO 2016/135559 A2 | 9/2016 |
| WO | WO 2017/077394 A2 | 5/2017 |
| WO | WO 2017/115268 A1 | 7/2017 |
| WO | WO 2017/160890 A1 | 9/2017 |
| WO | WO 2017/182881 A2 | 10/2017 |
| WO | WO 2017/191503 A1 | 11/2017 |
| WO | WO 2018/081470 A1 | 5/2018 |
| WO | WO 2019/081982 A1 | 5/2019 |

OTHER PUBLICATIONS

Hendel et al., Chemically modified guide RNAs enhance CRISPR-Cas genome editing in human primary cells. Nat Biotechnol. Sep. 2015;33(9):985-89. Author manuscript provided. Available in PMC Sep. 1, 2016, 14 pages. doi: 10.1038/nbt.3290.
Urnov et al., Genome editing with engineered zinc finger nucleases. Nat Rev Genet. Sep. 2010;11:636-46. doi: 10.1038/nrg2842.
Ye et al., Genome editing using CRISPR-Cas9 to create the HPFH genotype in HSPCs: An approach for treating sickle cell disease and β-thalassemia. Proc Natl Acad Sci U S A. Sep. 20, 2016;113(38):10661-5. doi: 10.1073/pnas.1612075113. Epub Sep. 6, 2016.
De Montalembert, Management of Sickle Cell Disease. BMJ. Sep. 8, 2008;337:a1397. doi: 10.1136/bmj.a1397.
Dipersio et al., Plerixafor and G-CSF versus placebo and G-CSF to mobilixe hematopoietic stem cells for autologous stem cell transplantation in patients with multiple myeloma. Blood. Jun. 4, 2009;113(23):5720-6.
Sheth et al., Sickle cell disease: time for a closer look at treatment options? BJH. Aug. 2013;162(4):455-64.
Sun et al., Seamless correction of the sickle cell disease mutation of the HBB gene in human induced pluripotent stem cells using TALENs. Biotechnol Bioeng. May 2014;111(5):1048-53. doi: 10.1002/bit.25018. Epub Aug. 26, 2013.
Thein et al., Control of fetal hemoglobin: new insights emerging from genomics and clinical implications. Hum Mol Genet. Oct. 15, 2009;18(R2):R216-23. doi: 10.1093/hmg/ddp401.
Tuan et al., Different 3' end points of deletions causing delta beta-thalassemia and hereditary persistence of fetal hemoglobin: implications for the control of gamma-globin gene expression in man. Proc Natl Acad Sci U S A. Nov. 1983;80(22):6937-41. doi: 10.1073/pnas.80.22.6937.
Huisman et al., A Syllabus of Thalassemia Mutations. Published by the Sickle Cell Anemia Foundation. 1997. https://globin.bx.psu.edu/html/huisman/thals/ [last accessed Oct. 19, 2021].
Zhang et al., Optimization of genome editing through CRISPR-Cas9 engineering. Bioengineered. Apr. 2016;7(3):166-74. doi: 10.1080/21655979.2016.1189039.
Huang et al., "Production of Gene-Corrected Adult Beta Globin Protein in Human Erythrocytes Differentiated from Patient iPSCs After Genome Editing of the Sickle Point Mutation", Stem Cells, May 2015, vol. 33, Issue 5, pp. 1470-1479.
Huang et al., Abstract: "Production of Gene-Corrected Adult Beta Globin Protein in Human Erythrocytes Differentiated from Patient iPSCs After Genome Editing of the Sickle Point Mutation", Stem Cells, May 2015, vol. 33, Issue 5, 3 pages.
Saglio et al., "Italian Type of Deletional Hereditary Persistence of Fetal Hemoglobin", Blood, Sep. 1986, vol. 68, No. 3, pp. 646-651.
Sebastiano et al., "In Situ Genetic Correction of the Sickle Cell Anemia Mutation in Human Induced Pluripotent Stem Cells Using Engineered Zinc Finger Nucleases", Stem Cells, 2011, vol. 29, pp. 1717-1726.
International Search Report for International Application No. PCT/IB2016/000286 dated Sep. 7, 2016.
Written Opinion of the International Searching Authority for International Application No. PCT/IB2016/000286 dated Sep. 7, 2016.

International Preliminary Report on Patentability mailed on Sep. 8, 2017 for International Application No. PCT/IB2016/000276.
International Search Report and Written Opinion mailed on Sep. 7, 2016 for International Application No. PCT/IB2016/000282.
International Preliminary Report on Patentability mailed on Sep. 8, 2017 for International Application No. PCT/IB2016/000282.
International Search Report and Written Opinion mailed on Oct. 20, 2017 for International Application No. PCT/IB2017/000532.
International Preliminart Report on Patentability mailed Nov. 15, 2018 for International Application No. PCT/IB2017/000532.
International Search Report and Written Opinion mailed Apr. 15, 2019 for International Application No. PCT/IB2018/001338.
International Search Report and Written Opinion mailed May 11, 2017 for International Application No. PCT/IB2016/001750.
International Preliminary Report on Patentability mailed May 17, 2018 for International Application No. PCT/IB2016/001750.
International Search Report and Written Opinion mailed Sep. 7, 2016 for International Application No. PCT/IB2016/000286.
[No Author Listed] Opinion—520 F.3d 1353. *Eisai Co. Ltd.* V. *Dr. Reddy's*. Before the United States Court of Appeals, Federal Circuit. Sep. 16, 2008: 13 pages. Last accessed Jul. 29, 2023.
[No Author Listed] Opinion—520 F.3d 1358. *Ortho-Mcneil* v. *Mylan Lab*. Before the United States Court of Appeals, Federal Circuit. Mar. 31, 2008: 14 pages. Last accessed Jul. 29, 2023.
[No Author Listed] GENESEQ Submission; GSN, Database Accession No. GS_NUC_ALERT:WO2016161380.324727. Oct. 6, 2016.
Camaschella et al., A New Hereditary Persistence of Fetal Hemoglobin Deletion Has the Breakpoint Within the 3' β-Globin Gene Enhancer.Blood. 1990;75(4):1000-1005.
Canver et al., BCL11A enhancer dissection by Cas9-mediated in situ saturating mutagenesis. Nature. Nov. 12, 2015;527(7577):192-7.
Canver et al., Customizing the genome as therapy for the beta-hemoglobinopathies. Blood. Apr. 6, 2016;127(21):2536-45.
Chakalova et al., The Corfu deltabeta thalassemia deletion disrupts gamma-globin gene silencing and reveals post-transcriptional regulation of HbF expression. Blood. Mar. 1, 2005;105(5):2154-60. doi: 10.1182/blood-2003-11-4069. Epub Nov. 9, 2004.
Chandrakasan et al., Gene Therapy for Hemoglobinopathies: The State of the Field and the Future. Hematol Oncol Clin North Am. Apr. 2014;28(2):1-23.
Cottle et al., Controlled delivery of beta-globin-targeting TALENs and CRISPR/Cas9 into mammalian cells for genome editing using microinjection. Sci Rep. Nov. 12, 2015;5:16031,13pages.
Cradick et al., CRISPR/Cas9 systems targeting β-globin and CCR5 genes have substantial off-target activity.Nucleic Acids Research. 2013;41(20):9584-9592.
Dever et al., CRISPR/Cas9 beta-globin gene targeting in human haematopoietic stem cells. Nature. Nov. 17, 2016;539(7629):384-389.
Henthorn et al., (A gamma delta beta)0-Thalassaemia in Blacks is due to a deletion of 34 kbp of DNA.British Journal of Haematology. 1985;59(2):343-356.
Hsu et al., Development and applications of CRISPR-Cas9 for genome engineering. Cell. Jun. 5, 2014;157(6):1262-78.
Huang et al., Abstract:Production of Gene-Corrected Adult Beta Globin Protein in Human Erythrocytes Differentiated from Patient iPSCs After Genome Editing of the Sickle Point Mutation.Stem Cells.2015;33(5):3.
Huang et al., Production of Gene-Corrected Adult Beta Globin Protein in Human Erythrocytes Differentiated from Patient iPSCs After Genome Editing of the Sickle Point Mutation. Stem Cells. May 2015;33(5):1470-9. doi: 10.1002/stem.1969.
Joly et al., Identification and molecular characterization of four new large deletions in the β-globin gene cluster.Blood Cells, Molecules, and Diseases.2009;43:53-57.
Kim et al., Highly efficient RNA-guided genome editing in human cells via delivery of purified Cas9 ribonucleoproteins. Genome research. Jun. 1, 2014;24(6):1012-9.
Mansilla-Soto et al., Cell and Gene Therapy for the Beta-Thalassemias: Advances and Prospects. Hum Gene Ther. Apr. 2016;27(4):295-304.

(56) References Cited

OTHER PUBLICATIONS

Roosjen et al., Transcriptional regulators Myb and BCL11A interplay with DNA methyltransferase 1 in developmental silencing of embryonic and fetal β-like globin genes. FASEB J. Apr. 2014;28(4):1610-20. Epub Dec. 26, 2013.

Saglio et al., Italian Type of Deletional Hereditary Persistence of Fetal Hemoglobin.Blood. 1986;686(3):646-651.

Sankaran et al., A functional element necessary for fetal hemoglobin silencing. N Engl J Med. Sep. 1, 2011;365(9):807-14. doi: 10.1056/NEJMoa1103070.

Sebastiano et al., In Situ Genetic Correction of the Sickle Cell Anemia Mutation in Human Induced Pluripotent Stem Cells Using Engineered Zinc Finger Nucleases.Stem Cells.2011;29:1717-1726.

Song et al., Improved hematopoietic differentiation efficiency of gene-corrected beta-thalassemia induced pluripotent stem cells by CRISPR/Cas9 system. Stem Cells Dev. May 1, 2015;24(9):1053-65. doi: 10.1089/scd.2014.0347. Epub Feb. 5, 2015.

Suzuki et al., Fetal globin gene repressors as drug targets for molecular therapies to treat the β-globinopathies. Mol Cell Biol. Oct. 1, 2014;34(19):3560-9. Epub Jul. 14, 2014.

Townes et al., Modified IPS Cells for Hemoglobinopathies. Blood. Dec. 2015;126(23):SCI-17.

Traxler et al., Genome Editing Recreates Hereditary Persistence of Fetal Hemoglobin in Primary Human Erythroblasts. Dec. 3, 2015;126(23):4 pages.

Wartiovaara et al., CRISPR-Cas9 gene editing of CD34+cells to increase fetal hemoglobin (HbF) production. Collaborative Congress of the European-Society-of-Gene-and-Cell-Therapy. Oct. 2015;26.

Xie et al., Seamless gene correction of [beta]-thalassemia mutation in patient-specific iPSCs using CRISPR/Cas9 and piggyBac. Genome Res. Aug. 5, 2014;24(9):1526-1533.

Xu et al., Both TALENs and CRISPR/Cas9 directly target the HBB IVS2-654 (C>T) mutation in [beta]-thalassemia-derived iPSCs. Scientific Reports. Jul. 9, 2015;5(12065):1-12.

Yannaki et al., Hematopoietic stem cell mobilization for gene therapy: superior mobilization by the combination of granulocyte-colony stimulating factor plus plerixafor in patients with β-thalassemia major. Human gene therapy. Oct. 1, 2013;24(10):852-60.

Zhu, Overview of guide RNA design tools for CRISPR-Cas9 genome editing technology. Frontiers in Biology. Aug. 2015;10(4):289-296.

* cited by examiner

Figure 1B

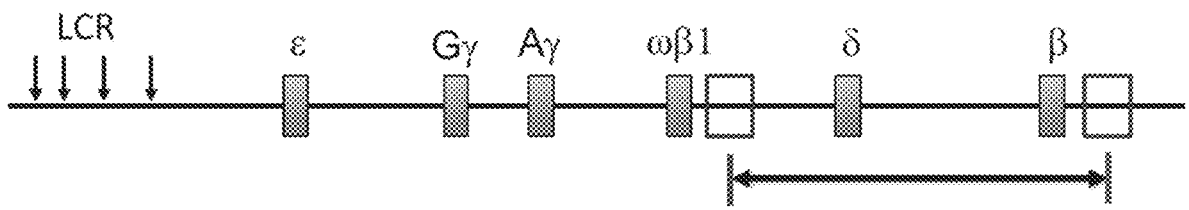

Figure 1C

HPFH5

| Guide | Sequence | SEQ ID NO | Location | Cut Site |
|---|---|---|---|---|
| HPFH5-04 | gCTGAGTTCTAAAATCATCG | SEQ ID NO: 4 | Chr11:5237756-5237778 | Chr11:5237762 |
| HPFH5-15 | gTGTCTTATTACCCTGTCAT | SEQ ID NO: 15 | Chr11:5224763-5224785 | Chr11:5224769 |
| HPFH5-19 | gTTGGGGTGGGCCTATGACA | SEQ ID NO: 19 | Chr11:5224752-5224774 | Chr11:5224768 |
| HPFH5-20 | gTTTGGGGTGGGCCTATGAC | SEQ ID NO: 20 | Chr11:5224751-5224773 | Chr11:5224767 |
| HPFH5_44 | gGGTGGGAAAATAGACCAAT | SEQ ID NO: 43 | Chr11:5226804-5226826 | Chr11:5226820 |
| HPFH5_56 | gATCAGAATGGCCCTAGTCT | SEQ ID NO: 55 | Chr11:5229841-5229863 | Chr11:5229857 |
| HPFH5_73 | gAAAGCAAGGGAACCGTACA | SEQ ID NO: 72 | Chr11:5232701-5232723 | Chr11:5232707 |
| HPFH5_84 | gGTGTTTTAGGCTAATATAG | SEQ ID NO: 83 | Chr11:5234752-5234774 | Chr11:5234768 |
| HPFH5_87 | gCATTTGTGGATACTATTAA | SEQ ID NO: 86 | Chr11:5235767-5235789 | Chr11:5235773 |
| HPFH5_93 | gTCTGTTAATTCCAAAGACT | SEQ ID NO: 92 | Chr11:5236813-5236835 | Chr11:5236829 |

Figure 1D

```
HPFH5-4           GCTGAGTTCTAAAATCATCG
HPFH5-5                  GCTAAAATCATCGGGGATTT
HPFH5-6                   GTAAAATCATCGGGATTTT
HPFH5-5'  AAAATCGATACTGAGTTCTAAAATCATCGGGGATTTTGGGGACTATGTCTTACTTCA

HPFH5-15                 GTGTCTTATTACCCTGTCAT
HPFH5-3'  ATTCACTACTGTCTTATTACCCTGTCATAGGCCCACCCCAAATGGAAG
HPFH5-1  20                        GTCATAGGCCCACCCCAAAC
HPFH5-2  19                       TGTCATAGGCCCACCCCAAC
```

HPFH5-4 = SEQ ID NO: 4
HPFH5-5 = SEQ ID NO: 5
HPFH5-6 = SEQ ID NO: 6
HPFH5-5' = SEQ ID NO: 144
HPFH5-15 = SEQ ID NO: 15
HPFH5-3' = SEQ ID NO: 145
HPFH5-19 = SEQ ID NO: 19
HPFH5-20 = SEQ ID NO: 20

Figure 2C

```
AAGACATAGTCCCCAAAATCCCCGATGATTTTAGAACTCAGTATCGATTTTAA
AAGACATAGTCCCCAAAATCCC:::TGATTTTAGAACTCAGTATCGATTTTAA
AAGACATAGTCCCCAAAATCCCCGA:::TTTTAGAACTCAGTATCGATTTTAA
AAGACATAGTCCCCAAAATCCCCGA:::TTTTAGAACTCAGTATCGATTTTAA
AAGACATAGTCCCCAAAATCCCCGA::::TTAGAACTCAGTATCGATTTTAA
AAGACATAGTCCCCAAAATCCCCG:TGATTTTAGAACTCAGTATCGATTTTAA
```

First line = SEQ ID NO: 146
Second line = SEQ ID NO: 147
Third line = SEQ ID NO: 148
Fourth line = SEQ ID NO: 149
Fifth line = SEQ ID NO: 150
Sixth line = SEQ ID NO: 151

Figure 4

```
                   HPFH5-5'                                                        HPFH5-3'
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGATCATAGGCCCACCCCAAATGGAAGTCCCATTCTTCCTCAGGAT
TGTGAAATCTCAAGGAAGTATGAAGTAAGACATAGTCCCCAAAATCCCCGAGA::CATAGGCCCACCCCAAATGGAAGTCCCATTCTTCCTCAGGAT
TGTGAAATCTCAAGGAAGTATGAAGTAAGACATAGTCCCCAA:::::::::::::::::TAGGCCCACCCCAAATGGAAGTCCCATTCTTCCTCAGGAT
TGTGAAATCTCAAGGAAGTATGAAGTAAGACATAGTCCCCAAAATCCCCGATGCATAGGCCCACCCCAAATGGAAGTCCCATTCTTCCTCAGGA
TGTGAAATCTCAAGGAAGTATGAAGTAAGACATAGTCCCCAAAATCCCCGATTTTCATAGGCCCACCCCAAATGGAAGTCCCATTCTTCCTCAG
```

First line = SEQ ID NO: 152
Second line = SEQ ID NO: 153
Third line = SEQ ID NO: 154
Fourth line = SEQ ID NO: 155
Fifth line = SEQ ID NO: 156
Sixth line = SEQ ID NO: 157
Seventh line = SEQ ID NO: 158
Eigth line = SEQ ID NO: 159
Ninth line = SEQ ID NO: 160
Tenth line = SEQ ID NO: 161

Figure 5

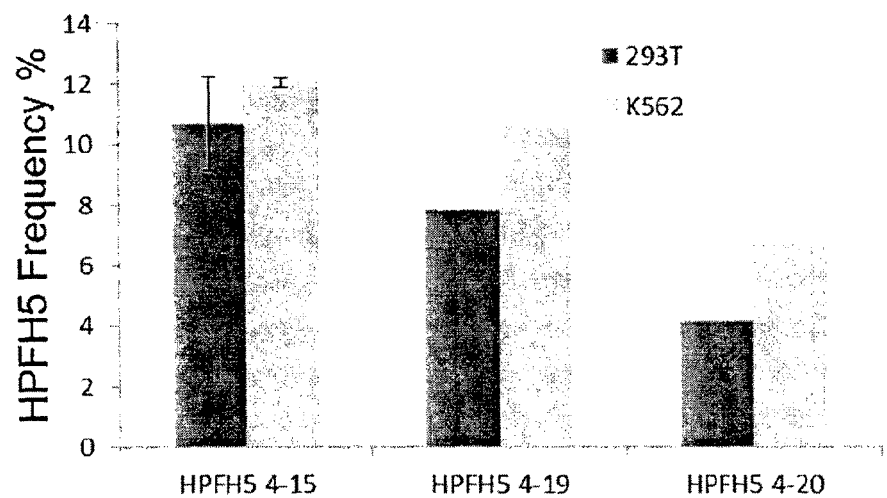

Figure 6A

| Site | Sequence | Score |
|---|---|---|
| HPFH5_4ON | ACTGAGTTCTAAAATCATCGGGG | 0 |
| HPFH5_4OT1 | CCTGATCTCTTAAATCATCGTGG | 1.14 |
| HPFH5_15ON | CTGTCTTATTACCCTGTCATAGG | 0 |
| HPFH5-15_OT1 | TTTGCTTATTACCCTGTCATAAG | 0.32 |
| HPFH5-15_OT2 | CTGATTTATAACCCTGTCATCGG | 0.86 |
| HPFH5-15_OT3 | ATGTGTCATCACCCTGTCATCAG | 0.92 |
| HPFH5-15_OT4 | GTGTCTTCTTTCCCTGTCATTGG | 0.97 |
| HPFH5-15_OT5 | GTGTCTTCTTCCCCTGTCATGAG | 0.97 |
| HPFH5-15_OT6 | TACTCTTATTCCCTGTCATCAG | 0.98 |
| HPFH5-15_OT7 | CTTTTTTATTAACCTGTCATTGG | 1.14 |
| HPFH5-15_OT8 | ATGAGTTATTAGCCTGTCATTGG | 1.16 |
| HPFH5-15_OT9 | CATTCTTATTACACTGTCATCAG | 1.38 |
| HPFH5-15_OT10 | TAGTTTTATTACACTGTCATCAG | 1.42 |
| HPFH5-15_OT11 | ATGTCTTGATAGCCTGTCATAAG | 1.42 |

HPFH5_4ON = SEQ ID NO: 162  
HPFH5_4OT1 = SEQ ID NO: 163  
HPFH5_15ON = SEQ ID NO: 164  
HPFH5-15_OT1 = SEQ ID NO: 165  
HPFH5-15_OT2 = SEQ ID NO: 166  
HPFH5-15_OT3 = SEQ ID NO: 167  
HPFH5-15_OT4 = SEQ ID NO: 168  
HPFH5-15_OT5 = SEQ ID NO: 169  
HPFH5-15_OT6 = SEQ ID NO: 170  
HPFH5-15_OT7 = SEQ ID NO: 171  
HPFH5-15_OT8 = SEQ ID NO: 172  
HPFH5-15_OT9 = SEQ ID NO: 173  
HPFH5-15_OT10 = SEQ ID NO: 174  
HPFH5-15_OT11 = SEQ ID NO: 175

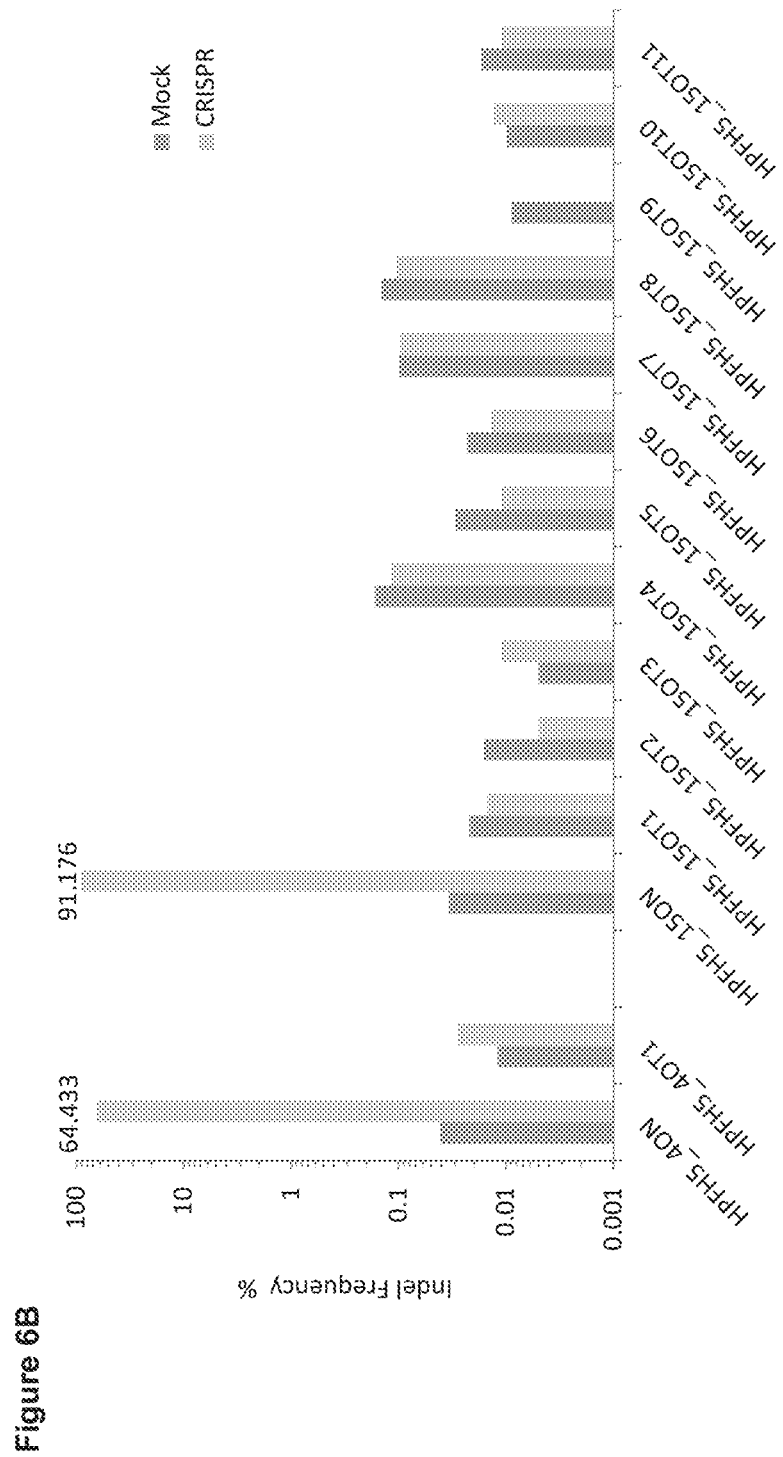

Figure 7A

HPFH5

| Guide | Sequence | SEQ ID NO | Location | Cut Site |
|---|---|---|---|---|
| HPFH5_36 | gACAGACCAGCACGTTGCCC | SEQ ID NO: 35 | Chr11:5225702-5225724 | Chr11:5225718 |
| HPFH5_37 | gCAGCTCCTGGGCAACGTGC | SEQ ID NO: 36 | Chr11:5225708-5225730 | Chr11:5225714 |
| HPFH5_38 | gTTAGCAAAAGGGCCTAGCT | SEQ ID NO: 37 | Chr11:5225758-5225780 | Chr11:5225774 |
| HPFH5_39 | gATTATTCTGAGTCCAAGCT | SEQ ID NO: 38 | Chr11:5225771-5225793 | Chr11:5225777 |
| HPFH5_40 | gGCTGCTGGTGGTCTACCCT | SEQ ID NO: 39 | Chr11:5226778-5226800 | Chr11:5226784 |
| HPFH5_41 | gGTAGACCACCAGCAGCCTA | SEQ ID NO: 40 | Chr11:5226783-5226805 | Chr11:5226799 |
| HPFH5_42 | gTAGACCACCAGCAGCCTAA | SEQ ID NO: 41 | Chr11:5226784-5226806 | Chr11:5226800 |
| HPFH5_43 | gCCACCAGCAGCCTAAGGGT | SEQ ID NO: 42 | Chr11:5226788-5226810 | Chr11:5226804 |
| HPFH5_44 | gGGTGGGAAAATAGACCAAT | SEQ ID NO: 43 | Chr11:5226804-5226826 | Chr11:5226820 |
| HPFH5_45 | gCCCAAAGTGTGACTATCAA | SEQ ID NO: 44 | Chr11:5227835-5227857 | Chr11:5227851 |
| HPFH5_46 | gCCCATTGATAGTCACACTT | SEQ ID NO: 45 | Chr11:5227837-5227859 | Chr11:5227843 |
| HPFH5_47 | gCCAAAGTGTGACTATCAAT | SEQ ID NO: 46 | Chr11:5227836-5227858 | Chr11:5227852 |
| HPFH5_48 | gCTATCAATGGGGTAATCAG | SEQ ID NO: 47 | Chr11:5227847-5227869 | Chr11:5227863 |
| HPFH5_49 | gGTAATCAGTGGTGTCAAAT | SEQ ID NO: 48 | Chr11:5227858-5227880 | Chr11:5227874 |
| HPFH5_50 | gACCTGTCTCAACCCTCATC | SEQ ID NO: 49 | Chr11:5228644-5228666 | Chr11:5228660 |
| HPFH5_51 | gACCTGATGAGGGTTGAGAC | SEQ ID NO: 50 | Chr11:5228646-5228668 | Chr11:5228652 |
| HPFH5_52 | gCACACACGCAGAAAGTGTT | SEQ ID NO: 51 | Chr11:5228698-5228720 | Chr11:5228714 |
| HPFH5_53 | gTGGTTCTTCTATGGCTATC | SEQ ID NO: 52 | Chr11:5228717-5228739 | Chr11:5228733 |
| HPFH5_54 | gTGCCTATGTATGATTATAG | SEQ ID NO: 53 | Chr11:5228758-5228780 | Chr11:5228774 |
| HPFH5_55 | gTATCAGAATGGCCCTAGTC | SEQ ID NO: 54 | Chr11:5229840-5229862 | Chr11:5229856 |
| HPFH5_56 | gATCAGAATGGCCCTAGTCT | SEQ ID NO: 55 | Chr11:5229841-5229863 | Chr11:5229857 |
| HPFH5_57 | gTCTAAGTATACCCAGACTA | SEQ ID NO: 56 | Chr11:5229852-5229874 | Chr11:5229858 |
| HPFH5_58 | gCTCTAAGTATACCCAGACT | SEQ ID NO: 57 | Chr11:5229853-5229875 | Chr11:5229859 |
| HPFH5_59 | gCTAGTCTGGGTATACTTAG | SEQ ID NO: 58 | Chr11:5229854-5229875 | Chr11:5229869 |
| HPFH5_60 | gTTCAGTATGTCTGAATGAA | SEQ ID NO: 59 | Chr11:5230701-5230723 | Chr11:5230707 |
| HPFH5_61 | gAAATTAAAGCCAAATCTTG | SEQ ID NO: 60 | Chr11:5230786-5230808 | Chr11:5230802 |
| HPFH5_62 | gGAATTAATTCCTCAAGATT | SEQ ID NO: 61 | Chr11:5230796-5230818 | Chr11:5230802 |
| HPFH5_63 | gTTAAAACAAAGTATAGGAA | SEQ ID NO: 62 | Chr11:5230817-5230839 | Chr11:5230823 |
| HPFH5_64 | gGTACATGTACAAGTTATAT | SEQ ID NO: 63 | Chr11:5230858-5230880 | Chr11:5230874 |
| HPFH5_65 | gACACATTGTCAGTATATTC | SEQ ID NO: 64 | Chr11:5231674-5231696 | Chr11:5231690 |
| HPFH5_66 | gATCCTTCTAATTTTACCTA | SEQ ID NO: 65 | Chr11:5231840-5231862 | Chr11:5231856 |
| HPFH5_67 | gTGCCATAGGTAAAATTAGA | SEQ ID NO: 66 | Chr11:5231843-5231865 | Chr11:5231849 |
| HPFH5_68 | gTGAGCACCATTTTTGCCAT | SEQ ID NO: 67 | Chr11:5231856-5231877 | Chr11:5231862 |
| HPFH5_69 | gATGGCAAAAATGGTGCTCA | SEQ ID NO: 68 | Chr11:5231858-5231880 | Chr11:5231874 |
| HPFH5_70 | gCACCCATTAATGCCTTGTA | SEQ ID NO: 69 | Chr11:5232689-5232710 | Chr11:5232704 |
| HPFH5_71 | gAACCGTACAAGGCATTAAT | SEQ ID NO: 70 | Chr11:5232691-5232712 | Chr11:5232697 |

| | | | | |
|---|---|---|---|---|
| HPFH5_72 | gGAACCGTACAAGGCATTAA | SEQ ID NO: 71 | Chr11:5232692-5232714 | Chr11:5232698 |
| HPFH5_73 | gAAAGCAAGGGAACCGTACA | SEQ ID NO: 72 | Chr11:5232701-5232723 | Chr11:5232707 |
| HPFH5_74 | gTCCCTATCTGTAGAGCCTC | SEQ ID NO: 73 | Chr11:5232762-5232783 | Chr11:5232777 |
| HPFH5_75 | gAGCCTCTCCCATACCCATG | SEQ ID NO: 74 | Chr11:5233650-5233672 | Chr11:5233666 |
| HPFH5_76 | gCTCCACATGGGTATGGGAG | SEQ ID NO: 75 | Chr11:5233653-5233675 | Chr11:5233659 |
| HPFH5_77 | gTGTCTCCACATGGGTAT | SEQ ID NO: 76 | Chr11:5233658-5233680 | Chr11:5233664 |
| HPFH5_78 | gTTGTCTCCACATGGTA | SEQ ID NO: 77 | Chr11:5233659-5233681 | Chr11:5233665 |
| HPFH5_79 | gTTCTAAGTGCAGAATTAGC | SEQ ID NO: 78 | Chr11:5233688-5233710 | Chr11:5233704 |
| HPFH5_80 | gGCGGTGGGGAGATATGTAG | SEQ ID NO: 79 | Chr11:5234677-5234699 | Chr11:5234683 |
| HPFH5_81 | gTGCTGAAAGAGATGCGGTG | SEQ ID NO: 80 | Chr11:5234690-5234712 | Chr11:5234696 |
| HPFH5_82 | gCTGCTGAAAGAGATGCGGT | SEQ ID NO: 81 | Chr11:5234691-5234713 | Chr11:5234697 |
| HPFH5_83 | gACTGCTGAAAGAGATGCGG | SEQ ID NO: 82 | Chr11:5234692-5234714 | Chr11:5234698 |
| HPFH5_84 | gGTGTTTAGGCTAATATAG | SEQ ID NO: 83 | Chr11:5234752-5234774 | Chr11:5234768 |
| HPFH5_85 | gTCAAATTTTGGTGGTGATA | SEQ ID NO: 84 | Chr11:5235684-5235706 | Chr11:5235700 |
| HPFH5_86 | gTACAATAGTATAACCCCTT | SEQ ID NO: 85 | Chr11:5235740-5235762 | Chr11:5235756 |
| HPFH5_87 | gCATTTGTGGATACTATTAA | SEQ ID NO: 86 | Chr11:5235767-5235789 | Chr11:5235773 |
| HPFH5_88 | gTAATAGTATCCACAAATGC | SEQ ID NO: 87 | Chr11:5235770-5235792 | Chr11:5235786 |
| HPFH5_89 | gATCAAGCATCCAGCATTTG | SEQ ID NO: 88 | Chr11:5235780-5235802 | Chr11:5235786 |
| HPFH5_90 | gTGTCATTTTTAACAGGTAG | SEQ ID NO: 89 | Chr11:5236644-5236666 | Chr11:5236650 |
| HPFH5_91 | gGTAAATTCTTAAGGCCATG | SEQ ID NO: 90 | Chr11:5236773-5236795 | Chr11:5236789 |
| HPFH5_92 | gGATCAAATAACAGTCCTCA | SEQ ID NO: 91 | Chr11:5236788-5236810 | Chr11:5236794 |
| HPFH5_93 | gTCTGTTAATTCCAAAGACT | SEQ ID NO: 92 | Chr11:5236813-5236835 | Chr11:5236829 |
| HPFH5_94 | gCTGAAATGATTTTACACAT | SEQ ID NO: 93 | Chr11:5236859-5236881 | Chr11:5236875 |

Corfu

| Guide | Sequence | SEQ ID NO | Location | Cut Site |
|---|---|---|---|---|
| HPFHCS-02 | gTAGACCACCAGTAATCTGA | SEQ ID NO: 105 | Chr11:5234198-5234220 | Chr11:5234214 |
| HPFHCS-04 | gTGGTATGGGAGGTATACTA | SEQ ID NO: 107 | Chr11:5237949-5237971 | Chr11:5237965 |
| HPFHCS-06 | gGTATACCTCCCATACCATG | SEQ ID NO: 109 | Chr11:5237945-5237967 | Chr11:5237951 |
| HPFHCL-01 | gGTGTGCTGGCCCGCAACTT | SEQ ID NO: 111 | Chr11:5233049-5233071 | Chr11:5233055 |
| HPFHCL-02 | gTGGGGCAGAAGTCGTTGCT | SEQ ID NO: 112 | Chr11:5233476-5233498 | Chr11:5233482 |
| HPFHCL-08 | gCCACTCAAGAGATATGGTG | SEQ ID NO: 118 | Chr11:5240337-5240359 | Chr11:5240353 |

| 3' guide | 5' guide | | |
|---|---|---|---|
| | CS-02 | CL_01 | CL_02 |
| CS_04 | 1&2 | | |
| CS_06 | 3&4 | | |
| CL_08 | | 5&6 | 7&8 |

Kenya

| Guide | Sequence | SEQ ID NO | Location | Cut Site |
|---|---|---|---|---|
| HPFHK-02 | gTCTTCAGCCTACAACATAC | SEQ ID NO: 122 | Chr11:5248713-5248735 | Chr11:5248719 |
| HPFHK-10 | gTGCCTAGTACATTACTATT | SEQ ID NO: 130 | Chr11:5226235-5226257 | Chr11:5226241 |
| HPFHK-14 | gACGAATGATTGCATCAGTG | SEQ ID NO: 134 | Chr11:5226448-5226470 | Chr11:5226454 |
| HPFHK-17 | gTTAAGTTCATGTCATAGGA | SEQ ID NO: 137 | Chr11:5226507-5226529 | Chr11:5226513 |

High $^A\gamma$ HPFH (top panel) = SEQ ID NO: 176
Normal (top panel) = SEQ ID NO: 177
High $^A\gamma$ HPFH (bottom panel) = SEQ ID NO: 178
Normal (bottom panel) = SEQ ID NO: 179 top sequence = SEQ ID NO: 180
bottom sequence = SEQ ID NO: 181

Figure 14C

Small Deletion

| Guide | Sequence | Location | Cut Site | Location | Cut Site |
|---|---|---|---|---|---|
| >HPFHSD_01 | gTTTGCCTTGTCAAGGCTAT | Chr11:5249950-5249972 | Chr11:5249966 | Chr11:5254874-5254896 | Chr11:5254890 |
| >HPFHSD_02 | gTTGTCAAGGCTATTGGTCA | Chr11:5249956-5249978 | Chr11:5249972 | Chr11:5254880-5254902 | Chr11:5254896 |

HPFHSD_01 = SEQ ID NO: 138
HPFHSD_02 = SEQ ID NO: 139

Figure 15C

```
                  13bp Deletion
                 ←—————————————→
AAGACTATTGGTCAAGTTTGCCTTGTCAAGGCTATTGGTCAAGGCAAGGCTGGCCAACCCATGGGTGGAGTTTAG
AAGACTATTGGTCAAGTTTGCC::::::::::::::::::::::::::::::::::::::::TGGGTGGAGTTTAG
AAGACTATTGGTCAAGTTTGCCTT:::::::::::::GGTCAAGGCAAGGCTGGCCAACCCATGGGTGGAGTTTAG
AAGACTATTGGTCAAGTTTGCCTT::::::::::::GTCAAGGCAAGGCTGGCCAACCCATGGGTGGAGTTTAG
AAGACTATTGGTCAAGTTTGCCTTGTCAAGGCTA:::::::::::::GCTGGCCAACCCATGGGTGGAGTTTAG  ← Alternative
AAGACTATTGGTCAAGTTTGCCTTGTCAAGGC::::::AAGGCAAGGCTGGCCAACCCATGGGTGGAGTTTAG     "13bp deletion"
AAGACTATTGGTCAAGTTTGCCTTGTCAAGGCT::::TCAAGGCAAGGCTGGCCAACCCATGGGTGGAGTTTAG
AAGACTATTGGTCAAGTTTGCCTTGTCAAGGCTATT::CAAGGCAAGGCTGGCCAACCCATGGGTGGAGTTTAG
AAGACTATTGGTCAAGTTTGCCTTGTCAAGGCTATTGG:CAAGGCAAGGCTGGCCAACCCATGGGTGGAGTTTAG
```

First line = SEQ ID NO: 182  
Second line = SEQ ID NO: 183  
Third line = SEQ ID NO: 184  
Fourth line = SEQ ID NO: 185  
Fifth line = SEQ ID NO: 186  
Sixth line = SEQ ID NO: 187  
Seventh line = SEQ ID NO: 188  
Eighth line = SEQ ID NO: 189  
Ninth line = SEQ ID NO: 190

Figure 16A
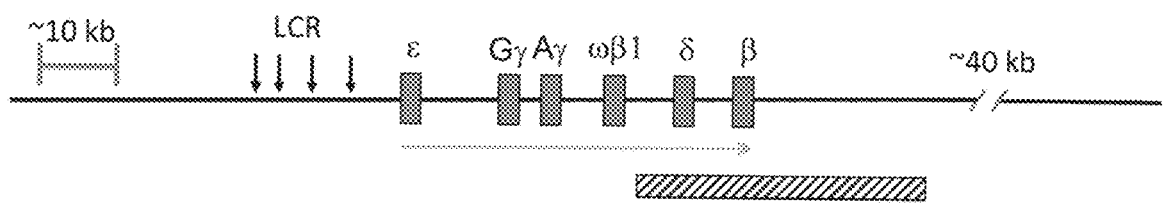
Figure 16B
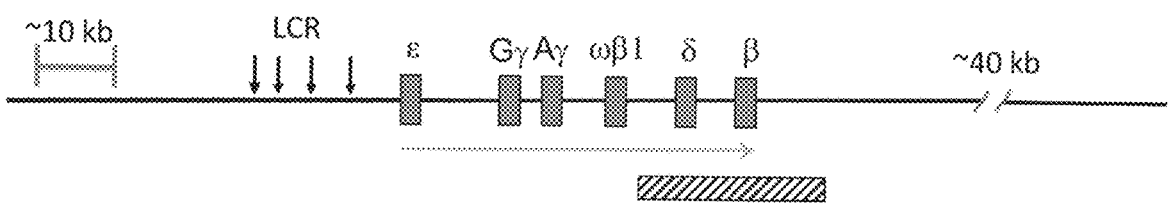
Figure 16C
ggggcccct cccc cactatctcaatgcaaaTa c g c aa a gg ccc ggctaaact cc cc tgggttgg
SEQ ID NO: 191

MATERIALS AND METHODS FOR TREATMENT OF HUMAN GENETIC DISEASES INCLUDING HEMOGLOBINOPATHIES

CROSS-REFERENCE TO RELATED APPLICATIONS

This application claims the benefit of U.S. Provisional Patent Application Ser. No. 62/119,774, filed Feb. 23, 2015, which is incorporated herein by reference in its entirety.

INCORPORATION BY REFERENCE OF SEQUENCE LISTING

A sequence listing is provided herein as a text file titled "49383PCT_Seqlisting.txt", which was created on Feb. 23, 2016 and has a size of 47,179 bytes. The contents of this sequence listing are incorporated herein by reference in its entirety.

FIELD

The present application provides materials and methods for treating human genetic diseases including hemoglobinopathies. More specifically, the application provides methods for producing progenitor cells that are genetically modified via genome editing to increase the production of fetal hemoglobin (HbF), as well as modified progenitor cells, including for example CD34$^+$ human hematopoietic stem cells (hHSCs) producing increased levels of HbF, and methods of using such cells for treating hemoglobinopathies such as sickle cell anemia and β-thalassemia. The application also provides materials and methods comprising modified polynucleotides and methods of using such polynucleotides for treating human genetic diseases including hemoglobinopathies.

BACKGROUND

There are numerous human genetic diseases that continue to represent significant medical problems, and for which existing approaches are insufficient, expensive, and/or associated with complications limiting their effectiveness or safety. Hemoglobinopathies represent one such class of diseases, as described in further detail herein, although there are many others that could benefit from approaches that can safely and effectively correct or otherwise ameliorate one or more conditions associated with the disease.

Hemoglobinopathies encompass a number of anemias that are associated with changes in the genetically determined structure or expression of hemoglobin. These include changes to the molecular structure of the hemoglobin chain, such as occurs with sickle cell anemia, as well as changes in which synthesis of one or more chains is reduced or absent, such as occurs in various thalassemias.

Disorders specifically associated with the β-globin protein are referred to generally as β-hemoglobinopathies. For example, β-thalassemias result from a partial or complete defect in the expression of the β-globin gene, leading to deficient or absent hemoglobin A (HbA). HbA is the most common human hemoglobin tetramer and consists of two α-chains and two β-chains ($α_2β_2$). β-thalassemias are due to mutations in the adult β-globin gene (HBB) on chromosome 11, and are inherited in an autosomal, recessive fashion. β-thalassemia or β-thal is classified into two clinically-significant types (which are a focus of symptom management, medical treatments and the present application) that are distinguished by the severity of symptoms: β-thalassemia major (or $β^0$, in which mutations block production of β-globin chains, resulting in a severe condition that is also known as "Cooley's anemia") and β-thalassemia intermedia (or $β^+$, an intermediate condition in which mutations reduce but do not block production of β-globin chains). In contrast, β-thalassemia minor or β-thalassemia trait refers to the heterozygous situation in which only one of the β-globin alleles contains a mutation, so that β-globin chains can be produced via expression from the other (i.e. unmutated) chromosome 11 allele. While such individuals are carriers of a β-thalassemia mutant allele that they may pass on to their children, individuals with β-thalassemia minor are generally either asymptomatic or nearly asymptomatic themselves as a result of β-globin production from the unaffected allele.

The signs and symptoms of thalassemia major generally appear within the first 2 years of life, when children with the disease can develop life-threatening anemia. Children with thalassemia major often fail to gain sufficient weight or grow at the expected rate (failure to thrive) and may develop jaundice. Affected individuals may also have an enlarged spleen, liver, and heart, and their bones may be misshapen. Many people with thalassemia major have such severe symptoms that they need frequent blood transfusions to replenish their red blood cell supply, which is referred to as transfusion-dependent thalassemia. While transfusions have been a critical life-saver for many patients, they are expensive and are frequently associated with significant side effects. Among others, over time the administration of iron-containing hemoglobin from chronic blood transfusions tends to lead to a buildup of iron in the body, which can result in liver, heart, and endocrine problems.

Thalassemia intermedia is milder than thalassemia major. The signs and symptoms of thalassemia intermedia appear in early childhood or later in life. Although symptoms are less severe, affected individuals still have mild to moderate anemia and may also suffer from slow growth and bone abnormalities.

Sickle cell disease (SCD) is a group of disorders that affects millions of people worldwide. It is most common among people who live in or whose ancestors come from Africa; Mediterranean countries such as Greece, Turkey, and Italy; the Arabian Peninsula; India; Spanish-speaking regions in Central and South America, and parts of the Caribbean. However, SCD is also the most common inherited blood disorder in the United States. SCD includes sickle cell anemia, as well as sickle hemoglobin C disease (HbSC), sickle beta-plus-thalassemia (HbS/$β^+$) and sickle beta-zero-thalassemia) (HbS/$β^0$).

Sickle cell anemia (SCA), which is the most prevalent form of SCD, is among the most common severe monogenic disorders worldwide, with approximately 250,000 children born with SCD every year. The incidence of SCA is greatest in West and Central Africa, where 1-2% of babies are born with the disease, and as many as 25% of people are heterozygous carriers. The SCA point mutation is believed to have been spread through selective advantage because heterozygosity provides modest protection against death from childhood malaria. In India, where malaria is also prevalent, it is estimated that there are more than 2.5 million heterozygous carriers of SCA and approximately 150,000 homozygotes with the disease.

Despite the relative absence of malaria in North America and Europe, the fact that each has large populations with genetic origins in affected areas has meant that both regions have substantial populations of heterozygous SCA carriers, and therefore affected homozygous individuals. For example, the US Centers for Disease Control (CDC) estimates that there are approximately 90,000 to 100,000 Americans with SCA; and incidence is also high in countries of Western Europe, particularly those with large immigrant populations, with an estimated 10,000 in France and 12,000 to 15,000 in the United Kingdom for example. Associated costs to healthcare systems are likewise substantial. In a five-year US study conducted from 1989 through 1993, the CDC estimated that SCD resulted in more than 75,000 hospitalizations annually, and cost approximately $0.5 billion. System wide costs would be expected to be substantially greater now given the steady rise in healthcare costs over the intervening two decades.

All forms of SCD are caused by mutations in the β-globin structural gene (HBB). Sickle cell anemia (SCA) is an autosomal recessive disease caused by a single missense mutation in the sixth codon of the β-globin gene (HBB; A→T) resulting in the substitution of glutamic acid by valine (Glu→Val). The mutant protein, when incorporated into hemoglobin (Hb), results in unstable hemoglobin HbS (which is $\alpha_2\beta_2^S$) in contrast to normal adult hemoglobin or HbA (which is $\alpha_2\beta_2^A$). Upon de-oxygenation, HbS polymerizes to form HbSS through hydrophobic interactions between $\beta^S$-6 valine of one tetramer and β-85 phenylalanine and β-88 leucine of an adjacent tetramer in the erythron, which leads to rigidity and vaso-occlusion [Atweh, Semin. Hematol. 38(4):367-73 (2001)].

When HbS is the predominant form of hemoglobin, as in individuals with SCA, their red blood cells (RBCs) tend to be distorted into a sickle or crescent shape. The sickle-shaped RBCs die prematurely, which can lead to anemia. In addition, the sickle-shaped cells are less flexible than normal RBCs and tend to get stuck in small blood vessels causing vaso-occlusive events. Such vaso-occlusive events are associated with tissue ischemia leading to acute and chronic pain as well as organ damage that can affect any organ in the body, including the bones, lungs, liver, kidneys, brain, eyes, and joints. The spleen is particularly subject to infarction and the majority of individuals with SCD are functionally asplenic in early childhood, increasing their risk for certain types of bacterial infections. Occlusions of small vessels can also cause acute episodic febrile illness called "crises," which are associated with severe pain and multiple organ dysfunction. Over the course of decades there is progressive organ disease and premature death.

Children with SCD may be diagnosed by newborn screening but otherwise do not present until later, when levels of fetal hemoglobin (HbF) decline and levels of HbS increase as a result of the hemoglobin allelic "switch" from fetal hemoglobin (encoded by HBG1 (A-gamma, also written $^A\gamma$) and HBG2 (G-gamma, also written $^G\gamma$)) to the adult β form encoded by HBB). The switch from HbF to the adult form of β-globin (i.e. HbA in unaffected children or HbS in those with SCA) typically begins a few months prior to birth and is complete by about the age of 6 months. The clinical effects of SCD are not manifested until HbF levels become significantly low relative to HbS, which typically occurs two to three months after birth. SCD often first presents as dactylitis or "hand-foot syndrome," a condition associated with pain in the hands and/or feet that may be accompanied by swelling. In addition, the spleen can become engorged with blood cells resulting in a condition known as "splenic sequestration." Hemolysis associated with SCD can result in anemia, jaundice, cholelithiasis, as well as delayed growth. Individuals with the highest rates of SCD hemolysis also tend to experience pulmonary artery hypertension, priapism, and leg ulcers.

Sickle cell anemia (homozygous HbSS) accounts for 60%-70% of sickle cell disease in the US. The other forms of sickle cell disease result from coinheritance of HbS with other abnormal globin β chain variants, the most common forms being sickle-hemoglobin C disease (HbSC) and two types of sickle β-thalassemia (HbSβ+-thalassemia and HbSβ°-thalassemia). The β-thalassemias are divided into β+-thalassemia, in which reduced levels of normal β-globin chains are produced, and β°-thalassemia, in which there is no β-globin chain synthesis. Other globin β chain variants such as D-Punjab, O-Arab, and E also result in sickle cell disease when coinherited with HbS.

Although improvements in the management of SCD have reduced mortality in affected children followed up since neonatal screening, the mainstay of treatment for the majority of individuals with SCD remains supportive. Current treatments aim at relieving symptoms and treating complications such as: pain from vaso-occlusive crisis, infection, anemia, stroke, priapism, pulmonary hypertension or chronic organ damage. Preventative therapies include infection prophylaxis with regular penicillin, vaccination against *Streptococcus pneumoniae* and *Haemophilus influenzae*, as well as regular transfusions in children with abnormal transcranial Doppler ultrasonography to prevent strokes and iron chelation for transfusional iron overload. Stroke is also considered an indication for bone marrow transplantation in children and adolescents, who have siblings with identical human leukocyte antigen (HLA). Effective treatment of acute pain is one of the most common problems raised by the management of SCA. Thus, at the present time, definitive therapies that substantially alter the natural history of the disease (such as regular transfusion or exchange transfusion, long-term hydroxycarbamide and HSC transplants) are limited.

WO2014/085593 relates to methods and compositions for treating hemoglobinopathies by targeting BCL11A distal regulatory elements that are purported to act as a stage specific regulator of fetal hemoglobin expression by repressing γ-globin induction. Thus, for example, claim 1 of WO2014/085593 is directed to a method for producing a progenitor cell having decreased BCL11A mRNA or protein expression, the method comprising contacting an isolated progenitor cell with an agent that binds the genomic DNA of the cell on chromosome 2 location 60,716,189-60,728,612 (according to UCSC Genome Browser hg 19 human genome assembly), thereby reducing the mRNA or protein expression of BCL11A.

For these and other targets, gene therapy has long been proposed as a potentially curative option for hemoglobinopathies (see, e.g., de Montalembert, *BMJ*, 337: a1397 (2008); Sheth et al., *British Journal of Haematology*, 162: 455-464 (2013), and references cited therein.

However, as recently summarized by Chandrakasan and Malik in a review entitled "Gene Therapy for Hemoglobinopathies: The State of the Field and the Future" [*Hematol Oncol Clin North Am.* 28(2): 199-216 (2014)] gene therapy for hemoglobinopathies has faced a number of challenges. For example, retroviral (RV) vectors were the first vectors to be used in clinical trials, and although vectors with long terminal repeats (LTRs) intact mediated high levels of transgene expression leading to clinical improvement, the success in the trials were soon marred by safety concerns from insertional oncogenesis from transactivation of cellular oncogenes by the RV LTR. The lympho-proliferation and leukemia in X-SCID was ascribed to insertion activation of the LMO2 oncogene. In the gene therapy trial for chronic granulomatous disease (CGD), after some initial success, there was silencing of transgene expression caused by methylation of the viral promoter, and myelodysplasia developed with monosomy 7 as a result of insertional activation of ecotropic viral integration site 1. Cf. Chandrakasan and Malik, supra, and references cited therein.

Bioengineering of HIV-1 devoid of any pathogenic elements resulted in the development of lentivirus (LV) vectors. Initial studies had established LV vectors as dependable vehicles for high-efficiency gene transfer. Bluebird Bio, Inc. is developing LentiGlobin® BB305, as a potential treatment in which autologous CD34+ hematopoietic stem cells (HSC) are transduced ex vivo with a lentiviral $B^{A\ T87Q}$-globin vector with the goal of inserting a fully functional human β-globin gene in patients with β-thalassemia major. The Bluebird study is intended to build on early clinical data from the LG001 study, in which the drug product had been administered to a patient with β-thalassemia major [Cavazzana-Calvo et al., Nature, 467: 318-322 (2010)].

Gene therapy using γ-globin has also been considered. However, γ-globin transcripts are known to be highly silenced in adults and so approaches to circumvent this have included driving γ-globin expression with β-globin promoters and enhancers, as described by Chandrakasan and Malik, supra.

However, the introduction of strong promoters and enhancers in the context of gene therapy, particularly with vectors that integrate at unpredictable locations within the genome (which include RV and LV vectors), raises safety concerns since the activation of a proto-oncogene or other harmful event can be triggered by the introduction of such elements. In the severe combined immunodeficiency disease (SCID) trials, for example, 5 of the 20 patients treated developed leukemia in connection with their treatment [Wu et al. Front Med. 5(4): 356-371 (2011)].

In sum, despite decades of efforts from researchers and medical professionals worldwide who have been trying to address hemoglobinopathies such β-thalassemia and sickle cell disease, and despite the promise of gene therapy approaches, there still remains a critical need for developing safe and effective treatments for these and related diseases which are among the most prevalent and debilitating genetic disorders.

SUMMARY

Provided herein are materials and methods for treating human genetic diseases including hemoglobinopathies. More specifically, the application provides methods for producing progenitor cells that are genetically modified via genome editing to increase the production of fetal hemoglobin (HbF), as well as modified progenitor cells, including for example CD34+ human hematopoietic stem cells (hHSCs) producing increased levels of HbF, and methods of using such cells for treating hemoglobinopathies such as sickle cell anemia and β-thalassemia.

The application also provides materials and methods comprising modified polynucleotides and methods of using such polynucleotides for ameliorating one or more symptoms or complications associated with human genetic diseases. Hemoglobinopathies serve as one example of such human genetic diseases but numerous others are well known, and materials and methods comprising modified polynucleotides and methods of using such polynucleotides can also be applied to ameliorating one or more symptoms or complications associated with such other human genetic diseases.

In the context of hemoglobinopathies, the methods described herein of increasing the level of fetal hemoglobin (HbF; two polypeptide chains of which are expressed from the γ-globin genes as described below) in human cells by genome editing, which can be used to treat hemoglobinopathies such as β-thalassemia and sickle cell disease, as well as components, kits and compositions for performing such methods, and cells produced by them, including without limitation autologous CD34+ human hematopoietic stem cells (hHSCs), can be administered to a patient suffering from a hemoglobinopathy.

In one aspect, provided herein are methods of increasing the level of HbF in a human cell by genome editing using DNA endonuclease to effect a pair of double-strand breaks (DSBs), the first positioned at a 5' DSB locus and the second positioned at a 3' DSB locus within the δβ-globin region of human chromosome 11, causing a DNA deletion of the region between the 5' DSB locus and the 3' DSB locus that results in increased expression of either or both γ-globin genes, thereby bringing about an increase in the level of HbF in the cell.

In another aspect, provided herein are methods of increasing the level of HbF in a human cell by genome editing using DNA endonuclease to effect a pair of DSBs, the first positioned at a 5' DSB locus and the second positioned at a 3' DSB locus within the δβ-globin region of human chromosome 11, causing an inversion of the region between the 5' DSB locus and the 3' DSB locus that results in increased expression of γ-globin, thereby bringing about an increase in the level of HbF in the cell.

In another aspect, provided herein are methods of increasing the level of HbF in a human cell by genome editing using DNA endonuclease to effect a DSB positioned at one or more loci within the β-globin region of human chromosome 11, causing deletions or insertions of chromosomal DNA at the one or more loci that result in increased expression of γ-globin, thereby increasing the level of HbF in the cell. In one type of method exemplifying this aspect, at least one DSB is positioned within the γ-globin regulatory region of human chromosome 11. In another type of method exemplifying this aspect, at least one DSB is positioned within the δβ-globin region of human chromosome 11.

Exemplary DNA endonucleases that may be used include, e.g., a Cas9 endonuclease, a zinc finger nuclease, a transcription activator-like effector nuclease (TALEN), a homing endonuclease, a dCas9-FokI nuclease or a MegaTal nuclease. DNA endonucleases may be introduced into the cell by a variety of means, including by the introduction and/or expression one or more polynucleotides encoding the DNA endonuclease, as known in the art and as described and illustrated further herein. In certain embodiments, DNA endonucleases and/or other components of the genome editing systems, such as guide RNAs in the case of Cas9 genome editing, are encoded by RNAs introduced into the cells. In certain embodiments, DNA endonucleases and/or other components of the genome editing systems, such as guide RNAs in the case of Cas9 genome editing, are encoded by modified RNAs introduced into the cells.

In some embodiments, the DNA endonuclease is a Cas9 endonuclease and the method comprises introducing into the cell one or more polynucleotides encoding Cas9 and two guide RNAs, the first guide RNA comprising a spacer sequence that is complementary to a segment of the 5' DSB locus, and the second guide RNA comprising a spacer sequence that is complementary to a segment of the 3' DSB locus. Both guide RNAs may be provided as single-molecule guide RNAs (comprising tracrRNA and crisprRNA), or either or both may be provided as double-molecule guide RNAs comprising a crisprRNA and a tracrRNA that are not joined to each other but rather are separate molecules.

In the context of treating hemoglobinopathies, and also in the use of genome editing to treat other human genetic diseases, the Cas9 endonuclease and/or the guide RNAs may also be provided as modified RNAs in which one or more aspects of the RNA molecule are modified relative to naturally-occurring RNAs as described further herein and in the art.

In other embodiments, the DNA endonuclease is a zinc finger nuclease (ZFN) and the method comprises introducing into the cell one or more polynucleotides encoding a first pair of ZFNs that target a segment of the 5' DSB locus, and a second pair of ZFNs that target a segment of the 3' DSB locus. Alternatively, TALENs or other endonucleases may be used.

In the context of treating hemoglobinopathies, and also in the use of genome editing to treat other human genetic diseases, the ZFN endonuclease, TALEN endonuclease or other endonuclease may also be provided as modified RNAs in which one or more aspects of the RNA molecule are modified relative to naturally-occurring RNAs as described further herein and in the art.

In some embodiments, the human cell to be modified is an isolated progenitor cell, and in some embodiments for the treatment of hemoglobinopathies it is a hematopoietic progenitor cell capable of giving rise to cells of the erythroid lineage. The isolated progenitor cell may also be an induced pluripotent stem cell.

In various embodiments, one or both DSB loci is proximal to a deletion associated with the hereditary persistence of fetal hemoglobin (HPFH) or δβ-thalassemia Corfu, as described and illustrated further herein. (The term "proximal to" refers herein to a position within, or nearby, a defined region either 5' or 3' of a particular reference point, is used herein with specific reference to these deletions, and is described in further detail below in the section entitled "Target Sequence Selection" and further illustrated by various exemplary embodiments provided herein.)

The deletions associated with HPFH and δβ-thalassemia Corfu are both associated with increases in HbF and are referred to herein collectively as HPFH deletions, a number of which are described and illustrated herein, and others are known in the art. Thus, the 5' DSB locus may be proximal to the 5' boundary of an HPFH deletion, the 3' DSB locus may be proximal to the 3' boundary of an HPFH deletion, or both, which would result in deletions that mimic naturally-occurring HPFH deletions. Exemplary deletions as illustrated herein include, e.g., the HPFH-4 deletion, the HPFH-5 deletion, the HPFH-Kenya deletion, the HPFH-Black deletion, the small deletion, the long Corfu deletion, and the short Corfu deletion.

Embodiments are also provided that have deletions sharing one or more segments that are deleted in HPFH, and that are associated with increased levels of HbF, but that are not co-terminous with naturally-occurring deletions.

In some aspects, deletions remove all or a portion of the δβ-globin region, as described further herein.

In some aspects, deletions remove all or a portion of the β-globin gene (HBB), as described further herein. In the context of sickle cell disease, disrupting or eliminating the β-globin gene can effectively reduce or eliminate the expression of sickle cell hemoglobin (HbS), which in addition to increasing the levels of fetal hemoglobin (HbF) can be of significant additional benefit to patients with SCD, such as sickle cell anemia. In certain embodiments, the method involves genome editing of cells from a patient with SCD, wherein HbF is increased and HbS is decreased.

In the context of β-thalassemias, problems associated with the lack of β-globin chains are exacerbated by the excess of unpaired α-globin chains, which interact with the red cell (RBC) membrane, causing oxidative damage to membrane skeletal components, and potentially other components resulting in shortened RBC survival, ineffective erythropoiesis and anemia. In certain embodiments, the method involves genome editing of cells from a patient with β-thalassemia, wherein HbF is increased and the level of unpaired α-globin chains is decreased.

Also provided are human cells that have been modified by the preceding methods to increase their levels of HbF. In certain embodiments, the cells are derived from a patient with SCD and the level of HbS in such cells is reduced. In certain other embodiments, the cells are derived from a patient with β-thalassemia and the level of unpaired α-globin chains in such cells is reduced. Such cells may be isolated progenitor cells, e.g., hematopoietic progenitor cells capable of giving rise to cells of the erythroid lineage. Isolated progenitor cells may be induced pluripotent stem cells.

Further provided herein are methods of ameliorating hemoglobinopathies by administration of cells that have been modified by the preceding methods to increase their levels of HbF. Exemplary hemoglobinopathies include, but are not limited to, sickle cell disease (including sickle cell anemia), hemoglobin C disease, hemoglobin C trait, hemoglobin S/C disease, hemoglobin D disease, hemoglobin E disease, a thalassemia, a condition associate with hemoglobin with increased oxygen affinity, a condition associated with hemoglobin with decreased oxygen affinity, unstable hemoglobin disease and methemoglobinemia.

Further provided herein are methods of modifying cells for the treatment of other human genetic diseases by genome editing that comprise the use of one or more modified polynucleotides as described herein.

Various other aspects are described and exemplified herein.

BRIEF DESCRIPTION OF THE DRAWINGS

FIGS. 1A-D show the genomic location of CRISPR target sites for the HPFH5 deletion. FIG. 1A shows a restriction map of the HPFH5 deletion variant (lower part) compared with wild type β-globin locus (upper part), as defined by Camaschella et al, *Haematologica*, 75(Suppl 5): 26-30 (1990). FIG. 1B shows a schematic of the human β-globin locus with hollow boxes highlighting illustrative HPFH5-like 5' and 3' target sites for CRISPR. The 12.9 kb deletion starts 3 kb 5' to the δ gene and ends 1.7 kb 3' to the end of the β gene (690 bp downstream from the β polyA signal), as described by Camaschella et al., supra. FIG. 1C shows the sequence and genomic location of illustrative CRISPR guide RNA target sites used to create HPFH5-like deletions in the human β-globin locus. FIG. 1D shows the alignment of exemplary guide RNA target sites on the target locus sequence. Top panel shows examples of 5' CRISPR target sites and the bottom panel shows examples of 3' CRISPR target sites.

FIGS. 2A-C show the activity of exemplary individual guide RNAs (gRNAs) targeting HPFH5. Activities of gRNAs were determined by using T7 Endonuclease I (T7EI)

assay. All experiments were carried out in triplicate. FIG. 2A shows the activity of gRNAs targeting the 5' boundary of the HPFH5 deletion in both HEK293T and K-562 cell lines. FIG. 2B shows the activity of gRNAs targeting the 3' boundary of the HPFH5 deletion in both HEK293T and K-562 cell lines. FIG. 2C shows exemplary DNA sequence modification arising from CRISPR-mediated cleavage and repair by NHEJ at the individual site targeted by the HPFH5-4 guide RNA in K562 cells.

FIG. 3A shows a schematic of PCR primer locations for detection of inversions and deletions of the 13 kb fragment. FIG. 3B shows inversion of genomic fragment between the cleavage sites (upper panel) or deletion of genomic fragment between respective cleavage sites (middle panel). Matrix showing the 5' and 3' guide RNA pairings used in each test sample (lower panel).

FIG. 4 shows sequence data obtained showing the deletions made using the HPFH5-4 and HPFH5-15 pair of guide RNAs. The PCR deletion product was TOPO®-cloned and 10 clones were sequenced. The new junctions created occur at the position corresponding to the position between the first A and T in the underlined portion of the sequence. Bold lettering indicates inserted nucleotide bases. Dots indicate deleted nucleotide bases.

FIG. 5 shows the quantitation of HPFH5 deletion allele generated using paired gRNAs. Combinations of gRNAs targeting both the 5' and 3' boundaries of the HPFH5 deletion were co-transfected into K562 and Hek293 cells. The frequency of the resulting deletion between the two cuts was measured using Droplet Digital PCR. In each case the 5' gRNA was HFPF5-4, while the 3' gRNA partner varied.

FIGS. 6A-B show a comparison of on-target and off-target site cleavage activity for the lead guide RNAs. FIG. 6A shows a sequence comparison of the highest scoring off-target (OT) sites as predicted by bioinformatics compared with the on-target (ON) site for guide RNAs HPFH5-4 and HPFH5-15. Sequences are shown 5' to 3', with the 3'-most triplet indicating the PAM sequence. Bolded letters indicate deviations from the on-target sequence. FIG. 6B shows the genome editing frequency at on-target (HPFH5-40N; HPFH5-150N) and predicted off-target sites as determined by deep sequencing.

FIGS. 7A-B show the gene editing efficiency of guide RNAs targeting sites throughout the length of the HPFH-5 13 kb deletion locus. FIG. 7A shows target sites and genomic locations of guide RNAs. FIG. 7B shows the genome editing efficiency of guide RNAs. Target sites are grouped into one kb increments of distance from the 5' boundary of the HPFH-5 deletion boundary.

FIG. 9 shows the sequences and genomic targets of guide RNAs for the HPFH Corfu deletions based on version hg38 of the human genome database.

FIG. 10A shows the Corfu 3.5 kb deletion (CS=Corfu 3.5 kb deletion). FIG. 10B shows the Corfu 7.5 kb deletion (CL=Corfu 7.5 kb deletion). FIG. 10C shows the relative distribution of guide RNAs at the 5' and 3' boundaries of the deletions (CS=Corfu 3.5 kb deletion, CL=Corfu 7.5 kb deletion).

FIG. 11A shows the Corfu 3.5 kb deletion (CS=Corfu 3.5 kb deletion). FIG. 11B shows the Corfu 7.5 kb deletion (CL=Corfu 7.5 kb deletion). FIG. 11C shows the relative distribution of guide RNAs at the 5' and 3' boundaries of the deletions (CS=Corfu 3.5 kb deletion, CL=Corfu 7.5 kb deletion).

FIG. 12A shows that PCR products detect deletion (left panel) and inversion (right panel) of the Corfu 7.5 kb and 3.5 kb regions. FIG. 12B shows a matrix showing the 5' and 3' guide RNA pairings used in the lanes depicted. Location of target sequences is shown in FIG. 11C.

FIG. 13A shows a schematic of the β-globin locus showing the location of the guide RNAs (left box, guides 1-8) and 3' (right box, guides 9-17). FIG. 13B shows the sequence and genomic location of the guide RNAs targeting each boundary of the HPFH Kenya deletion. FIG. 13C shows the genome modification activity of the guide RNAs as determined by T7E1 assay. Note: in some gel lanes a high level of background banding was present that contributed to the measured indel frequency. The white line through the data indicated the estimated level of signal associated with this background.

FIGS. 14A-D show the location of guide RNAs for the HPFH-SD 13 bp deletion. FIG. 14A shows the sequence alignment of wild type and 13 bp deletion variant of human γ-globin locus. Potential PAM sites for CRISPR are circled. FIG. 14B shows the location of guide RNAs (arrows). Also shown is the location of the 13 bp deletion sequence as well as the two repeat sequences predicted to mediate the microhomology-driven NHEJ event that results in the 13 bp deletion. FIG. 14C shows the sequence and genomic location of the guide RNAs designed to create the HPFH-SD deletion. FIG. 14D shows the sequence alignment of HBG1 and HBG2 genes showing the conserved target region (dotted box), along with the potential ~5 kb deletion arising from cleavage at the target site in both genes (lower panel).

FIGS. 15A-C show the analysis of DNA repair events at the HPFH-SD target site in Hek293 cells. FIG. 15A shows the sequence analysis of the DNA repair events detected following cleavage with different guide RNAs. The frequency of deletion (−ve X-axis) and insertion (+ve X-axis) events are quantified for each guide RNA. FIG. 15B shows a summary of distribution of repair outcomes for the guide SD2 indicating that the desired 13 bp deletion occurs with a frequency of 9.3%. FIG. 15C shows the sequence of NHEJ-mediated DNA repair events detected other than the 13 bp deletion. Underlining shows the repeat sequences. The location of 13 bp deletion is also shown.

FIGS. 16A-C show other deletion and non-deletion modifications of the β-globin locus associated with HPFH. FIG. 16A shows a schematic showing location of HPFH-4 deletion. FIG. 16B shows a schematic showing location of the HPFH Black deletion. FIG. 16C shows a genomic sequence in the region of the $^G\gamma$-175(T to C) mutation. Potential PAM sites for *S. pyogenes* Cas9 are circled. Nucleotide T175 is shown in bold.

DETAILED DESCRIPTION

Hemoglobinopathies

Figure 1A:
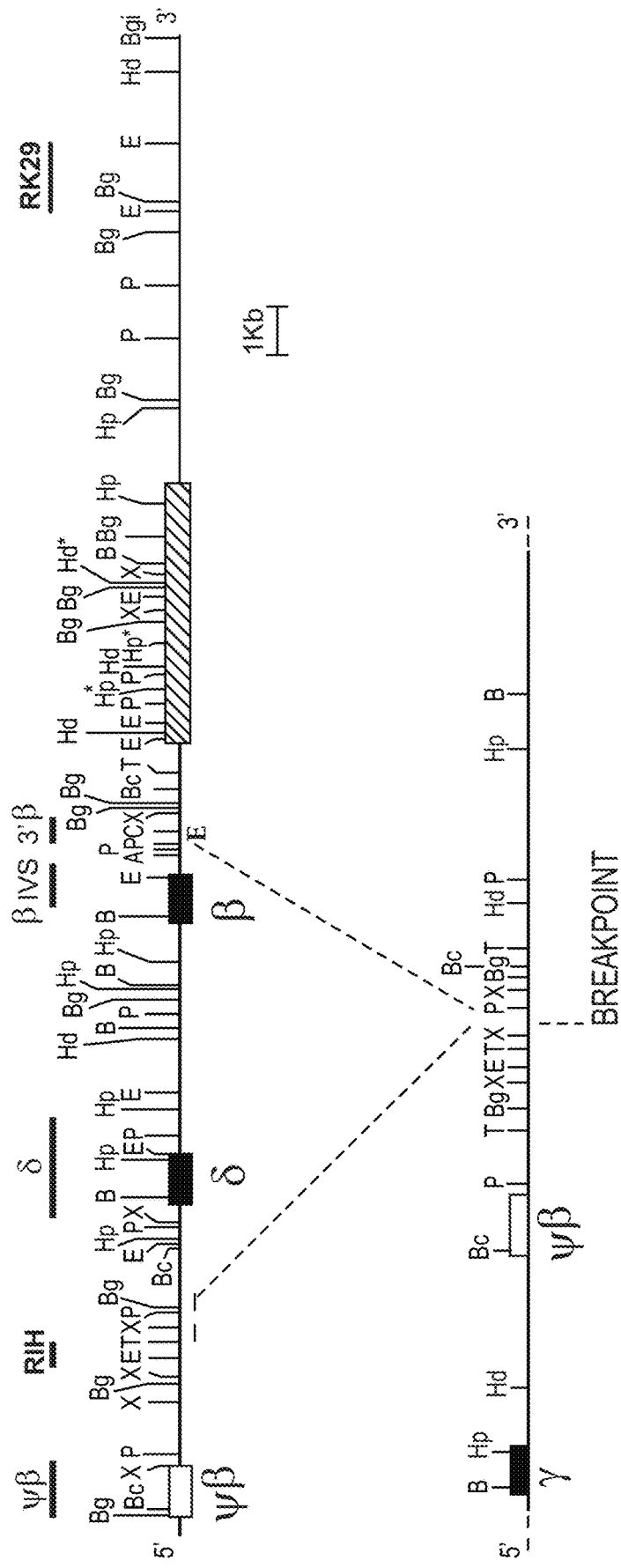

Fetal hemoglobin (HbF) is a tetramer of two adult α-globin polypeptides and two fetal β-like γ-globin polypeptides. The γ-globin genes (HBG1 and HBG2) are normally expressed in the fetal liver, spleen and bone marrow. A tetramer of two γ-chains together with two α-chains constitute HbF. During gestation, the duplicated γ-globin genes constitute the predominant genes transcribed from the β-globin locus. Following birth, γ-globin becomes progressively replaced by adult β-globin, a process referred to as the "fetal switch." This developmental switch from production of predominantly HbF (α2γ2) to production of adult hemoglobin or HbA (α2β2) begins at about 28 to 34 weeks of gestation and continues shortly after birth at which point HbA becomes predominant. The switch results primarily from decreased transcription of the γ-globin genes and increased transcription of β-globin genes. On average, the blood of a normal adult contains only about 2% of total hemoglobin in the form of HbF, though residual HbF levels have a variance of over 20 fold in healthy adults (Atweh, Semin. Hematol. 38(4):367-73 (2001)). The two types of γ-chains differ at residue 136 where glycine is found in the G-γ-product (HBG2) and alanine is found in the A-γ-product (HBG1). The HBG1 hemoglobin gene ($^A$γ or A-gamma [*Homo sapiens* (human)] Gene ID: 3047), was updated on 16 Apr. 2014 (www dot ncbi dot nlm dot nih dot gov/gene/3047).

As used herein, the term "hemoglobinopathy" means any defect in the structure, function or expression of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term further includes any decrease in the amount or effectiveness of hemoglobin, whether normal or abnormal, caused by external factors such as disease, chemotherapy, toxins, poisons, or the like. β-hemoglobinopathies contemplated herein include, but are not limited to, sickle cell disease (SCD, also referred to a sickle cell anemia or SCA), sickle cell trait, hemoglobin C disease, hemoglobin C trait, hemoglobin S/C disease, hemoglobin D disease, hemoglobin E disease, thalassemias, hemoglobins with increased oxygen affinity, hemoglobins with decreased oxygen affinity, unstable hemoglobin disease and methemoglobinemia.

The potential for addressing β-hemoglobinopathies by increasing levels of fetal hemoglobin ($α_2γ_2$; HbF) is supported by observations of the mild phenotype of individuals who have co-inherited homozygous β-thalassemia and hereditary persistence of fetal hemoglobin (HPFH), as well as by those patients with homozygous β-thalassemia who synthesize no adult hemoglobin, but in whom a reduced requirement for transfusions is observed in the presence of increased concentrations of HbF. Additional support comes from the observation that certain populations of adult patients with β chain abnormalities have higher than normal levels of HbF, and have been observed to have a milder clinical course of disease than patients with normal adult levels of HbF. For example, a group of Saudi Arabian sickle-cell anemia patients who express 20-30% HbF (as a percent of total hemoglobin) have only mild clinical manifestations of the disease [Pembrey et al., *Br. J. Haematol.* 40: 415-429 (1978)]. It is now accepted that β-hemoglobinopathies, such as sickle cell anemia and the β-thalassemias, are ameliorated by increased HbF production. [Reviewed in Jane and Cunningham, *Br. J. Haematol.* 102: 415-422 (1998) and Bunn, *N. Engl. J. Med.* 328: 129-131 (1993)].

The human β-globin locus is composed of five β-like genes and one pseudo-β gene located on a short region of chromosome 11 (approximately 45 kb), responsible for the creation of the β chains of hemoglobin. Expression of all of these genes is controlled by single locus control region (LCR), and the genes are differentially expressed throughout development. The order of the LCR and genes in the β-globin cluster, as illustrated in FIG. 1B, is as follows: 5'-[LCR]ε (epsilon, HBE1)-Gγ (G-gamma, HBG1)-Aγ (A-gamma, HBG2)-[ψβ (psi-beta pseudogene)]-δ (delta, HBD)-β (beta, HBB)-3'.

The arrangement of the five β-like genes reflects the temporal differentiation of their expression during development, with the early-embryonic stage version HbE (encoded by the epsilon gene) being located closest to the LCR, followed by the fetal version HbF (encoded by the γ genes), the delta version, which begins shortly prior to birth and is expressed at low levels in adults as HbA-2 (constituting approximately 3% of adult hemoglobin in normal adults), and finally the beta gene, which encodes the predominant adult version HbA-1 (constituting the remaining 97% of HbA in normal adults).

Expression of the β-like genes is regulated in embryonic erythropoiesis by many transcription factors, including KLF1, which is associated with the upregulation of HbA in adult definitive erythrocytes, and KLF2, which is associated with the expression of embryonic hemoglobin. BCL11A is activated by KLF1 and is likewise known to be involved in the switch from fetal to adult hemoglobin. Down-regulation of BCL11A expression or disruption of its activity or binding to transcriptional regulatory sites has been a focus of long-terms efforts from various groups to increase levels of HbF. See, e.g., U.S. Pat. No. 8,383,604, US2014085593, US20140093913, and references cited therein.

Certain naturally-occurring genetic mutations within the human β-globin locus are associated with de-repression of γ-globin gene expression and the clinical manifestation of HPFH. Such mutations range from single base substitutions associated with various forms of non-deletional HFPF, to deletions spanning tens of kb in the case of some forms of deletional HPFH. A variety of naturally-occurring HPFHs were described in *A Syllabus of Thalassemia Mutations* (1997) by Titus H. J. Huisman, Marianne F. H. Carver, and Erol Baysal, published by The Sickle Cell Anemia Foundation in Augusta, GA, USA, and references cited therein, including both deletional and non-deletional types.

A number of different forms of deletional HPFH have been reported based on studies from individuals and families found to have deletions in a region referred to herein as the "δβ-globin region" which extends from the psi-beta pseudogene through delta, beta and the region downstream of beta that is deleted in the larger HPFH alleles such as HPFH-1, as described in the art.

In some cases of HPFH, nearly all of the hemoglobin produced is HbF. However, in most cases, HbF ranges from approximately 15-30% of total hemoglobin depending on the type of HPFH as well as variation among individuals. Deletions Disrupting or Eliminating the β-Globin Gene and Advantages of Such Deletions in Treating SCD In certain embodiments as described and illustrated herein, in addition to increasing expression of the γ-globin gene product HbF, expression of the β-globin gene product is substantially reduced or eliminated by disruption or elimination of the β-globin gene in connection with the genome editing procedure. This occurs when the genome editing uses DNA endonuclease to effect a pair of DSBs, the first at a 5' DSB locus and the second at a 3' DSB locus within the δβ-globin region of human chromosome 11, causing a deletion of the chromosomal DNA between the 5' DSB locus and the 3' DSB locus that results in increased expression of γ-globin, the deletion also removes all or a portion of the β-globin gene (HBB) causing a concomitant decrease in expression of or elimination of the β-globin gene product, thereby resulting in a combination of (i) increasing the level of HbF in the cell, and (ii) reducing or eliminating expression of the β-globin gene product from at least one HBB allele on chromosome 11.

The combined effects of increased HbF and reduced or eliminated β-globin gene expression has particular additional advantages in the context of ameliorating hemoglobinopathies such as SCD in which the product of the variant β-globin allele (i.e. HbS) is harmful to cells expressing it, causing premature cell death (as well as other negative effects associated with HbS). Thus, not only do sickled RBCs cause multiple problems for patients, as discussed above and in the art, but sickled RBCs have a substantially reduced life span relative to normal RBCs. The presence of HbS and sickled RBCs also leads to numerous other negative effects as described herein and in the art.

In the case of embodiments in which the β-globin gene is effectively disrupted or eliminated as described herein, even "knocking down" (reducing) or "knocking out" (eliminating) only one of the β-globin alleles expressing HbS, e.g., by successfully editing only one of the two copies of the gene in homozygous SCD patients (who have two defective β-globin alleles, one on each copy of chromosome 11) can have a very substantial benefit. In particular, increasing levels of HbF to the range of about 20% is considered to substantially eliminate sickling. However, as a relatively continuous or incremental factor (often referred to as a "quantitative trait") over a significant range, even lower levels HbF can have significant beneficial effects as described herein and in the art. In these embodiments, therefore, even though the SCD patient has two defective β-globin alleles, the combination of increasing HbF (which is itself helpful for reducing the effects of SCD) along with reducing HbS (which is itself a driver of many of the deleterious effects in a quantitative manner), by genome editing using the method described and illustrated for these embodiments can bring about a combination of effects that together ameliorate one of more symptoms of the disease.

In some cases, the genome editing procedure can effectively alter both copies of an allele. Such bi-allelic editing can in some cases be screened for or selected for, but even if not selected for it can naturally occur, albeit at lower frequency as compared to mono-allelic or single allele hits, since the same target site generally exists on each member of the pairs of chromosomes.

For technical reasons as noted above, however, embodiments as described and illustrated herein in which only one of the β-globin alleles is disrupted or eliminated—in addition to increasing levels of HbF—would be expected to have significant positive effects in ameliorating one or more symptoms or conditions associated with SCD.

The ability to generate these significant "cis-type" (on the same allele) effects using the types of genome editing reflected in such embodiments can be more advantageous than approaches depending on "trans-type" effects such as those involving knock out or knock down or a trans-acting factor such as a repressor. In particular, as noted above, the genome editing in embodiments in which the β-globin gene is effectively disrupted or eliminated can substantially ameliorate effects of HbS by successfully editing on one of the two alleles. In the case of trans-acting repressors, such as a repressor of γ-globin gene expression, knocking down or knocking out one copy of the repressor gene may not be sufficient since expression of the repressor from the other copy of the gene can still reduce γ-globin gene expression limiting the levels of HbF that might be achieved.

Effects of Increased of HbF in the Context of β-Thalassemia

As noted above, β-thalassemias result from a partial or complete defect in the expression of the β-globin gene, leading to deficient or absent hemoglobin A (HbA). Since there is no production of HbS, RBCs in β-thal patients do not exhibit the sickling and associated problems associated with SCD. However, a different sort of RBC 'toxicity' and premature cell death occurs as a result of the lack of HbA in the context of β-thal. In particular, the excess of unpaired alpha globin (α-globin) chains in β thalassemia interact with the red cell (RBC) membrane, causing oxidative damage to membrane skeletal components, and potentially other components. This interaction results in a rigid, mechanically unstable membrane that causes increased apoptosis (i.e. programmed cell death) and shortened RBC survival, marked by ineffective erythropoiesis and anemia.

Increasing the levels of HbF in RBCs of such patients can significantly ameliorate one or more symptoms of β-thalassemia because the beta-chains produced by increasing γ-globin gene expression can pair with the previously unpaired alpha-chains to produce HbF, which not only results in a functioning hemoglobin tetramer but concomitantly reduces the levels of unpaired α-globin chains that are a contributing cause of the β-thalassemia condition because of premature RBC cell death.

Positive Selective Advantages of Certain Edited Cells

In connection with the foregoing advantages provided in certain embodiments of the invention, in particular the advantages in terms of RBC survival for sickle cell RBCs that can be mediated by genome editing that not only increases levels of HbF but reduces levels of HbS, and the advantages in terms of RBC survival for β-thal RBCs that not only increases levels of HbF but reduces levels of unpaired alpha-chains, cells that are modified by such genome editing techniques as described and illustrated herein will have selective advantages relative to the population of diseased RBCs into which they may be introduced, e.g., by gene editing a patients' own HSC's or erythroid progenitor cells ex vivo and then reintroducing such cells to the patient, where reintroduced cells must generally successfully persist or "engraft" in order for beneficial effects to be sufficient and sustained.

As a result of the foregoing selective advantages, the introduction of even modest numbers of suitable stem cells edited as described herein would be expected over time to result in improved cells representing a significantly higher fraction of the overall population of RBCs than they were initially following introduction into a patient. By way of illustration, with successfully gene edited stem cells representing as few as several percent of corresponding cells initially (i.e. compared to the population of resident cells that carry the unedited hemoglobinopathy-associated alleles), the gene edited cells could come to represent a majority of cells as a result of selective survival advantages conveyed upon them through use of gene editing techniques as described further herein. The eventual numbers reflecting such positively selected engraftment will vary depending generally on both the degree to which the resident diseased cells exhibit reduced lifespan in a given patient, and the relative survival advantage exhibited by the gene edited cells. However, as noted above, the diseased cells associated with SCD and β-thalassemia have significantly reduced lifespans (due to the presence of HbS and unpaired alpha-chains respectively), and certain embodiments not only increase levels of HbF but reduce the levels of HbS (associated with SCD) or reduce the levels of unpaired alpha-chains (associated with β-thalassemia), and therefore the relative survival benefits and with them increased engraftment, are expected to be significant.

Corfu and Corfu-Like Deletions

Although the Corfu chromosomal allele first discovered in a Greek child results in a δβ-thalassemia, it shares some important characteristics with various deletional forms of HPFH, in particular increased levels of HbF, and therefore the deletion associated with Corfu is included with deletional HPFH forms as described herein.

However, Corfu is different from forms of deletional HPFH in terms of HbF levels and β-globin expression. Extremely high levels of HbF are associated with Corfu, approaching 100% of total hemoglobin in the case of the first child identified—and this was particularly surprising because Corfu heterozygotes (the child's parents in the first case) were found to have only normal very low levels of HbF (1-2% of total hemoglobin)—a situation that's been referred to by hematologists as the "Corfu Paradox."

A putative explanation is that the Corfu chromosomal allele was found to contain a splice site mutation in IVS-I position 5 ("IVS-I-5") of the β-globin gene and lower levels of the β-globin gene transcript. It has been reported that the high levels of HbF observed are contributed to post-transcriptionally by enhanced mRNA maturation and/or stabilization of the γ-globin transcript, which is apparently associated with the reduced levels of β-globin mRNA; see, e.g., Chakalova, L. et al., *Blood* 105: 2154-2160 (2005).

Since the Corfu chromosomal allele contains both the large deletion and the IVS-I-5 mutation, and reduced levels of β-globin mRNA associated with the latter are believed to independently contribute to the unusually high levels of HbF produced, the IVS-I-5 "Corfu-related β-globin mutation" could be used alone or in combination with other gene edited alterations as described herein in order to increase HbF levels for use in ameliorating hemoglobinopathies.

Target Sequence Selection

For the amelioration of hemoglobinopathies via gene editing, as described herein, it is desirable but not necessary to achieve levels of HbF at the high end of those observed in naturally-occurring cases in order to bring about relative improvements in the disease. In particular, while it had originally been assumed that relatively high levels of HbF were essential for ameliorative effects to be observed, especially with respect to certain complications, studies have shown that even small incremental increases of HbF can have beneficial effects on mortality. See, e.g., Powars et al., *Blood* 63(4):921-926 (1984); Platt et al., *N Engl J Med* 330(23):1639-1644 (1994); and Akinsheye et al., *Blood* 118: 19-27 (2011).

One reason for the beneficial effects of even low levels of HbF in the context of sickle cell disease, is that even small incremental increases in HbF have been shown to have some beneficial effects, and levels of less than 9% of HbF (relative to total hemoglobin, Hb) appear to be associated with significantly decreased mortality; see, e.g., Platt et al., supra.

Higher levels of HbF are associated with additional clinical benefits and further decreases in morbidity and mortality, as observed in the case of SCD co-inherited with certain naturally-occurring HPFH alleles and/or Corfu thalassemia alleles, in which HbF levels in the 20-30% range have been associated with very substantial to nearly complete normalization of the SCD phenotype.

Genetic modifications within the δβ-globin region that are contemplated for increasing HbF expression to ameliorate a hemoglobinopathy as described herein result in at least about 5%, at least about 9%, at least about 14%, at least about 20 at least about 25%, or above 30% HbF (relative to total Hb in a subject).

As described and illustrated further herein, exemplary genetic modifications within the δβ-globin region that are contemplated for increasing HbF expression to such levels include, but are not limited to, the following deletions, as well as variations thereof in which the size of the deletion is reduced (e.g. by shifting the 5' boundary of the deletion specified below further toward the 3' boundary of the deletion specified below or shifting the 3' boundary of the deletion further toward the 5' boundary) or increased (by shifting either boundary in the opposite direction). Deletions made by other combinations of two of the following deletion boundaries that increase HbF expression are also specifically contemplated by the disclosure.

A. Deletions in chromosome 11 within the region Chr11: 5224779-5237723 based on the GRCh38/hg38 version of the human genome assembly, wherein the 3' boundary of the deletion is proximal (as defined below) to Chr11:5224779 and the 5' boundary of the deletion is proximal to Chr11: 5237723;

B. Deletions in chromosome 11 within region Chr11: 5234665-5238138 based on the GRCh38/hg38 version of the human genome assembly, wherein the 3' boundary of the deletion is proximal to Chr11:5234665 and the 5' boundary of the deletion is proximal to Chr11:5238138;

C. Deletions in chromosome 11 within region Chr11: 5233055-5240389 based on the GRCh38/hg38 version of the human genome assembly, wherein the 3' boundary of the deletion is proximal to Chr11:5233055 and the 5' boundary of the deletion is proximal to Chr11:5240389;

D. Deletions in chromosome 11 within region Chr11: 5226631-5249422 based on the GRCh38/hg38 version of the human genome assembly, wherein the 3' boundary of the deletion is proximal to Chr11:5226631 and the 5' boundary of the deletion is proximal to Chr11:5249422;

E. Deletions in chromosome 11 within region Chr11: 5249959-5249971 based on the GRCh38/hg38 version of the human genome assembly wherein the 3' boundary of the deletion is at or adjacent to Chr11:5249959 and the 5' boundary of the deletion is at or adjacent to Chr11:5249971;

F. Deletions in chromosome 11 within region Chr11: 5196709-5239223 based on the GRCh38/hg38 version of the human genome assembly, wherein the 3' boundary of the deletion is proximal to Chr11:5196709 and the 5' boundary of the deletion is proximal to Chr11:5239223;

G. Deletions in chromosome 11 within region Chr11: 5225700-5236750 based on the GRCh38/hg38 version of the human genome assembly, wherein the 3' boundary of the deletion is proximal to Chr11:5225700 and the 5' boundary of the deletion is proximal to Chr11:5236750;

H. Deletions in chromosome 11 within region Chr11: 5234655-5238138 based on the GRCh38/hg38 version of the human genome assembly, wherein the 3' boundary of the deletion is proximal to Chr11:5234655 and the 5' boundary of the deletion is proximal to Chr11:5238138;

I. Deletions in chromosome 11 within region Chr11: 5255885-5259368 based on the GRCh37/hg19 version of the human genome assembly, wherein the 3' boundary of the deletion is proximal to Chr11:5255885 and the 5' boundary of the deletion is proximal to Chr11:5259368.

In another aspect, provided herein are methods of increasing the level of fetal hemoglobin (HbF) in a human cell by genome editing using DNA endonuclease to effect a double-strand break (DSB) positioned at one or more loci within the β-globin region of human chromosome 11, wherein at least one DSB is positioned within the γ-globin regulatory region of human chromosome 11, which is located within a region less than 2 kb, less than 1 kb, less than 0.5 kb, or less than 0.25 kb upstream of the start of one of the γ-globin genes (HBG1 or HBG2), causing deletions or insertions of chromosomal DNA at the one or more loci that results in increased expression of γ-globin, thereby increasing the level of HbF in the cell. In another type of method exemplifying this aspect, at least one DSB is positioned within the δβ-globin region of human chromosome 11.

Illustrative modifications in chromosome 11 in the γ-globin regulatory region include the creation of single base substitutions such as −175 (T to C), −202 (C to G), and −114 (C to T) in the $^G\gamma$ gene; and −196 (C to T), −175 (T to C), −117 (G to A) in the $^A\gamma$ gene.

Illustrative modifications within the δβ-globin region include deletions and insertions within or proximal to the HPFH deletion loci referred to above, and deletions within the δ-globin regulatory region of human chromosome 11 which is located within the region of less than 3 kb, less than 2 kb, less than 1 kb, less than 0.5 kb upstream of the start of the δ-globin gene (HBD), and deletions within the β-globin regulatory region of human chromosome 11, which is located within the region of less than 3 kb, less than 2 kb, and less than 1 kb, or less than 0.5 kb upstream of the start of the β-globin gene (HBB).

Given the relatively wide variations in deletions that are associated with various forms of HPFH, coupled with the fact that even low levels of HbF can provide significant levels of amelioration of hemoglobinopathy (as noted above), and the understanding from a variety of studies that there appear to be multiple loci and types of controls that can contribute to repression of HbF, it will be appreciated that numerous variations of the deletions referenced above (including without limitation larger as well as smaller deletions), would be expected to result in levels of HbF that are within the contemplated ranges, as noted above.

Such variants include deletions that are larger in the 5' and/or 3' direction than naturally-occurring HPFH deletions, or smaller in either direction. Accordingly, by "proximal" with respect to HPFH-like deletions, it is intended that the DSB locus associated with a desired deletion boundary (also referred to herein as an endpoint) may be within a region that is less than about 3 kb from the reference locus noted. In some embodiments, the DSB locus is more proximal and within 2 kb, within 1 kb, within 0.5 kb, or within 0.1 kb. In the case of small deletions such as that identified in group E, the desired endpoint is at or "adjacent to" the reference locus, by which it is intended that the endpoint is within 100 bp, within 50 bp, within 25 bp, or less than about 10 bp to 5 bp from the reference locus.

A group of embodiments comprise deletions within the "δ-region" (which includes the downstream half of the intergenic sequence between the ψβ1 pseudogene and the δ gene HBD, and proximal sequences downstream sequences in the δ). The δ-proximal-region appears to include a number of elements associated with repression of γ-globin. The 7.2 kb "Large Corfu" δβ thalassemia deletion described and exemplified further herein falls within the δ-region, deleting approximately 1 kb of the δ gene and 6 kb upstream, and is associated with a significant increase in levels of HbF. A 3.5 "Small Corfu" deletion, described further and illustrated herein, likewise has a deletion in the δ-region, and is also associated with increased levels of HbF. The δ-region is also deleted in all major forms of HPFH.

With respect to regions further downstream in the 3' direction, which would be associated with larger deletions as described herein, HPFH-1 through HPFH-5 all have the δ and β genes deleted. Besides regulatory elements in the δ-region that may contribute to active repression of γ-globin, activity of the δ and β promoters may also indirectly contribute to suppression via competition for transcriptional factors required for γ-globin expression.

Many HPFH types also have even larger deletions extending further downstream, and these additional downstream regions can also be incorporated into deletions as described and illustrated herein, since they are known to be associated with substantial increases of HbF, well above the ranges of HbF known to ameliorate hemoglobinopathies as noted above.

One advantage for patients with hemoglobinopathies of replicating or mimicking aspects of deletions that are found naturally in individuals with HPFH is that such deletions are already known to be both safe and associated with the amelioration of hemoglobinopathy. However, among deletional HPFH, it is also clear that smaller deletions such as HPFH-5 are effective for generating substantial increases in HbF. Other embodiments comprising smaller deletions are expected to provide substantial increases, and as noted above, even modest levels of increase of HbF have beneficial effects. It is thus expected that many variations of the deletions described and illustrated herein will be effective for ameliorating hemoglobinopathies.

Preferentially, shifts in the location of the 5' boundary and/or the 3' boundary relative to particular reference loci are used to facilitate or enhance particular applications of gene editing, which depend in part on the endonuclease system selected for the editing, as further described and illustrated herein. In a first aspect of such target sequence selection, many endonuclease systems have rules or criteria that guide the initial selection of potential target sites for cleavage, such as the requirement of a PAM sequence motif in a particular position adjacent to the DNA cleavage sites in the case of Crispr Type II endonucleases.

In another aspect of target sequence selection or optimization, the frequency of "off-target" activity for a particular combination of target sequence and gene editing endonuclease (i.e. the frequency of DSBs occurring at sites other than the selected target sequence) is assessed relative to the frequency of on-target activity. In some cases, cells that have been correctly edited at the desired locus may have a selective advantage relative to other cells. Illustrative but nonlimiting examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus may be positively selected for by one or more screening methods used to identify, sort or otherwise select for cells that have been correctly edited. Both selective advantage and directed selection methods may take advantage of the phenotype associated with the correction.

Whether or not any selective advantage is applicable or any directed selection is to be applied in a particular case, target sequence selection is can also be guided by consideration of off-target frequencies in order to enhance the effectiveness of the application and/or reduce the potential for undesired alterations at sites other than the desired target. As described further and illustrated herein and in the art, the occurrence of off-target activity is influenced by a number of factors including similarities and dissimilarities between the target site and various off target sites, as well as the particular endonuclease used. In many cases, bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein and others are known in the art.

Another aspect of target sequence selection relates to homologous recombination events. It is well known that sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs) which occur on a regular basis during the normal cycle but may also be enhanced by the occurrence of various events (such as UV light and other inducers of DNA breakage) or the presence of certain agents (such as various chemical inducers). Many such inducers cause DSBs to occur indiscriminately in the genome, and DSBs are regularly being induced and repaired in normal cells. During repair, the original sequence may be reconstructed with complete fidelity, however, in some cases, small insertions or deletions (referred to as "indels") are introduced at the DSB site.

DSBs may also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems such as Crispr in which homology directed repair (HDR) is used to insert a sequence of interest, provided through use of a "donor" polynucleotide, into a desired chromosomal location.

Figure 14A:
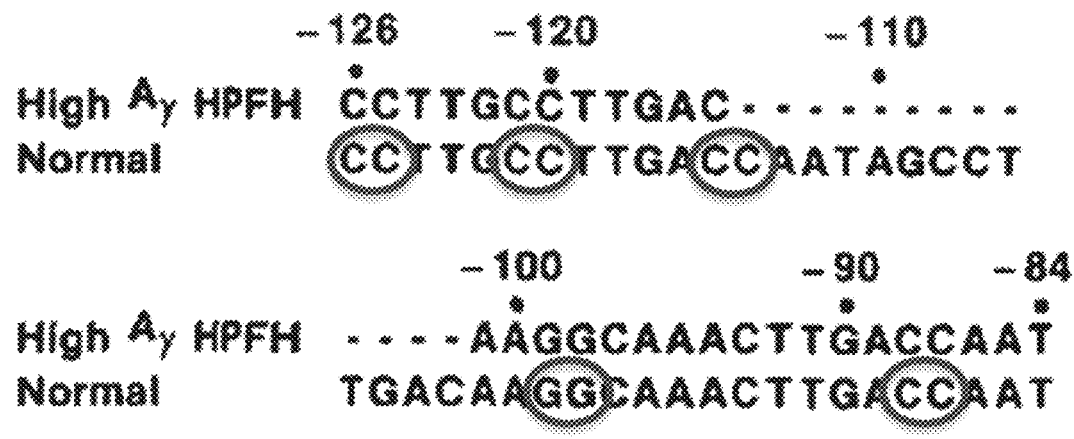
Figure 14B:
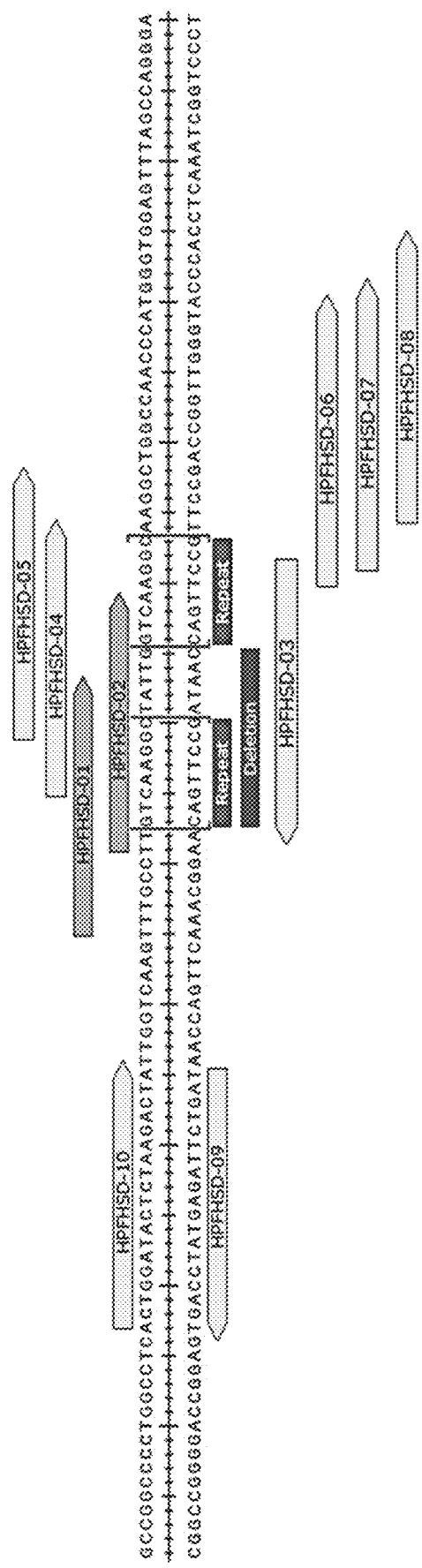

Regions of homology between particular sequences, which can be small regions of "microhomology" that may comprise as few as ten basepairs or less, can also be used to bring about desired deletions. For example, in the case of the so-called "small deletion" exemplified herein, a single DSB is introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process. In the case of this small deletion, which is in the upstream region of the γ-globin gene as illustrated in FIG. 14B, the result of the deletion is to increase levels of HbF, apparently through disruption of a gene silencing sequence.

Figure 14D:
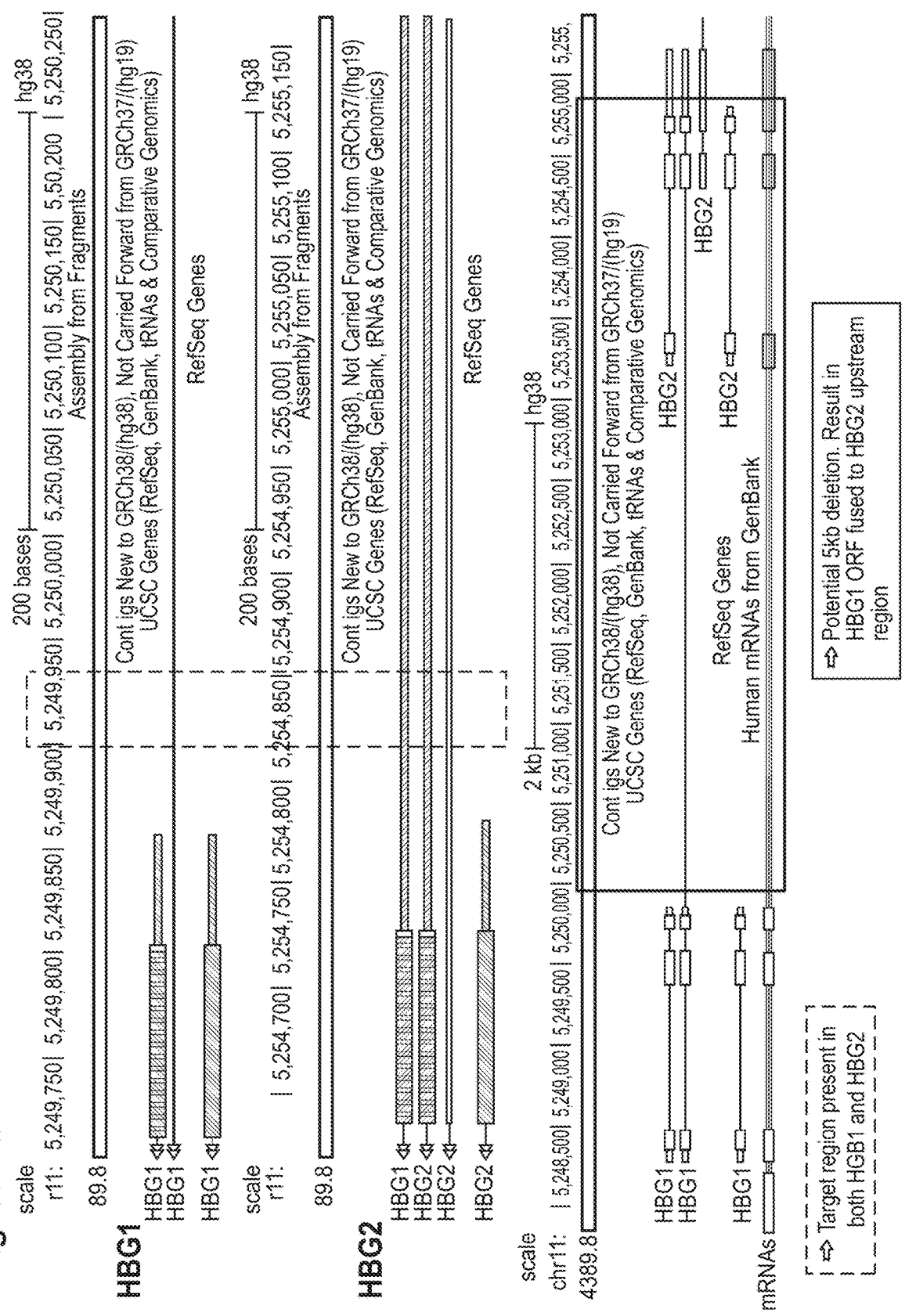

In some circumstances, however, selecting target sequences within regions of homology can also give rise to much larger deletions including gene fusions (when the deletions are in coding regions), which may or may not be desired given the particular circumstances. For example, as illustrated in FIG. 14D, the homologies that exist between the two closely-related γ-globin genes HBG1 and HBG2 can give rise to large deletions arising through homologous recombination between more distal sites of homology.

The examples provided herein further illustrate the selection of various target regions for the creation of DSBs designed to induce deletions that result in the increase of HbF levels in human cells, as well as the selection of specific target sequences within such regions that are designed to minimize off-target events relative to on-target events.

Human Cells

For ameliorating hemoglobinopathies, as described and illustrated herein, the principal targets for gene editing will be human cells which, after being modified using the techniques as described, can give rise to red blood cells (RBCs) with increased levels of HbF in a patient suffering from a hemoglobinopathy such as β-thalassemia or sickle cell disease.

As described herein and in the art, even relatively modest and incremental increases in levels of HbF in a patient suffering from a hemoglobinopathy such as β-thalassemia or sickle cell disease can be beneficial for improvement of symptoms and/or survival. In some embodiments, the levels of HbF achieved will tend toward those observed in patients with HPFH, which vary among patients and type of HPFH but in a substantial number of cases result in HbF comprising in the range of 10-30% of total hemoglobin (versus 1-2% in typical adults). However, studies have shown that lower levels of HbF can nevertheless have effects that are significant enough to be regarded as decreasing overall mortality expectations among groups of patients with SCD; see, e.g., Platt et al., *N Engl J Med.* 330(23): 1639-1644 (1994). And even modest improvements of symptoms can have beneficial effects for patients. For example, a reduction in the need for transfusions, a lessening of the incidence or severity of one or more symptoms of a hemoglobinopathy, or a reduction of side effects as a result of reduced levels or frequency of treatments or procedures can all be meaningful and beneficial for patients. Accordingly, in some embodiments, the increase in HbF may be in the range of about 80%, 60%, 40% or 20% of the levels of HbF observed in patients with HPFH. Further considerations regarding levels of HbF that may be achieved are provided herein, including the detailed description and examples, as supplemented by references cited herein and/or published in the art.

By performing gene editing as described herein in progenitor cells such as erythroid progenitor cells, such as autologous progenitor cells that are derived from and therefore already completely matched with the patient in need, it is possible to generate cells that can be safely reintroduced into a patient and effectively give rise to a population of circulating RBCs that will be effective in ameliorating one or more clinical conditions associated with the patient's disease.

While the presence of significant numbers of RBCs having elevated levels of HbF is beneficial, in some embodiments more than one quarter of circulating red blood cells (RBCs) will have significantly elevated levels of HbF, in some embodiments at least half of circulating RBCs will have significantly elevated levels of HbF, and in some embodiments at least 80% of circulating RBCs will have significantly elevated levels of HbF in order to effectively prevent clinical erythrocyte sickling.

Progenitor cells (also referred to as stem cells herein), such as erythroid or hematopoietic progenitor cells, are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness."

Self-renewal is another important aspect of the stem cell, as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate to lineage-restricted precursor cells (such as a hematopoietic progenitor cell), which in turn can differentiate into other types of precursor cells further down the pathway (such as an erythrocyte precursor), and then to an end-stage differentiated cell, such as an erythrocyte, which plays a characteristic role in a certain tissue type, and may or may not retain the capacity to proliferate further.

"Hematopoietic progenitor cell" as the term is used herein, refers to cells of a stem cell lineage that give rise to all the blood cell types including the erythroid (erythrocytes or red blood cells (RBCs)), myeloid (monocytes and macrophages, neutrophils, basophils, eosinophils, megakaryocytes/platelets, and dendritic cells), and lymphoid (T-cells, B-cells, NK-cells).

A "cell of the erythroid lineage" indicates that the cell being contacted is a cell that undergoes erythropoiesis such that upon final differentiation it forms an erythrocyte or red blood cell. Such cells originate from bone marrow hematopoietic progenitor cells. Upon exposure to specific growth factors and other components of the hematopoietic microenvironment, hematopoietic progenitor cells can mature through a series of intermediate differentiation cellular types, all intermediates of the erythroid lineage, into RBCs. Thus, cells of the "erythroid lineage", as the term is used herein, comprise hematopoietic progenitor cells, rubriblasts, prorubricytes, erythroblasts, metarubricytes, reticulocytes, and erythrocytes.

In some embodiments, the hematopoietic progenitor cell has at least one of the cell surface marker characteristic of hematopoietic progenitor cells: CD34+, CD59+, Thy1/CD90+, CD38lo/−, and C-kit/CDI 17+. In some embodiments, the hematopoietic progenitor are CD34+.

In some embodiments, the hematopoietic progenitor cell is a peripheral blood stem cell obtained from the patient after the patient has been treated with granulocyte colony stimulating factor (optionally in combination with Plerixaflor). In illustrative embodiments, CD34+ cells are enriched using CliniMACS® Cell Selection System (Miltenyi Biotec). In some embodiments, CD34+ cells are weakly stimulated in serum-free medium (e.g., CellGrow SCGM media, CellGenix) with cytokines (e.g., SCF, rhTPO, rhFLT3) before genome editing. In some embodiments, addition of SR1 and dmPGE2 and/or other factors is contemplated to improve long-term engraftment.

In some embodiments, the hematopoietic progenitor cells of the erythroid lineage have the cell surface marker characteristic of the erythroid lineage: such as CD71 and Ter119.

Induced Pluripotent Stem Cells

In some embodiments, the genetically engineered human cells described herein are derived from induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a hematopoietic progenitor cell to be administered to the subject (e.g., autologous cells). Since the progenitors are essentially derived from an autologous source, the risk of engraftment rejection or allergic responses is reduced compared to the use of cells from another subject or group of subjects. In some embodiments, the hematopoietic progenitors are derived from non-autologous sources. In addition, the use of iPSCs negates the need for cells obtained from an embryonic source. Thus, in one embodiment, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a hematopoietic stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells is not critical to the claimed invention. Thus, any method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014); and references cited therein. The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes including, for example Oct-4 (also known as Oct-3/4 or Pouf51), Soxl, Sox2, Sox3, Sox 15, Sox 18, NANOG, Klfl, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (−)-Depudecin), HC Toxin, Nullscript (4-(I,3-Dioxo-IH,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., Cl-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9, 10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbxl5, Ecatl, Esgl, Eras, Gdf3, Fgf4, Cripto, Daxl, Zpf296, Slc2a3, Rexl, Utf1, and Natl. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Genome Editing

Genome editing generally refers to the process of modifying the nucleotide sequence of a genome, preferably in a precise or predetermined manner. Examples of methods of genome editing described herein include methods of using site-directed nucleases to cut DNA at precise target locations in the genome, thereby creating double-strand or single-strand DNA breaks at particular locations within the genome. Such breaks can be and regularly are repaired by natural, endogenous cellular processes such as homology-directed repair (HDR) and non-homologous end-joining (NHEJ), as recently reviewed in Cox et al., *Nature Medicine* 21(2), 121-31 (2015). NHEJ directly joins the DNA ends resulting from a double-strand break sometimes with the loss or addition of nucleotide sequence which may disrupt or enhance gene expression. HDR utilizes a homologous sequence, or donor sequence, as a template for inserting a defined DNA sequence at the break point. The homologous sequence may be in the endogenous genome, such as a sister chromatid. Alternatively, the donor may be an exogenous nucleic acid such as a plasmid, a single-strand oligonucleotide, a duplex oligonucleotide or a virus, that has regions of high homology with the nuclease-cleaved locus, but which may also contain additional sequence or sequence changes including deletions that can be incorporated into the cleaved target locus. A third repair mechanism is microhomology-mediated end joining (MMEJ), also referred to as "Alternative NHEJ, in which the genetic outcome is similar to NHEJ in that small deletions and insertions can occur at the cleavage site. MMEJ makes use of homologous sequences of a few basepairs flanking the DNA break site to drive a more favored DNA end joining repair outcome, and recent reports have further elucidated the molecular mechanism of this process; see, e.g., Cho and Greenberg, *Nature* 518, 174-76 (2015); Kent et al., *Nature Structural and Molecular Biology*, Adv. Online doi:10.1038/nsmb.2961(2015); Mateos-Gomez et al., *Nature* 518, 254-57 (2015); Ceccaldi et al., *Nature* 528, 258-62 (2015). In some instances it may be possible to predict likely repair outcomes based on analysis of potential microhomologies at the site of the DNA break.

Each of these genome editing mechanisms can be used to create desired genomic alterations. The first step in the genome editing process is to create typically one or two DNA breaks in the target locus as close as possible to the site of intended mutation. This can achieved via the use of targeted endonucleases, as described and illustrated herein.

Several distinct classes of nucleases have been engineered for use in genome editing. These include the zinc finger nucleases, transcription activator-like effector (TALE) nucleases, CRISPR/Cas nucleases, homing endonucleases (also termed meganucleases), and other nucleases; see, e.g., Hafez and Hausner, *Genome* 55, 553-69 (2012); Carroll, *Ann. Rev. Biochem.* 83, 409-39 (2014); Gupta and Musunuru, *J. Clin. Invest.* 124, 4154-61 (2014); and Cox et al., supra. These differ mainly in the way they bind DNA and create the targeted DNA double-strand (or single-strand) break (DSB). After creation of the DSB, essentially the same natural cellular DNA repair mechanisms of NHEJ or HDR are co-opted to achieve the desired genetic modification. Therefore, it is contemplated that genome editing technologies using any of these nucleases can be used to achieve genetic and therapeutic outcomes described herein.

Zinc Finger Nucleases

Zinc finger nucleases (ZFNs) are modular proteins comprised of an engineered zinc finger DNA binding domain linked to the catalytic domain of the type II endonuclease Fokl. Since Fokl functions only as a dimer, a pair of ZFNs must be engineered to bind to cognate target "half-site" sequences on opposite DNA strands and with precise spacing between them to enable the catalytically active Fokl dimer to form. Upon dimerization of the Fokl domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect then of ZFNs is that they can be readily retargeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the 5-7 bp spacer between half-sites. A target sequence of this length is likely to be unique in the human genome, assuming repetitive sequences or gene homologs are excluded during the design process. Nevertheless, the ZFN protein-DNA interactions are not absolute in their specificity and so off-target binding and cleavage events do occur, either as a heterodimer between the two ZFNs, or as a homodimer of one or other of the ZFNs. The latter possibility has been effectively eliminated by engineering the dimerization interface of the FokI domain to create "plus" and "minus" variants, also known as obligate heterodimer variants, which can only dimerize with each other and not with themselves. Forcing the obligate heterodimer prevents formation of the homodimer. This has greatly enhanced specificity of ZFNs as well as of any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., *Proc Natl Acad Sci USA* 96(6):2758-63 (1999); Dreier B et al., *J Mol Biol.* 303(4):489-502 (2000); Liu Q et al., *J Biol Chem.* 277(6):3850-6 (2002); Dreier et al., *J Biol Chem* 280(42): 35588-97 (2005); and Dreier et al., *J Biol Chem.* 276(31): 29466-78 (2001).

Transcription Activator-Like Effector Nucleases (TALENs)

TALENs represent another format of modular nucleases whereby, as with ZFNs, an engineered DNA binding domain is linked to the FokI nuclease domain, and a pair of TALENs operate in tandem to achieve targeted DNA cleavage. The major difference from ZFNs is the nature of the DNA binding domain and the associated target DNA sequence recognition properties. The TALEN DNA binding domain derives from TALE proteins originally described in the plant bacterial pathogen *Xanthomonas* sp. TALEs are comprised of tandem arrays of 33-35 amino acid repeats, with each repeat recognizing a single basepair in the target DNA sequence that is typically up to 20 bp in length, giving a total target sequence length of up to 40 bp. Nucleotide specificity of each repeat is determined by the repeat variable diresidue (RVD) which includes just two amino acids at positions 12 and 13. The bases guanine, adenine, cytosine and thymine are predominantly recognized by the four RVDs Asn-Asn, Asn-Ile, His-Asp and Asn-Gly, respectively. This constitutes a much simpler recognition code than for zinc fingers and thus represents an advantage over the latter for nuclease design. Nevertheless, as with ZFNs, the protein-DNA interactions of TALENs are not absolute in their specificity and TALENs have also benefitted from use of the obligate heterodimer variants of the FokI domain to reduce off-target activity.

Additional variants of the FokI domain have been created that are deactivated in their catalytic function. If one half of either a TALEN or a ZFN pair contains an inactive FokI domain then only single-strand DNA cleavage (nicking) will occur at the target site rather than a DSB. The outcome is comparable to the use of CRISPR/Cas9 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB which is prone to NHEJ-mediated mis-repair.

A variety of TALEN-based systems have been described in the art, and modifications thereof are regularly reported; see, e.g., Boch, *Science* 326(5959):1509-12 (2009); Mak et al., *Science* 335(6069):716-9 (2012); and Moscou et al., *Science* 326(5959):1501 (2009). The use of TALENs based on the "Golden Gate" platform has been described by multiple groups; see, e.g., Cermak et al., *Nucleic Acids Res.* 39(12):e82 (2011); Li et al., *Nucleic Acids Res.* 39(14):6315-25(2011); Weber et al., *PLoS One.* 6(2):e16765 (2011); Wang et al., *J Genet Genomics* 41(6):339-47, Epub 2014 May 17 (2014); and Cermak T et al., *Methods Mol Biol.* 1239:133-59 (2015).

Homing Endonucleases

Homing endonucleases (HE) are sequence-specific endonucleases that have long recognition sequences (14-44 base pairs) and cleave DNA with high specificity—often at sites unique in the genome. There are at least six known families of HE as classified by their structure, including LAGLIDADG (SEQ ID NO: 192), GIY-YIG, His-Cis box, H-N-H, PD-(D/E)xK, and Vsr-like that are derived from a broad range of hosts including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of the DNA, thereby functioning as site-specific nickases. The large target sequence of HEs and the specificity that offers has made them attractive candidates to create site-specific DSBs. However, a key difference with the modular ZFNs and TALENs, where the DNA binding and catalytic nuclease functions are structurally and functionally distinct, is that these functions in HEs are structurally integrated, thus making it particularly challenging to selectively alter the DNA binding specificity without negatively impacting binding affinity or catalytic function.

A variety of HE-based systems have been described in the art, and modifications thereof are regularly reported; see, e.g., the reviews by Steentoft et al., *Glycobiology* 24(8):663-80 (2014); Belfort and Bonocora, *Methods Mol Biol.* 1123: 1-26 (2014); Hafez and Hausner, *Genome* 55(8):553-69 (2012); and references cited therein.

MegaTAL/Tev-mTALEN/MegaTev

As further examples of hybrid nucleases, the MegaTAL platform and Tev-mTALEN platform use a fusion of the TALE DNA binding domains to catalytically active HEs, taking advantage of both the tunable DNA binding and specificity of the TALE as well as the cleavage sequence specificity of the HE; see, e.g., Boissel et al., NAR 42: 2591-2601 (2014); Kleinstiver et al., G3 4:1155-65 (2014); and Boissel and Scharenberg, *Methods Mol. Biol.* 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on DNA substrate and generate two DSBs with non-compatible cohesive ends; see, e.g., Wolfs et al., NAR 42, 8816-29 (2014). It is anticipated that other combinations of existing nuclease-based approaches will evolve and be useful in achieving the targeted genome modifications described herein.

dCas9-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create the DSB. The specificity of targeting is driven by a 20 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated particularly in the 5' half of the target sequence, effectively reducing the number of bases that drive specificity. One solution to this has been to completely deactivate the Cas9 catalytic function—retaining only the RNA-guided DNA binding function—and instead fusing a FokI domain to the deactivated Cas9; see, e.g., Tsai et al., *Nature Biotech* 32: 569-76 (2014); and Guilinger et al., *Nature Biotech.* 32: 577-82 (2014). Since FokI must dimerize to become catalytically active, two guide RNAs are required to tether two Cas9-FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE such as I-TevI takes advantage of both the tunable DNA binding and specificity of the TALE as well as the cleavage sequence specificity of I-TevI, with the expectation that off-target cleavage may be further reduced.

CRISPR/Cas Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders such as virus and phage. There are three stages of CRISPR locus function: integration of new sequences into the locus, biogenesis of CRISPR RNA (crRNA), and silencing of foreign invader nucleic acid. Four types of CRISPR systems (e.g., Type I, Type II, Type III, Type U) have been identified.

A CRISPR locus includes a number of short repeating sequences referred to as "repeats." The repeats can form hairpin structures and/or comprises unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes the spacer sequence targets the foreign invader nucleic acid). A spacer sequence is located at the 5' or 3' end of the crRNA.

A CRISPR locus also comprises polynucleotide sequences encoding Crispr Associated (Cas) genes. Cas genes encode endonucleases involved in the biogenesis and the interference stages of crRNA function in prokaryotes. Some Cas genes comprises homologous secondary and/or tertiary structures.

Type II CRISPR Systems crRNA biogenesis in a Type II CRISPR system in nature requires a trans-activating CRISPR RNA (tracrRNA). The tracrRNA is modified by endogenous RNaseIII and then hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science,* 337 (6096):816-821 (2012) showed the CRISPR/Cas9 system is useful for RNA-programmable genome editing, and WO2013/176772 provides numerous examples and applications of the CRISPR/Cas endonuclease system for site-specific gene editing.

Cas Genes/Polypeptides and Protospacer Adjacent Motifs

Exemplary CRISPR Cas polypeptides include Cas9 polypeptides in FIG. 1 of Fonfara et al., *Nucleic Acids Research,* 42: 2577-2590 (2014). The CRISPR-Cas gene naming system has undergone extensive rewriting since the Cas genes were discovered. FIG. 5 of Fonfara, supra, provides PAM sequences for Cas9 polypeptides from various species.

Site-Directed Polypeptides

A site-directed polypeptide in the present disclosure is a nuclease used in genome editing to cleave DNA.

In the context of a CRISPR/Cas system herein, the site-directed polypeptide can bind to a guide RNA that, in turn, specifies the site in the target DNA to which the polypeptide is directed. In embodiments of CRISPR/Cas systems herein, the site-directed polypeptide is an endonuclease.

In some embodiments, a site-directed polypeptide comprises a plurality of nucleic acid-cleaving (i.e., nuclease) domains. Two or more nucleic acid-cleaving domains can be linked together via a linker. In some embodiments, the linker comprises a flexible linker. Linkers comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, an HNH nuclease domain and a RuvC domain. Herein, the "Cas9" refers to both naturally-occurring and recombinant Cas9s. Cas9 enzymes contemplated herein comprises a HNH or HNH-like nuclease domain and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., divalent cation binding site). HNH or HNH-like domains can cleave one strand of a target nucleic acid (e.g., complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., divalent cation binding site). RuvC/RNaseH or RuvC/RNaseH-like domains can cleave one strand of a target nucleic acid (e.g., non-complementary strand of double-stranded target DNA).

Site-directed polypeptides can introduce double-strand breaks or single-strand breaks in nucleic acid, (e.g., genomic DNA). The double-strand break can stimulate a cell's endogenous DNA-repair pathways (e.g., homology-dependent repair (HDR) and non-homologous end joining (NHEJ)

or alternative non-homologous end joining (A-NHEJ) or microhomology-mediated end joining (MMEJ)). NHEJ can repair cleaved target nucleic acid without the need for a homologous template. This can sometimes result in small deletions or insertions (indels) in the target nucleic acid at the site of cleavage and can lead to disruption or alteration of gene expression. HDR can occur when a homologous repair template, or donor, is available. The homologous donor template comprises sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide or viral nucleic acid. With exogenous donor templates it is common to introduce additional nucleic acid sequence (such as a transgene) or modification (such as a single base change or a deletion) between the flanking regions of homology so additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few basepairs flanking the cleavage site to drive a favored end-joining DNA repair outcome. In some instances it may be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

In some embodiments, the site-directed polypeptide comprises an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to a wild type exemplary site-directed polypeptide [e.g., Cas9 from *S. pyogenes*, US2014/0068797 Sequence ID No. 8 or Sapranauskas et al., *Nucleic Acids Res*, 39(21): 9275-9282 (2011)], and various other site-directed polypeptides).

In some embodiments, the site-directed polypeptide comprises an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100%, amino acid sequence identity to the nuclease domain of a wild type exemplary site-directed polypeptide (e.g., Cas9 from *S. pyogenes*, supra).

In some embodiments, a site-directed polypeptide comprises at least 70, 75, 80, 85, 90, 95, 97, 99, or 100% identity to wild-type site-directed polypeptide (e.g., Cas9 from *S. pyogenes*, supra) over 10 contiguous amino acids. In some embodiments, a site-directed polypeptide comprises at most: 70, 75, 80, 85, 90, 95, 97, 99, or 100% identity to wild-type site-directed polypeptide (e.g., Cas9 from *S. pyogenes*, supra) over 10 contiguous amino acids. In some embodiments, a site-directed polypeptide comprises at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. In some embodiments, a site-directed polypeptide comprises at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. In some embodiments, a site-directed polypeptide comprises at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. In some embodiments, a site-directed polypeptide comprises at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

In some embodiments, the site-directed polypeptide comprises a modified form of a wild type exemplary site-directed polypeptide. The modified form of the wild type exemplary site-directed polypeptide comprises a mutation that reduces the nucleic acid-cleaving activity of the site-directed polypeptide. In some embodiments, the modified form of the wild type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide comprises a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). In some embodiments, the mutation results in one or more of the plurality of nucleic acid-cleaving domains retaining the ability to cleave the complementary strand of the target nucleic acid but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid but reducing its ability to cleave the complementary strand of the target nucleic acid. For example, residues in the wild type exemplary *S. pyogenes* Cas9 polypeptide such as Asp10, His840, Asn854 and Asn856 are mutated to inactivate one or more of the plurality of nucleic acid-cleaving domains (e.g., nuclease domains). In some embodiments, the residues to be mutated correspond to residues Asp10, His840, Asn854 and Asn856 in the wild type exemplary *S. pyogenes* Cas9 polypeptide (e.g., as determined by sequence and/or structural alignment). Non-limiting examples of mutations can include D10A, H840A, N854A or N856A. One skilled in the art will recognize that mutations other than alanine substitutions are suitable.

In some embodiments, a D10A mutation is combined with one or more of H840A, N854A, or N856A mutations to produce a site-directed polypeptide substantially lacking DNA cleavage activity. In some embodiments, a H840A mutation is combined with one or more of D10A, N854A, or N856A mutations to produce a site-directed polypeptide substantially lacking DNA cleavage activity. In some embodiments, a N854A mutation is combined with one or more of H840A, D10A, or N856A mutations to produce a site-directed polypeptide substantially lacking DNA cleavage activity. In some embodiments, a N856A mutation is combined with one or more of H840A, N854A, or D10A mutations to produce a site-directed polypeptide substantially lacking DNA cleavage activity. Site-directed polypeptides that comprise one substantially inactive nuclease domain are referred to herein as nickases.

Nickase variants of Cas9 can be used to increase the specificity of CRISPR-mediated genome editing. Wild type Cas9 is typically guided by a single guide RNA designed to hybridize with a specified ~20 nt sequence in the target sequence (such as an endogenous genomic locus). However, several mismatches can be tolerated between the guide RNA and the target locus, effectively reducing the length of required homology in the target site to, for example, as little as 13 nt of homology and thereby resulting in elevated potential for binding and double-strand nucleic acid cleavage by the CRISPR/Cas9 complex elsewhere in the target genome—also known as off-target cleavage. Since nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes. Descriptions of various Crispr-Cas systems for use in gene editing can be found, e.g., in WO2013/176772, and in *Nature Biotechnology* 32, 347-355 (2014), and references cited therein.

Mutations contemplated include substitutions, additions, and deletions, or any combination thereof. In some embodiments, the mutation converts the mutated amino acid to alanine. In some embodiments, the mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). In some embodiments, the mutation converts the mutated amino acid to a non-natural amino acid (e.g., selenomethionine). In some embodiments, the mutation converts the mutated amino acid to amino acid mimics (e.g., phosphomimics). In some embodiments, the mutation is a conservative mutation. For example, the mutation can convert the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). In some embodiments, the mutation causes a shift in reading frame and/or the creation of a premature stop codon. In some embodiments mutations cause changes to regulatory regions of genes or loci that affect expression of one or more genes.

In some embodiments, the site-directed polypeptide (e.g., variant, mutated, enzymatically inactive and/or conditionally enzymatically inactive site-directed polypeptide) targets nucleic acid. In some embodiments, the site-directed polypeptide (e.g., variant, mutated, enzymatically inactive and/or conditionally enzymatically inactive endoribonuclease) can target RNA.

In some embodiments, the site-directed polypeptide comprises one or more non-native sequences (e.g., the site-directed polypeptide is a fusion protein).

In some embodiments, the site-directed polypeptide comprises an amino acid sequence comprising at least 15% amino acid identity to a Cas9 from a bacterium (e.g., *S. pyogenes*), a nucleic acid binding domain, and two nucleic acid cleaving domains (i.e., an HNH domain and a RuvC domain).

In some embodiments, the site-directed polypeptide comprises an amino acid sequence comprising at least 15% amino acid identity to a Cas9 from a bacterium (e.g., *S. pyogenes*), and two nucleic acid cleaving domains (i.e., an HNH domain and a RuvC domain).

In some embodiments, the site-directed polypeptide comprises an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

In some embodiments, the site-directed polypeptide comprises an amino acid sequence comprising at least 15% amino acid identity to a Cas9 from a bacterium (e.g., *S. pyogenes*), two nucleic acid cleaving domains (i.e., an HNH domain and a RuvC domain), and non-native sequence (for example, a nuclear localization signal) or a linker linking the site-directed polypeptide to a non-native sequence.

In some embodiments, the site-directed polypeptide comprises an amino acid sequence comprising at least 15% amino acid identity to a Cas9 from a bacterium (e.g., *S. pyogenes*), two nucleic acid cleaving domains (i.e., an HNH domain and a RuvC domain), wherein the site-directed polypeptide comprises a mutation in one or both of the nucleic acid cleaving domains that reduces the cleaving activity of the nuclease domains by at least 50%.

In some embodiments, the site-directed polypeptide comprises an amino acid sequence comprising at least 15% amino acid identity to a Cas9 from a bacterium (e.g., *S. pyogenes*), and two nucleic acid cleaving domains (i.e., an HNH domain and a RuvC domain), wherein one of the nuclease domains comprises mutation of aspartic acid 10, and/or wherein one of the nuclease domains comprises mutation of histidine 840, and wherein the mutation reduce the cleaving activity of the nuclease domain(s) by at least 50%.

In some embodiments, the site-directed polypeptide sequence contains modificaitons that enhance specificity by limiting non-specific DNA interactions, and/or increasing the sequence-specific interactions. These changes may alternatively or additionally serve to change the kinetics of the binding, cleavage or retention on the cleaved DNA ends.

Nucleic Acid-Targeting Nucleic Acid

The present disclosure provides a nucleic acid-targeting nucleic acid that can direct the activities of an associated polypeptide (e.g., a site-directed polypeptide) to a specific target sequence within a target nucleic acid. In some embodiments, the nucleic acid-targeting nucleic acid is an RNA. A nucleic acid-targeting RNA is referred to as a "guide RNA" herein. A guide RNA comprises at least a spacer sequence that hybridizes to a target nucleic acid sequence of interest, a CRISPR repeat sequence and a tracrRNA sequence. In the guide RNA, the CRISPR repeat sequence and tracrRNA sequence hybridize to each other to form a duplex. The duplex binds a site-directed polypeptide such that the guide RNA and site-direct polypeptide form a complex. The nucleic acid-targeting nucleic acid provides target specificity to the complex by virtue of its association with the site-directed polypeptide. The nucleic acid-targeting nucleic acid thus directs the activity of the site-directed polypeptide.

Exemplary guide RNAs include the guide RNAs in Table 1 shown with their genomic target sequence, the genome location of their target sequence and the associated Cas9 cut site, wherein the target sequence and genome location are based on the GRCh38/hg38 human genome assembly. As is understood by the person of ordinary skill in the art, each guide RNA is designed to include a spacer sequence complementary to its genomic target sequence.

TABLE 1

| Guide | Sequence | SEQ ID NO | Location | Cut Site |
|---|---|---|---|---|
| | | HPFH5 | | |
| HPFH5-01 | gCTTCCATTCTAACCCACAT | SEQ ID NO: 1 | Chr11:5237801-5237823 | Chr11:5237807 |
| HPFH5-02 | gTACTGAGTTCTAAAATCAT | SEQ ID NO: 2 | Chr11:5237758-5237780 | Chr11:5237764 |
| HPFH5-03 | gACTGAGTTCTAAAATCATc | SEQ ID NO: 3 | Chr11:5237757-5237779 | Chr11:5237763 |
| HPFH5-04 | gCTGAGTTCTAAAATCATCG | SEQ ID NO: 4 | Chr11:5237756-5237778 | Chr11:5237762 |
| HPFH5-05 | gCTAAAATCATCGGGGATTT | SEQ ID NO: 5 | Chr11:5237749-5237771 | Chr11:5237755 |
| HPFH5-06 | gTAAAATCATCGGGGATTTT | SEQ ID NO: 6 | Chr11:5237748-5237770 | Chr11:5237754 |
| HPFH5-07 | gAAAATCATCGGGGATTTTG | SEQ ID NO: 7 | Chr11:5237747-5237769 | Chr11:5237753 |
| HPFH5-08 | gGAGATTTCACATTAAATGT | SEQ ID NO: 8 | Chr11:5237700-5237722 | Chr11:5237706 |
| HPFH5-09 | gATGCCAATGTGGGTTAGAA | SEQ ID NO: 9 | Chr11:5237797-5237819 | Chr11:5237813 |
| HPFH5-10 | gATTAGTGTAATGCCAATGT | SEQ ID NO: 10 | Chr11:5237788-5237810 | Chr11:5237804 |
| HPFH5-11 | gCATTTAATGTGAAATCTCA | SEQ ID NO: 11 | Chr11:5237703-5237725 | Chr11:5237719 |
| HPFH5-12 | gAATTAGTGTAATGCCAATG | SEQ ID NO: 12 | Chr11:5237787-5237809 | Chr11:5237803 |
| HPFH5-13 | gGGACTGAGAAGAATTTGAA | SEQ ID NO: 13 | Chr11:5224813-5224835 | Chr11:5224819 |
| HPFH5-14 | gCTGAGAAGAATTTGAAAGG | SEQ ID NO: 14 | Chr11:5224810-5224832 | Chr11:5224816 |
| HPFH5-15 | gTGTCTTATTACCCTGTCAT | SEQ ID NO: 15 | Chr11:5224763-5224785 | Chr11:5224769 |
| HPFH5-16 | gGTCATAGGCCCACCCCAAA | SEQ ID NO: 16 | Chr11:5224749-5224771 | Chr11:5224755 |
| HPFH5-17 | gGGAAGTCCCATTCTTccTc | SEQ ID NO: 17 | Chr11:5224729-5224750 | Chr11:5224735 |
| HPFH5-18 | gATGTTTAAGATTAGCATTc | SEQ ID NO: 18 | Chr11:5224707-5224729 | Chr11:5224713 |
| HPFH5-19 | gTTGGGGTGGGCCTATGACA | SEQ ID NO: 19 | Chr11:5224752-5224774 | Chr11:5224768 |
| HPFH5-20 | gTTTGGGGTGGGCCTATGAc | SEQ ID NO: 20 | Chr11:5224751-5224773 | Chr11:5224767 |
| HPFH5-21 | gTGGGACTTCCATTTGGGGT | SEQ ID NO: 21 | Chr11:5224740-5224762 | Chr11:5224756 |
| HPFH5-22 | gATGGGACTTCCATTTGGGG | SEQ ID NO: 22 | Chr11:5224739-5224761 | Chr11:5224755 |
| HPFH5-23 | gAGAATGGGACTTCCATTTG | SEQ ID NO: 23 | Chr11:5224736-5224758 | Chr11:5224752 |
| HPFH5-24 | gAAGAATGGGACTTCCATTT | SEQ ID NO: 24 | Chr11:5224735-5224757 | Chr11:5224751 |
| HPFH5-25 | gGAAGAATGGGACTTCCATT | SEQ ID NO: 25 | Chr11:5224734-5224756 | Chr11:5224750 |
| HPFH5-26 | gAAACATCCTGAGGAAGAAT | SEQ ID NO: 26 | Chr11:5224722-5224744 | Chr11:5224738 |
| HPFH5-27 | gTAAACATCCTGAGGAAGAA | SEQ ID NO: 27 | Chr11:5224721-5224743 | Chr11:5224737 |

TABLE 1-continued

| | | | | |
|---|---|---|---|---|
| HPFH5-28 | gGCTAATCTTAAACATCCTG | SEQ ID NO: 28 | Chr11:5224713-5224735 | Chr11:5224729 |
| HPFH5-29 | gTGGTATGGGAGGTATACTA | SEQ ID NO: 29 | Chr11:5237949-5237971 | Chr11:5237965 |
| HPFH5-30 | gATCTCGAACTCCTAACATc | SEQ ID NO: 30 | Chr11:5238088-5238110 | Chr11:5238094 |
| HPFH5-31 | gGTATACCTCCCATACCATG | SEQ ID NO: 31 | Chr11:5237945-5237967 | Chr11:5237951 |
| HPFH5-32 | gGAGTGCAATGGCATGATCC | SEQ ID NO: 32 | Chr11:5238256-5238278 | Chr11:5238262 |
| HPFH5-34 | gAGCATTGCTATGGTTGCCC | SEQ ID NO: 33 | Chr11:5238281-5238303 | Chr11:5238287 |
| HPFH5_35 | gGAATTCACCCCACCAGTGc | SEQ ID NO: 34 | Chr11:5225657-5225679 | Chr11:5225663 |
| HPFH5_36 | gACAGACCAGCACGTTGCCC | SEQ ID NO: 35 | Chr11:5225702-5225724 | Chr11:5225718 |
| HPFH5_37 | gCAGCTCCTGGGCAACGTGC | SEQ ID NO: 36 | Chr11:5225708-5225730 | Chr11:5225714 |
| HPFH5_38 | gTTAGCAAAAGGGCCTAGCT | SEQ ID NO: 37 | Chr11:5225758-5225780 | Chr11:5225774 |
| HPFH5_39 | gATTATTCTGAGTCCAAGCT | SEQ ID NO: 38 | Chr11:5225771-5225793 | Chr11:5225777 |
| HPFH5_40 | gGCTGCTGGTGGTCTACCCT | SEQ ID NO: 39 | Chr11:5226778-5226800 | Chr11:5226784 |
| HPFH5_41 | gGTAGACCACCAGCAGCCTA | SEQ ID NO: 40 | Chr11:5226783-5226805 | Chr11:5226799 |
| HPFH5_42 | gTAGACCACCAGCAGCCTAA | SEQ ID NO: 41 | Chr11:5226784-5226806 | Chr11:5226800 |
| HPFH5_43 | gCCACCAGCAGCCTAAGGGT | SEQ ID NO: 42 | Chr11:5226788-5226810 | Chr11:5226804 |
| HPFH5_44 | gGGTGGGAAAATAGACCAAT | SEQ ID NO: 43 | Chr11:5226804-5226826 | Chr11:5226820 |
| HPFH5_45 | gCCCAAAGTGTGACTATCAA | SEQ ID NO: 44 | Chr11:5227835-5227857 | Chr11:5227851 |
| HPFH5_46 | gCCCATTGATAGTCACACTT | SEQ ID NO: 45 | Chr11:5227837-5227859 | Chr11:5227843 |
| HPFH5_47 | gCCAAAGTGTGACTATCAAT | SEQ ID NO: 46 | Chr11:5227836-5227858 | Chr11:5227852 |
| HPFH5_48 | gCTATCAATGGGTAATCAG | SEQ ID NO: 47 | Chr11:5227847-5227869 | Chr11:5227863 |
| HPFH5_49 | gGTAATCAGTGGTGTCAAAT | SEQ ID NO: 48 | Chr11:5227858-5227880 | Chr11:5227874 |
| HPFH5_50 | gACCTGTCTCAACCCTCATc | SEQ ID NO: 49 | Chr11:5228644-5228666 | Chr11:5228660 |
| HPFH5_51 | gACCTGATGAGGGTTGAGAc | SEQ ID NO: 50 | Chr11:5228646-5228668 | Chr11:5228652 |
| HPFH5_52 | gCACACACGCAGAAAGTGTT | SEQ ID NO: 51 | Chr11:5228698-5228720 | Chr11:5228714 |
| HPFH5_53 | gTGGTTCTTCTATGGCTATc | SEQ ID NO: 52 | Chr11:5228717-5228739 | Chr11:5228733 |
| HPFH5_54 | gTGCCTATGTATGATTATAG | SEQ ID NO: 53 | Chr11:5228758-5228780 | Chr11:5228774 |
| HPFH5_55 | gTATCAGAATGGCCCTAGTc | SEQ ID NO: 54 | Chr11:5229840-5229862 | Chr11:5229856 |
| HPFH5_56 | gATCAGAATGGCCCTAGTCT | SEQ ID NO: 55 | Chr11:5229841-5229863 | Chr11:5229857 |
| HPFH5_57 | gTCTAAGTATACCCAGACTA | SEQ ID NO: 56 | Chr11:5229852-5229874 | Chr11:5229858 |
| HPFH5_58 | gCTCTAAGTATACCCAGACT | SEQ ID NO: 57 | Chr11:5229853-5229875 | Chr11:5229859 |
| HPFH5_59 | gCTAGTCTGGGTATACTTAG | SEQ ID NO: 58 | Chr11:5229854-5229875 | Chr11:5229869 |
| HPFH5_60 | gTTCAGTATGTCTGAATGAA | SEQ ID NO: 59 | Chr11:5230701-5230723 | Chr11:5230707 |
| HPFH5_61 | gAAATTAAGCCAAATCTTG | SEQ ID NO: 60 | Chr11:5230786-5230808 | Chr11:5230802 |
| HPFH5_62 | gGAATTAATTCCTCAAGATT | SEQ ID NO: 61 | Chr11:5230796-5230818 | Chr11:5230802 |
| HPFH5_63 | gTTAAAACAAAGTATAGGAA | SEQ ID NO: 62 | Chr11:5230817-5230839 | Chr11:5230823 |
| HPFH5_64 | gGTACATGTACAAGTTATAT | SEQ ID NO: 63 | Chr11:5230858-5230880 | Chr11:5230874 |
| HPFH5_65 | gACACATTGTCAGTATATTc | SEQ ID NO: 64 | Chr11:5231674-5231696 | Chr11:5231690 |
| HPFH5_66 | gATCCTTCTAATTTTACCTA | SEQ ID NO: 65 | Chr11:5231840-5231862 | Chr11:5231856 |
| HPFH5_67 | gTGCCATAGGTAAAATTAGA | SEQ ID NO: 66 | Chr11:5231843-5231865 | Chr11:5231849 |
| HPFH5_68 | gTGAGCACCATTTTTGCCAT | SEQ ID NO: 67 | Chr11:5231856-5231877 | Chr11:5231862 |

TABLE 1-continued

| | | | | |
|---|---|---|---|---|
| HPFH5_69 | gATGGCAAAAATGGTGCTCAC | SEQ ID NO: 68 | Chr11:5231858-5231880 | Chr11:5231874 |
| HPFH5_70 | gCACCCATTAATGCCTTGTA | SEQ ID NO: 69 | Chr11:5232689-5232710 | Chr11:5232704 |
| HPFH5_71 | gAACCGTACAAGGCATTAAT | SEQ ID NO: 70 | Chr11:5232691-5232712 | Chr11:5232697 |
| HPFH5_72 | gGAACCGTACAAGGCATTAA | SEQ ID NO: 71 | Chr11:5232692-5232714 | Chr11:5232698 |
| HPFH5_73 | gAAAGCAAGGGAACCGTACA | SEQ ID NO: 72 | Chr11:5232701-5232723 | Chr11:5232707 |
| HPFH5_74 | gTCCCTATCTGTAGAGccTc | SEQ ID NO: 73 | Chr11:5232762-5232783 | Chr11:5232777 |
| HPFH5_75 | gAGCCTCTCCCATACCCATG | SEQ ID NO: 74 | Chr11:5233650-5233672 | Chr11:5233666 |
| HPFH5_76 | gCTCCACATGGGTATGGCAG | SEQ ID NO: 75 | Chr11:5233653-5233675 | Chr11:5233659 |
| HPFH5_77 | gTGTCTCTCCACATGGGTAT | SEQ ID NO: 76 | Chr11:5233658-5233680 | Chr11:5233664 |
| HPFH5_78 | gTTGTCTCTCCACATGGGTA | SEQ ID NO: 77 | Chr11:5233659-5233681 | Chr11:5233665 |
| HPFH5_79 | gTTCTAAGTGCAGAATTAGC | SEQ ID NO: 78 | Chr11:5233688-5233710 | Chr11:5233704 |
| HPFH5_80 | gGCGGTGGGGAGATATGTAG | SEQ ID NO: 79 | Chr11:5234677-5234699 | Chr11:5234683 |
| HPFH5_81 | gTGCTGAAAGAGATGCGGTG | SEQ ID NO: 80 | Chr11:5234690-5234712 | Chr11:5234696 |
| HPFH5_82 | gCTGCTGAAAGAGATGCGGT | SEQ ID NO: 81 | Chr11:5234691-5234713 | Chr11:5234697 |
| HPFH5_83 | gACTGCTGAAAGAGATGCGG | SEQ ID NO: 82 | Chr11:5234692-5234714 | Chr11:5234698 |
| HPFH5_84 | gGTGTTTTAGGCTAATATAG | SEQ ID NO: 83 | Chr11:5234752-5234774 | Chr11:5234768 |
| HPFH5_85 | gTCAAATTTTGGTGGTGATA | SEQ ID NO: 84 | Chr11:5235684-5235706 | Chr11:5235700 |
| HPFH5_86 | gTACAATAGTATAACCCCTT | SEQ ID NO: 85 | Chr11:5235740-5235762 | Chr11:5235756 |
| HPFH5_87 | gCATTTGTGGATACTATTAA | SEQ ID NO: 86 | Chr11:5235767-5235789 | Chr11:5235773 |
| HPFH5_88 | gTAATAGTATCCACAAATGC | SEQ ID NO: 87 | Chr11:5235770-5235792 | Chr11:5235786 |
| HPFH5_89 | gATCAAGCATCCAGCATTTG | SEQ ID NO: 88 | Chr11:5235780-5235802 | Chr11:5235786 |
| HPFH5_90 | gTGTCATTTTTAACAGGTAG | SEQ ID NO: 89 | Chr11:5236644-5236666 | Chr11:5236650 |
| HPFH5_91 | gGTAAATTCTTAAGGCCATG | SEQ ID NO: 90 | Chr11:5236773-5236795 | Chr11:5236789 |
| HPFH5_92 | gGATCAAATAACAGTCCTCA | SEQ ID NO: 91 | Chr11:5236788-5236810 | Chr11:5236794 |
| HPFH5_93 | gTCTGTTAATTCCAAAGACT | SEQ ID NO: 92 | Chr11:5236813-5236835 | Chr11:5236829 |
| HPFH5_94 | gCTGAAATGATTTTACACAT | SEQ ID NO: 93 | Chr11:5236859-5236881 | Chr11:5236875 |
| HPFH5-95 | gAGGATGAGCCACATGGTAT | SEQ ID NO: 94 | Chr11:5237936-5237958 | Chr11:5237952 |
| HPFH5-96 | gATGAGCCACATGGTATCGG | SEQ ID NO: 95 | Chr11:5237939-5237961 | Chr11:5237955 |
| HPFH5-97 | gGAGGTATACTAAGGACTCT | SEQ ID NO: 96 | Chr11:5237957-5237979 | Chr11:5237973 |
| HPFH5-98 | gTTTGGGGTGGGCCTATGAc | SEQ ID NO: 97 | Chr11:5224751-5224773 | Chr11:5224767 |
| HPFH5-99 | gGTAGGTAGATGCTAGATTC | SEQ ID NO: 98 | Chr11:5224565-5224587 | Chr11:5224571 |
| HPFH5-100 | gTCTTATTCAATACCTAGGT | SEQ ID NO: 99 | Chr11:5224582-5224604 | Chr11:5224588 |
| HPFH5-101 | gCACCATAAGGGACATGATA | SEQ ID NO: 100 | Chr11:5224660-5224682 | Chr11:5224676 |
| HPFH5-102 | gATGTCCCTTATGGTGCTTc | SEQ ID NO: 101 | Chr11:5224654-5224676 | Chr11:5224660 |
| HPFH5-103 | gCAGTAGAGGTATGGTTTCC | SEQ ID NO: 102 | Chr11:5223857-5223879 | Chr11:5223863 |
| HPFH5-104 | gATCTAGCATCTACCTACCT | SEQ ID NO: 103 | Chr11:5224569-5224591 | Chr11:5224585 |
| Corfu | | | | |
| HPFHCS-01 | gATTACTGGTGGTCTACCCT | SEQ ID NO: 104 | Chr11:5234192-5234214 | Chr11:5234198 |
| HPFHCS-02 | gTAGACCACCAGTAATCTGA | SEQ ID NO: 105 | Chr11:5234198-5234220 | Chr11:5234214 |
| HPFHCS-03 | gCCTACCCTCAGATTACTGG | SEQ ID NO: 106 | Chr11:5234203-5234225 | Chr11:5234209 |

TABLE 1-continued

| Guide | Sequence | Location | Cut Site |
|---|---|---|---|
| HPFHCS-04 | gTGGTATGGGAGGTATACTAS | Chr11:5237949-5237971 | Chr11:5237965 |
| HPFHCS-05 | gATCTCGAACTCCTAACATCS | Chr11:5238088-5238110 | Chr11:5238094 |
| HPFHCS-06 | gGTATACCTCCCATACCATGS | Chr11:5237945-5237967 | Chr11:5237951 |
| HPFHCS-07 | gCTAAAATCATCGGGGATTTS | Chr11:5237749-5237771 | Chr11:5237755 |
| HPFHCL-01 | gGTGTGCTGGCCCGCAACTTS | Chr11:5233049-5233071 | Chr11:5233055 |
| HPFHCL-02 | gTGGGGCAGAAGTCGTTGCTS | Chr11:5233476-5233498 | Chr11:5233482 |
| HPFHCL-03 | gCTGGCCCGCAACTTTGGCAS | Chr11:5233044-5233066 | Chr11:5233050 |
| HPFHCL-04 | gAACCGTACAAGGCATTAATS | Chr11:5232691-5232713 | Chr11:5232697 |
| HPFHCL-05 | gAAAGCAAGGGAACCGTACAS | Chr11:5232701-5232723 | Chr11:5232707 |
| HPFHCL-06 | gGAACCGTACAAGGCATTAAS | Chr11:5232692-5232714 | Chr11:5232698 |
| HPFHCL-07 | gTCAATGGTACTTGTGAGCCS | Chr11:5232963-5232985 | Chr11:5232979 |
| HPFHCL-08 | gCCACTCAAGAGATATGGTGS | Chr11:5240337-5240359 | Chr11:5240353 |
| HPFHCL-09 | gCAAGCCCCTGTTTGGATCS | Chr11:5240557-5240579 | Chr11:5240563 |
| HPFHCL-10 | gTGCCTACAAGCCCCTGTTS | Chr11:5240563-5240585 | Chr11:5240569 |

Kenya

| HPFHK-01 | gCCTCGAGACTAAAGGCAACS | Chr11:5249322-5249344 | Chr11:5249338 |
| HPFHK-02 | gTCTTCAGCCTACAACATACS | Chr11:5248713-5248735 | Chr11:5248719 |
| HPFHK-03 | gCCCTTCAAGCACTAGTCAcS | Chr11:5248651-5248673 | Chr11:5248667 |
| HPFHK-04 | gGCCAGTGACTAGTGCTTGAS | Chr11:5248653-5248675 | Chr11:5248659 |
| HPFHK-05 | gCTCGAGGCAACTTAGACAAS | Chr11:5249308-5249330 | Chr11:5249314 |
| HPFHK-06 | gCCAGTGACTAGTGCTTGAAS | Chr11:5248652-5248674 | Chr11:5248658 |
| HPFHK-07 | gCTCGAGACTAAAGGCAACAS | Chr11:5249323-5249345 | Chr11:5249339 |
| HPFHK-08 | gCAGTGACTAGTGCTTGAAGS | Chr11:5248651-5248673 | Chr11:5248657 |
| HPFHK-09 | gTTAGCAAAAGGGCCTAGCTS | Chr11:5225758-5225780 | Chr11:5225774 |
| HPFHK-10 | gTGCCTAGTACATTACTATTS | Chr11:5226235-5226257 | Chr11:5226241 |
| HPFHK-11 | gACAGACCAGCACGTTGCCCS | Chr11:5225702-5225724 | Chr11:5225718 |
| HPFHK-12 | gTACACATATTGACCAAATCS | Chr11:5226096-5226118 | Chr11:5226102 |
| HPFHK-13 | gCAGCTCCTGGGCAACGTGCS | Chr11:5225708-5225730 | Chr11:5225714 |
| HPFHK-14 | gACGAATGATTGCATCAGTGS | Chr11:5226448-5226470 | Chr11:5226454 |
| HPFHK-15 | gATTATTCTGAGTCCAAGCTS | Chr11:5225771-5225793 | Chr11:5225777 |
| HPFHK-16 | gGTGTGCTGGCCCATCACTTS | Chr11:5225683-5225705 | Chr11:5225689 |
| HPFHK-17 | gTTAAGTTCATGTCATAGGAS | Chr11:5226507-5226529 | Chr11:5226513 |

Small Deletion

| Guide | Sequence | Location | Cut Site | Location | Cut Site |
|---|---|---|---|---|---|
| HPFHSD_01 | gTTTGCCTTGTCAAGGCTAT | Chr11:5249950-5249972 | Chr11:5249966 | Chr11:5254874-5254896 | Chr11:5254890 |
| HPFHSD_02 | gTTGTCAAGGCTATTGGTCA | Chr11:5249956-5249978 | Chr11:5249972 | Chr11:5254880-5254902 | Chr11:5254896 |
| HPFHSD_03 | gTTGACCAATAGCCTTGACA | Chr11:5249955-5249977 | Chr11:5249961 | Chr11:5254879-5254901 | Chr11:5254885 |

TABLE 1-continued

| | | | | | |
|---|---|---|---|---|---|
| HPFHSD_04 | gAAGGCTATTGGTCAAGGCA | Chr11:5249961-5249983 | Chr11:5249977 | Chr11:5254885-5254907 | Chr11:5254901 |
| HPFHSD_05 | gCTATTGGTCAAGGCAAGGCC | Chr11:5249965-5249987 | Chr11:5249981 | Chr11:5254889-5254911 | Chr11:5254905 |

HPFHSD_01 = SEQ ID NO: 138
HPFHSD_02 = SEQ ID NO: 139
HPFHSD_03 = SEQ ID NO: 140
HPFHSD_04 = SEQ ID NO: 141
HPFHSD_05 = SEQ ID NO: 142

In some embodiments, the nucleic acid-targeting nucleic acid is a double-molecule guide RNA. In some embodiments, the nucleic acid-targeting nucleic acid is a single-molecule guide RNA.

A double-molecule guide RNA comprises two strands of RNA. The first strand comprises in the 5' to 3' direction, an optional spacer extension sequence, a spacer sequence and a minimum CRISPR repeat sequence. The second strand comprises a minimum tracrRNA sequence (complementary to the minimum CRISPR repeat sequence), a 3' tracrRNA sequence and an optional tracrRNA extension sequence.

A single-molecule guide RNA comprises in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may comprise elements that contribute additional functionality (e.g., stability) to the guide RNA. The single-molecule guide linker links the minimum CRISPR repeat and the minimum tracrRNA sequence to form a hairpin structure. The optional tracrRNA extension comprises one or more hairpins.

Modified Polynucleotides

In some embodiments, polynucleotides introduced into cells, including those described herein for use in treating hemoglobinopathies, comprise one or more modifications which can be used, for example, to enhance activity, stability or specificity, alter delivery, reduce innate immune responses in host cells, or for other enhancements, as further described herein and known in the art.

In certain embodiments, modified polynucleotides are used in the Crispr-Cas system, in which case the guide RNAs (either single-molecule guides or double-molecule guides) and/or a DNA or an RNA encoding a Cas endonuclease introduced into a cell can be modified, as described and illustrated below. Such modified polynucleotides can be used in the Crispr-Cas system to edit any one or more genomic loci, including without limitation genomic loci being edited to treat a hemoglobinopathy as described herein, and also or alternatively any other genomic loci to be edited using the Crispr-Cas system, using methods as described herein and in the art, and as illustrated herein in the context of treating a hemoglobinopathy, using guide RNAs designed to target loci associated with the β-globin region of chromosome 11. As will be appreciated by those of skill, modifications as described below for use in Crispr-Cas genome editing of the β-globin region, can also be used in Crispr-Cas genome editing of other targets.

In other embodiments, modified polynucleotides as described further herein can be used to encode other endonucleases, such as ZFN endonucleases, TALEN endonucleases or others, and/or other components of such systems, for use in treating hemoglobinopathies or other human genetic diseases.

Using the Crispr-Cas system for purposes of nonlimiting illustrations of such uses, modifications of guide RNAs can be used to enhance the formation or stability of the Crispr-Cas genome editing complex comprising guide RNAs, which may be single-molecule guides or double-molecule, and a Cas endonuclease such as Cas9. Modifications of guide RNAs can also or alternatively be used to enhance the initiation, stability or kinetics of interactions between the genome editing complex with the target sequence in the genome, which can be used for example to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half life in the cell to be increased. Modifications enhancing guide RNA half life can be particularly useful in embodiments in which a Cas endonuclease such as a Cas9 is introduced into the cell to be edited via an RNA that needs to be translated in order to generate Cas9 endonuclease, since increasing the half of guide RNAs introduced at the same time as the RNA encoding the endonuclease can be used to increase the time that the guide RNAs and the encoded Cas endonuclease co-exist in the cell. Similarly, the stability of the guide RNA can be modified to decrease the half-life.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half life of the RNA and/or the elicitation of cytokines or other factors associated with immune responses.

One or more types of modifications can also be made to RNAs encoding an endonuclease such as Cas9 that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of Crispr-Cas, for example, one or more types of modifications can be made to guide RNAs (including those exemplified above), and/or one or more types of modifications can be made to RNAs encoding Cas endonuclease (including those exemplified above).

By way of illustration, guide RNAs used in the Crispr-Cas system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modifed RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduced the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some embodiments a 2'-O-alkyl, 2'-O-alkyl-O-alkyl or 2'-fluoro-modified nucleotide. In some embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, ~N(CH3)~O~CH2 (known as a methylene(methylimino) or MMI backbone), CH2-O—N(CH3)-CH2, CH2-N(CH3)-N(CH3)-CH2 and O—N(CH3)-CH2-CH2 backbones, wherein the native phosphodiester backbone is represented as O— P— O— CH,); amide backbones [see De Mesmaeker et al., Ace. Chem. Res., 28:366-374 (1995)]; morpholino backbone structures (see Summerton and Weller, U.S. Pat. No. 5,034, 506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Braasch and David Corey, Biochemistry, 4/(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-0-$CH_2CH_2OCH_3$, also known as 2'-O-(2-methoxyethyl)) (Martin et al, Helv. Chim. Acta, 1995, 78, 486). Other modifications include 2'-methoxy (2'-0-$CH_3$), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262. Further teaching of PNA compounds can be found in Nielsen et al, *Science,* 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, pp 75-77 (1980); Gebeyehu et al., *Nucl. Acids Res.* 15:4513 (1997). A "universal" base known in the art, e.g., inosine, can also be included. 5-Me-C substitutions have been shown to increase nucleic acid duplex stability by 0.6-1.2 degrees C. (Sanghvi, Y. S., in Crooke, S. T. and Lebleu, B., eds., Antisense Research and Applications, CRC Press, Boca Raton, 1993, pp. 276-278) and are embodiments of base substitutions. Alternative bases may be added to alter the specificity, increase specificity, allow preferential targeting or may be included for other reasons.

Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are embodiments of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 20030158403.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, the guide RNAs and/or mRNA (or DNA) encoding an endonuclease such as Cas9 are chemically linked to one or more moieties or conjugates that enhance the activity, cellular distribution, or cellular uptake of the oligonucleotide. Such moieties comprise but are not limited to, lipid moieties such as a cholesterol moiety [Letsinger et al., *Proc. Natl. Acad. Sci. USA,* 86: 6553-6556 (1989)]; cholic acid [Manoharan et al., *Bioorg. Med. Chem. Let.,* 4: 1053-1060 (1994)]; a thioether, e.g., hexyl-S-tritylthiol [Manoharan et al, *Ann. N. Y. Acad. Sci.,* 660: 306-309 (1992) and Manoharan et al., *Bioorg. Med. Chem. Let.,* 3: 2765-2770 (1993)]; a thiocholesterol [Oberhauser et al., *Nucl. Acids Res.,* 20: 533-538 (1992)]; an aliphatic chain, e.g., dodecandiol or undecyl residues [Kabanov et al., *FEBS Lett.,* 259: 327-330 (1990) and Svinarchuk et al., *Biochimie,* 75: 49-54 (1993)]; a phospholipid, e.g., di-hexadecyl-rac-glycerol or triethylammonium 1,2-di-O-hexadecyl-rac-glycero-3-H-phosphonate [Manoharan et al., *Tetrahedron Lett.,* 36: 3651-3654 (1995) and Shea et al., *Nucl. Acids Res.,* 18: 3777-3783 (1990)]; a polyamine or a polyethylene glycol chain [Mancharan et al., *Nucleosides & Nucleotides,* 14: 969-973 (1995)]; adamantane acetic acid [Manoharan et al., *Tetrahedron Lett.,* 36: 3651-3654 (1995)]; a palmityl moiety [(Mishra et al., *Biochim. Biophys. Acta,* 1264: 229-237 (1995)]; or an octadecylamine or hexylamino-carbonyl-t oxycholesterol moiety [Crooke et al., *J. PharmacoL Exp. Ther.,* 277: 923-937 (1996)]. See also U.S. Pat. Nos. 4,828, 979; 4,948,882; 5,218,105; 5,525,465; 5,541,313; 5,545, 730; 5,552, 538; 5,578,717, 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762, 779; 4,789,737; 4,824,941; 4,835, 263; 4,876,335; 4,904,582; 4,958,013; 5,082, 830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391, 723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., *Protein Pept Lett.* 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium I,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation as illustrated in publications by Kormann et al. and Warren et al. referred to below.

It has been shown that chemically modified mRNA delivered in vivo can be used to achieve improved therapeutic effects; see, e.g., Kormann et al., *Nature Biotechnology* 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found substituting just one quarter of the uridine and cytidine residues with 2-Thio-U and 5-Methyl-C respectively, resulted in a significant decrease in toll-like receptor (TLR) mediated recognition of the mRNA in mice. By reducing the activation of the innate immune system, these modifications can therefore be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., *Cell Stem Cell,* 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules;

see, e.g., the reviews by Angart et al., *Pharmaceuticals (Basel)* 6(4): 440-468 (2013); Kanasty et al., Molecular Therapy 20(3): 513-524 (2012); Burnett et al., *Biotechnol J.* 6(9):1130-46 (2011); Judge and MacLachlan, *Hum Gene Ther*/9(2):111-24 (2008); and references cited therein.

A large variety of modifications have been developed and applied to enhance RNA stability, reduce innate immune responses, and/or achieve other benefits that can be useful in connection with the introduction of polynucleotides into human cells as described herein; see, e.g., the reviews by Whitehead K A et al., Annual Review of Chemical and Biomolecular Engineering, 2: 77-96 (2011); Gaglione and Messere, *Mini Rev Med Chem*, 10(7):578-95 (2010); Chernolovskaya et al, *Curr Opin Mol Ther.*, 12(2):158-67 (2010); Deleavey et al., *Curr Protoc Nucleic Acid Chem* Chapter 16:Unit 16.3 (2009); Behlke, *Oligonucleotides* 18(4):305-19 (2008); Fucini et al., *Nucleic Acid Ther* 22(3): 205-210 (2012); Bremsen et al., *Front Genet* 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, *Nature Reviews Drug Discovery* 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) has been associated with highly stable siRNAs for applications in vivo, as reported by Soutschek et al. *Nature* 432:173-178 (2004); and 2'-O-Methyl modifications have been reported to be effective in improving stability as reported by Volkov, *Oligonucleotides* 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., *Mol. Ther.* 13:494-505 (2006); and Cekaite et al., *J. Mol. Biol.* 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., *Immunity* 23:165-175 (2005).

As is also known in the art, and commercially available, a number of conjugates can be applied to polynucleotides such as RNAs for use herein that can enhance their delivery and/or uptake by cells, including for example, cholesterol, tocopherol and folic acid, lipids, peptides, polymers, linkers and aptamers; see, e.g., the review by Winkler, *Ther. Deliv.* 4:791-809 (2013), and references cited therein.

Various modifications as described herein or in the cited art, and/or other modifications described in the art with respect to polynucleotides designed to be delivered to human cells, can be used to modify one or more of the polynucleotides used as described herein for ameliorating hemoglobinopathies, including in the Crispr-Cas system, for example, modified guide RNAs and/or modified polynucleotides encoding Cas9 endonuclease. New modifications are regularly being developed in the art and these too can be applied in the context of the genome editing procedures described and illustrated herein.

Spacer Extension Sequence

In some embodiments of nucleic acid-targeting nucleic acids, a spacer extension sequence can provide stability and/or provide a location for modifications of a nucleic acid-targeting nucleic acid. In some embodiments, a spacer extension sequence is provided. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. In some embodiments, a spacer extension sequence comprises less than 10 nucleotides in length. In some embodiments, a spacer extension sequence comprises between 10 and 30 nucleotides in length. In some embodiments, a spacer extension sequence comprises between 30-70 nucleotides in length.

In some embodiments, the spacer extension sequence comprises another moiety (e.g., a stability control sequence, an endoribonuclease binding sequence, a ribozyme, or novel feature). In some embodiments, the moiety increases the stability of a nucleic acid targeting nucleic acid. In some embodiments, the moiety is a transcriptional terminator segment (i.e., a transcription termination sequence). In some embodiments, the moiety functions in a eukaryotic cell. In some embodiments, the moiety functions in a prokaryotic cell. In some embodiments, the moiety functions in both eukaryotic and prokaryotic cells.

Non-limiting examples of suitable moieties include: 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability, or any combination thereof.

Spacer Sequence

The spacer sequence hybridizes to a sequence in a target nucleic acid of interest. The spacer of a nucleic acid-targeting nucleic acid interacts with a target nucleic acid in a sequence-specific manner via hybridization (i.e., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of the Cas9 enzyme used in the system. Each Cas9 enzyme has a particular PAM sequence it recognizes in target DNA. For example, *S. pyogenes* recognizes in a target nucleic acid a PAM that comprises the sequence 5'-NRG-3', where R comprises either A or G, where N is any nucleotide and N is immediately 3' of the target nucleic acid sequence targeted by the spacer sequence.

In some embodiments, the target nucleic acid sequence comprises 20 nucleotides. In some embodiments, the target nucleic acid comprises less than 20 nucleotides. In some embodiments, the target nucleic acid comprises at least: 5, 10, 15, 16, 17, 18, 19, 20, 21, 22, 23, 24, 25, 30 or more nucleotides. In some embodiments, the target nucleic acid comprises at most: 5, 10, 15, 16, 17, 18, 19, 20, 21, 22, 23, 24, 25, 30 or more nucleotides. In some embodiments, the target nucleic acid sequence comprises 20 bases immediately 5' of the first nucleotide of the PAM. For example, in a sequence comprising 5'-NNNNNNNNNNNNNNNNNNNNNRG-3' (SEQ ID NO: 143), the target nucleic acid comprises the sequence that corresponds to the Ns, wherein N is any nucleotide. The spacer sequence use as gRNA can vary in length from the genomic target sequence and/or not be completely complementary. In one embodiment, 5' nucleotides may be included that do not match the target site in order to improve specificity.

In some embodiments, the spacer sequence that hybridizes to the target nucleic acid has a length at least about 6 nt. The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some embodiments, the spacer sequence comprises 20 nucleotides. In some embodiments, the spacer comprises 19 nucleotides.

In some embodiments, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some embodiments, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over about 20 contiguous nucleotides.

In some embodiments, a spacer sequence is designed or chosen using a computer program. The computer program can use variables such as predicted melting temperature, secondary structure formation, and predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some embodiments, a minimum CRISPR repeat sequence is a sequence with at least: about 30%, about 40%, about 50%, about 60%, about 65%, about 70%, about 75%, about 80%, about 85%, about 90%, about 95%, or 100% sequence identity to a reference CRISPR repeat sequence (e.g., crRNA from *S. pyogenes*).

A minimum CRISPR repeat comprises nucleotides that can hybridize to a minimum tracrRNA sequence in a cell. The minimum CRISPR repeat and a minimum tracrRNA sequence form a duplex, i.e. a base-paired double-stranded structure. Together, the minimum CRISPR repeat and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence comprises at least: about 30%, about 40%, about 50%, about 60%, about 65%, about 70%, about 75%, about 80%, about 85%, about 90%, about 95%, or 100% complementary to the minimum tracrRNA sequence. In some embodiments, at least a part of the minimum CRISPR repeat sequence comprises at most: about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length of from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, the minimum CRISPR repeat sequence is approximately 9 nucleotides in length. In some embodiments, the minimum CRISPR repeat sequence is approximately 12 nucleotides in length.

In some embodiments, the minimum CRISPR repeat sequence is at least about 60% identical to a reference minimum CRISPR repeat sequence (e.g., wild type crRNA from *S. pyogenes*) over a stretch of at least 6, 7, or 8 contiguous nucleotides. For example, the minimum CRISPR repeat sequence is at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least: about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence comprises nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least: about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length of from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. In some embodiments, the minimum tracrRNA sequence is approximately 9 nucleotides in length. In some embodiments, the minimum tracrRNA sequence is approximately 12 nucleotides. In some embodiments, the minimum tracrRNA consists of tracrRNA nt 23-48 described in Jinek et al., supra.

In some embodiments, the minimum tracrRNA sequence is at least about 60% identical to a reference minimum tracrRNA (e.g., wild type, tracrRNA from *S. pyogenes*) sequence over a stretch of at least: 6, 7, or 8 contiguous nucleotides. For example, the minimum tracrRNA sequence is at least: about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least: 6, 7, or 8 contiguous nucleotides.

In some embodiments, the duplex between the minimum CRISPR RNA and the minimum tracrRNA comprises a double helix. In some embodiments, the duplex between the minimum CRISPR RNA and the minimum tracrRNA comprises at least about: 1, 2, 3, 4, 5, 6, 7, 8, 9, or 10 or more nucleotides. In some embodiments, the duplex between the minimum CRISPR RNA and the minimum tracrRNA comprises at most about: 1, 2, 3, 4, 5, 6, 7, 8, 9, or 10 or more nucleotides.

In some embodiments, the duplex comprises a mismatch (i.e., the two strands of the duplex are not 100% complementary). In some embodiments, the duplex comprises at least about: 1, 2, 3, 4, or 5 or mismatches. In some embodiments, the duplex comprises at most about: 1, 2, 3, 4, or 5 or mismatches. In some embodiments, the duplex comprises no more than 2 mismatches.

In some embodiments, the tracr sequence is further modified to increase activity or specificity. The length of individual features may be altered, such as shortening or lengthening loops, or extending or shortening paired sections, such as the lower stem, bulge, upper stem, nexus, and hairpins. Individual base pairs can be altered or swapped. The RNA sequence can be altered to increase expression, such as by avoiding homolopolymers, such as poly Ts that limit trasncription termination.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge comprises, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge comprises an unpaired purine (e.g., adenine) on the minimum CRISPR repeat strand of the bulge. In some embodiments, a bulge comprises an unpaired 5'-AAGY-3' of the minimum tracrRNA sequence strand of the bulge, where Y comprises a nucleotide that can form a wobble pairing with a nucleotide on the minimum CRISPR repeat strand.

In some embodiments, a bulge on the minimum CRISPR repeat side of the duplex comprises at least: 1, 2, 3, 4, or 5 or more unpaired nucleotides. In some embodiments, a bulge on the minimum CRISPR repeat side of the duplex comprises at most: 1, 2, 3, 4, or 5 or more unpaired nucleotides. In some embodiments, a bulge on the minimum CRISPR repeat side of the duplex comprises 1 unpaired nucleotide.

In some embodiments, a bulge on the minimum tracrRNA sequence side of the duplex comprises at least: 1, 2, 3, 4, 5, 6, 7, 8, 9, or 10 or more unpaired nucleotides. In some embodiments, a bulge on the minimum tracrRNA sequence side of the duplex comprises at most: 1, 2, 3, 4, 5, 6, 7, 8, 9, or 10 or more unpaired nucleotides. In some embodiments, a bulge on a second side of the duplex (e.g., the minimum tracrRNA sequence side of the duplex) comprises 4 unpaired nucleotides.

In some embodiments, a bulge comprises at least one wobble pairing. In some embodiments, a bulge comprises at most one wobble pairing. In some embodiments, a bulge comprises at least one purine nucleotide. In some embodiments, a bulge comprises at least 3 purine nucleotides. In some embodiments, a bulge sequence comprises at least 5 purine nucleotides. In some embodiments, a bulge sequence comprises at least one guanine nucleotide. In some embodiments, a bulge sequence comprises at least one adenine nucleotide.

Hairpins

In various embodiments, one or more hairpins are located 3' to the minimum tracrRNA in the 3' tracrRNA sequence.

In some embodiments, the hairpin starts at least about: 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most about: 1, 2, 3, 4, 5, 6, 7, 8, 9 or 10 or more nucleotides 3' of the last paired nucleotide in the minimum CRISPR repeat and minimum tracrRNA sequence duplex.

In some embodiments, a hairpin comprises at least about: 1, 2, 3, 4, 5, 6, 7, 8, 9, 10, 15, or 20 or more consecutive nucleotides. In some embodiments, a hairpin comprises at most about: 1, 2, 3, 4, 5, 6, 7, 8, 9, 10, 15, or more consecutive nucleotides.

In some embodiments, a hairpin comprises a CC dinucleotide (i.e., two consecutive cytosine nucleotides).

In some embodiments, a hairpin comprises duplexed nucleotides (e.g., nucleotides in a hairpin, hybridized together). For example, a hairpin comprises a CC dinucleotide that is hybridized to a GG dinucleotide in a hairpin duplex of the 3' tracrRNA sequence.

One or more of the hairpins can interact with guide RNA-interacting regions of a site-directed polypeptide.

In some embodiments, there are two or more hairpins, and in some embodiments there are three or more hairpins.

3' tracrRNA Sequence

In some embodiments, a 3' tracr RNA sequence comprises a sequence with at least: about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from S. pyogenes).

In some embodiments, the 3' tracrRNA sequence has a length of from about 6 nucleotides to about 100 nucleotides. For example, the 3' tracrRNA sequence can have a length of from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt or from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt. In some embodiments, the 3' tracrRNA sequence has a length of approximately 14 nucleotides.

In some embodiments, the 3' tracrRNA sequence is at least about 60% identical to a reference 3' tracrRNA sequence (e.g., wild type 3' tracrRNA sequence from S. pyogenes) over a stretch of at least: 6, 7, or 8 contiguous nucleotides. For example, the 3' tracrRNA sequence is at least: about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from S. pyogenes) over a stretch of at least 6, 7, or 8 contiguous nucleotides.

In some embodiments, a 3' tracrRNA sequence comprises more than one duplexed region (e.g., hairpin, hybridized region). In some embodiments, a 3' tracrRNA sequence comprises two duplexed regions.

In some embodiments, the 3' tracrRNA sequence comprises a stem loop structure. In some embodiments, a stem loop structure in the 3' tracrRNA) comprises at least: 1, 2, 3, 4, 5, 6, 7, 8, 9, 10, 15 or 20 or more nucleotides. In some embodiments, stem loop structure in the 3' tracrRNA comprises at most: 1, 2, 3, 4, 5, 6, 7, 8, 9 or 10 or more nucleotides. In some embodiments, the stem loop structure comprises a functional moiety. For example, the stem loop structure may comprise an aptamer, a ribozyme, a protein-interacting hairpin, a CRISPR array, an intron, or an exon. In some embodiments, the stem loop structure comprises at least about: 1, 2, 3, 4, or 5 or more functional moieties. In some embodiments, the stem loop structure comprises at most about: 1, 2, 3, 4, or 5 or more functional moieties.

In some embodiments, the hairpin in the 3' tracrRNA sequence comprises a P-domain. In some embodiments, the P-domain comprises a double-stranded region in the hairpin.

tracrRNA Extension Sequence

In some embodiments, a tracrRNA extension sequence can provide stability and/or provide a location for modifications of a nucleic acid-targeting nucleic acid. A tracrRNA extension sequence may be provided whether or not the tracrRNA is joined to the crisprRNA, i.e. in the context of single-molecule guides as well as double-molecule guides. In some embodiments, a tracrRNA extension sequence has a length of from about 1 nucleotide to about 400 nucleotides. In some embodiments, a tracrRNA extension sequence has a length of more than: 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 nucleotides. In some embodiments, a tracrRNA extension sequence has a length from about 20 to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. In some embodiments, a tracrRNA extension sequence can have a length of less than 1000 nucleotides. In some embodiments, a tracrRNA extension sequence comprises less than 10 nucleotides in length. In some embodiments, a tracrRNA extension sequence is 10-30 nucleotides in length. In some embodiments, tracrRNA extension sequence is 30-70 nucleotides in length.

In some embodiments, the tracrRNA extension sequence comprises a functional moiety (e.g., stability control sequence, ribozyme, endoribonuclease binding sequence). In some embodiments, a functional moiety can influence the stability of a nucleic acid targeting RNA. In some embodiments, a functional moiety comprises a transcriptional terminator segment (i.e., a transcription termination sequence). In some embodiments, the functional moiety has a total length of from about 10 nucleotides to about 100 nucleotides, from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nucleotides (nt) to about 80 nt, from about 15 nt to about 50 nt, from about 15 nt to about 40 nt, from about 15 nt to about 30 nt or from about 15 nt to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include: a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability, or any combination thereof. In some embodiments, a tracrRNA extension sequence comprises a primer binding site, a molecular index (e.g., barcode sequence). In some embodiments, the tracrRNA extension sequence comprises one or more affinity tags.

Single-Molecule Guide Linker Sequence

In some embodiments, the linker sequence of a single-molecule guide nucleic acid has a length of from about 3 nucleotides to about 100 nucleotides. In Jinek et al., supra, for example, a simple 4 nucleotide "tetraloop" (-GAAA-) was used, Science, 337(6096):816-821 (2012). An illustrative linker has a length of from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt or from about 3 nt to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a single-molecule guide nucleic acid is between 4 and 40 nucleotides. In some embodiments, a linker is at least about: 100, 500, 1000, 1500, 2000, 2500, 3000, 3500, 4000, 4500, 5000, 5500, 6000, 6500, or 7000 or more nucleotides. In some embodiments, a linker is at most about: 100, 500, 1000, 1500, 2000, 2500, 3000, 3500, 4000, 4500, 5000, 5500, 6000, 6500, or 7000 or more nucleotides.

Linkers can comprise any of a variety of sequences, although preferably the linker will not comprise sequences that have extensive regions of homology with other portions of the guide RNA, which might cause intramolecular binding that could interfere with other functional regions of the guide. In Jinek et al., supra, a simple 4 nucleotide sequence -GAAA- was used, Science, 337(6096):816-821 (2012), but numerous other sequences, including longer sequences can likewise be used.

In some embodiments, the linker sequence comprises a functional moiety. For example, the linker sequence may comprise an aptamer, a ribozyme, a protein-interacting hairpin, a CRISPR array, an intron, and an exon. In some embodiments, the linker sequence comprises at least about: 1, 2, 3, 4, or 5 or more functional moieties. In some embodiments, the linker sequence comprises at most about: 1, 2, 3, 4, or 5 or more functional moieties.

Complexes of a Nucleic Acid-Targeting Nucleic Acid and a Site-Directed Polypeptide A nucleic acid-targeting nucleic acid interacts with a site-directed polypeptide (e.g., a nucleic acid-guided nuclease such as Cas9), thereby forming a complex. The nucleic acid-targeting nucleic acid guides the site-directed polypeptide to a target nucleic acid.

Codon-Optimization

In some embodiments, a polynucleotide encoding a site-directed polypeptide is codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Nucleic Acids Encoding System Components

In another aspect, the present disclosure provides a nucleic acid comprising a nucleotide sequence encoding a nucleic acid-targeting nucleic acid of the disclosure, a site-directed polypeptide of the disclosure, and/or any nucleic acid or proteinaceous molecule necessary to carry out the embodiments of the methods of the disclosure.

In some embodiments, the nucleic acid encoding a nucleic acid-targeting nucleic acid of the disclosure, a site-directed polypeptide of the disclosure, and/or any nucleic acid or proteinaceous molecule necessary to carry out the embodiments of the methods of the disclosure comprises a vector (e.g., a recombinant expression vector).

As used herein, the term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some embodiments, vectors are capable of directing the expression of genes to which they are operatively linked. Such vectors are referred to herein as "recombinant expression vectors", or more simply "expression vectors", which serve equivalent functions.

The term "operably linked" is intended herein to mean that the nucleotide sequence of interest is linked to regulatory sequence(s) in a manner which allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, a retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vector contemplated for eukaryotic target cells include, but are not limited to, the vectors pXT1, pSG5, pSVK3, pBPV, pMSG, and pSVLSV40 (Pharmacia). Other vectors may be used so long as they are compatible with the host cell.

In some embodiments, a vector comprises one or more transcription and/or translation control elements. Depending on the host/vector system utilized, any of a number of suitable transcription and translation control elements, including constitutive and inducible promoters, transcription enhancer elements, transcription terminators, etc. may be used in the expression vector.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK) and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art and additional information and approaches are regularly being described; see, e.g., Ma, H. et al., Molecular Therapy—Nucleic Acids (2014) 3, e161, doi:10.1038/mtna.2014.12.

The expression vector may also contain a ribosome binding site for translation initiation and a transcription terminator. The expression vector may also include appropriate sequences for amplifying expression. The expression vector may also include nucleotide sequences encoding non-native tags (e.g., histidine tag, hemagglutinin tag, green fluorescent protein, etc.) that are fused to the site-directed polypeptide, thus resulting in a fusion protein.

In some embodiments, a promoter is an inducible promoter (e.g., heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.).

In some embodiments, the nucleic acid encoding a nucleic acid-targeting nucleic acid of the disclosure and/or a site-directed polypeptide are packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

Kits

The present disclosure provides kits for carrying out the methods of the disclosure. A kit can include one or more of: a nucleic acid-targeting nucleic acid of the disclosure, a polynucleotide encoding a nucleic acid-targeting nucleic acid, a site-directed polypeptide of the disclosure, a polynucleotide encoding a site-directed polypeptide and/or any nucleic acid or proteinaceous molecule necessary to carry out the embodiments of the methods of the disclosure, or any combination thereof.

In some embodiments, a kit comprises: (1) a vector comprising a nucleotide sequence encoding a nucleic acid-targeting nucleic acid, and (2) a vector comprising a nucleotide sequence encoding the site-directed polypeptide and (3) a reagent for reconstitution and/or dilution of the vectors.

In some embodiments, a kit comprises: (1) a vector comprising (i) a nucleotide sequence encoding a nucleic acid-targeting nucleic acid, and (ii) a nucleotide sequence encoding the site-directed polypeptide and (2) a reagent for reconstitution and/or dilution of the vector.

In some embodiments of any of the above kits, the kit comprises a single-molecule guide nucleic acid-targeting nucleic acid. In some embodiments of any of the above kits, the kit comprises a double-molecule nucleic acid-targeting nucleic acid. In some embodiments of any of the above kits, the kit comprises two or more double-molecule guides or single-molecule guides. In some embodiments, the kits comprise a vector may encode the nucleic acid targeting nucleic acid.

In some embodiments of any of the above kits, the kit can further comprise a polynucleotide to be inserted to effect the desired genetic modification.

Components of a kit may be in separate containers; or combined in a single container.

In some embodiments, a kit described above further comprises one or more additional reagents, where such additional reagents can be selected from: a buffer, a buffer for introducing the a polypeptide or polynucleotide item of the kit into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, or a diluting buffer or the like.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. The instructions may be present in the kits as a package insert, in the labeling of the container of the kit or components thereof (i.e., associated with the packaging or subpackaging) etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this embodiment is a kit that includes a web address where the instructions can be viewed and/or from which the instructions can be downloaded. As with the instructions, this means for obtaining the instructions can be recorded on a suitable substrate.

Guide RNA Formulation

Guide RNAs of the invention are formulated with pharmaceutically acceptable excipients such as carriers, solvents, stabilizers, adjuvants, diluents, etc., depending upon the particular mode of administration and dosage form. Guide RNA compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In some embodiments, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

Genetically Modified Cells

As used herein, the term "genetically modified cell" refers to a cell that comprises at least one genetic modification introduced by genome editing (e.g., using the CRISPR/Cas system). In some embodiments herein, the genetically modified cell is a genetically modified progenitor cell. A genetically modified cell comprising an exogenous nucleic acid-targeting nucleic acid and/or an exogenous nucleic acid encoding a nucleic acid-targeting nucleic acid is contemplated herein.

In connection with de-repressing γ-globin expression, the phrase "increasing γ-globin levels in a cell" or "increased γ-globin expression in a cell" indicates that γ-globin in a cell or population of cells is at least 2% higher in the cell or population of cells subject to genome editing than in a comparable, control population, in which there has been no genome editing. In some embodiments, the increase in γ-globin expression is at least about 2%, at least about 3%, at least about 4%, at least about 5%, at least about 6%, at least about 7%, at least about 8%, at least about 9%, at least about 10%, at least about 11%), at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more than a comparable control treated population. The term "control treated population" is used herein to describe a population of cells that has been treated with identical media, viral induction, nucleic acid sequences, temperature, confluency, flask size, pH, etc., with the exception of the addition of the genome editing components. Any method known in the art can be used to measure an increase in γ-globin expression, for example, Western Blot analysis of γ-globin or quantifying γ-globin mRNA.

The term "isolated cell" as used herein refers to a cell that has been removed from an organism in which it was originally found, or a descendant of such a cell. Optionally the cell has been cultured in vitro, e.g., under defined conditions or in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched. In some embodiments, the isolated population is an isolated population of human hematopoietic progenitor cells, e.g., a substantially pure population of human hematopoietic progenitor cells as compared to a heterogeneous population of cells comprising human hematopoietic progenitor cells and cells from which the human hematopoietic progenitor cells were derived.

The term "substantially enhanced," with respect to a particular cell population, refers to a population of cells in which the occurrence of a particular type of cell is increased relative to preexisting or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating a hemoglobinopathy.

The term "substantially enriched" with respect to a particular cell population, refers to a population of cells that is at least: about 10%, about 20%, about 30%, about 40%, about 50%, about 60%, about 70% or more with respect to the cells making up a total cell population.

The terms "substantially enriched" or "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of hematopoietic progenitor cells, refers to a population of cells that contain fewer than: about 20%, about 15%, about 10%, about 9%, about 8%, about 7%, about 6%, about 5%, about 4%, about 3%, about 2%, about 1%, or less than 1%, of cells that are not hematopoietic progenitor cells as defined by the terms herein.

Pharmaceutically Acceptable Carriers

The methods of administering progenitor cells to a subject contemplated herein involve the use of therapeutic compositions comprising progenitor cells.

Therapeutic compositions contain a physiologically tolerable carrier together with the cell composition and optionally at least one additional bioactive agent as described herein, dissolved or dispersed therein as an active ingredient. In some embodiments, the therapeutic composition is not substantially immunogenic when administered to a mammal or human patient for therapeutic purposes, unless so desired.

In general, the progenitor cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells as described herein using routine experimentation.

A cell composition can also be emulsified or presented as a liposome composition, provided that the emulsification procedure does not adversely affect cell viability. The cells and any other active ingredient can be mixed with excipients which are pharmaceutically acceptable and compatible with the active ingredient and in amounts suitable for use in the therapeutic methods described herein.

Additional agents included in a cell composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions as described herein that is effective in the treatment of a particular disorder or condition will depend on the nature of the disorder or condition, and can be determined by standard clinical techniques.

Administration & Efficacy

As used herein, the terms "administering," "introducing" and "transplanting" are used interchangeably in the context of the placement of cells, e.g., progenitor cells, as described herein into a subject, by a method or route which results in at least partial localization of the introduced cells at a desired site, such as a site of injury or repair, such that a desired effect(s) is produced. The cells e.g., progenitor cells, or their differentiated progeny can be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of the aspects described herein, an effective amount of hematopoietic progenitor cells is administered via a systemic route of administration, such as an intraperitoneal or intravenous route.

The terms "individual", "subject," "host" and "patient" are used interchangeably herein and refer to any subject for whom diagnosis, treatment or therapy is desired. In some embodiments, the subject is a mammal. In some embodiments, the subject is a human being.

When provided prophylactically, progenitor cells described herein can be administered to a subject in advance of any symptom of a hemoglobinopathy, e.g., prior to initiation of the switch from fetal γ-globin to predominantly β-globin and/or prior to the development of significant anemia or other symptom associated with the hemoglobinopathy. Accordingly, the prophylactic administration of a hematopoietic progenitor cell population serves to prevent a hemoglobinopathy, as disclosed herein.

When provided therapeutically, hematopoietic progenitor cells are provided at (or after) the onset of a symptom or indication of a hemoglobinopathy, e.g., upon the onset of sickle cell anemia or other SCD.

In some embodiments of the aspects described herein, the hematopoietic progenitor cell population being administered according to the methods described herein can be allogeneic hematopoietic progenitor cells obtained from one or more donors. As used herein, "allogeneic" refers to a hematopoietic progenitor cell or biological samples comprising hematopoietic progenitor cells obtained from one or more different donors of the same species, where the genes at one or more loci are not identical. For example, a hematopoietic progenitor cell population being administered to a subject can be derived from umbilical cord blood obtained from one more unrelated donor subjects, or from one or more non-identical siblings. In some embodiments, syngeneic hematopoietic progenitor cell populations can be used, such as those obtained from genetically identical animals, or from identical twins. In other embodiments of this aspect, the hematopoietic progenitor cells are autologous cells; that is, the hematopoietic progenitor cells are obtained or isolated from a subject and administered to the same subject, i.e., the donor and recipient are the same.

In one embodiment, the term "effective amount" as used herein refers to the amount of a population of progenitor cells or their progeny needed to prevent or alleviate at least one or more sign or symptom of a hemoglobinopathy, and relates to a sufficient amount of a composition to provide the desired effect, e.g., treat a subject having a hemoglobinopathy. The term "therapeutically effective amount" therefore refers to an amount of progenitor cells or a composition comprising progenitor cells that is sufficient to promote a particular effect when administered to a typical subject, such as one who has or is at risk for a hemoglobinopathy. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells, comprises at least $10^2$ progenitor cells, at least $5\times10^2$ progenitor cells, at least $10^3$ progenitor cells, at least $5\times10^3$ progenitor cells, at least $10^4$ progenitor cells, at least $5\times10^4$ progenitor cells, at least $10^5$ progenitor cells, at least $2\times10^5$ progenitor cells, at least $3\times10^5$ progenitor cells, at least $4\times10^5$ progenitor cells, at least $5\times10^5$ progenitor cells, at least $6\times10^5$ progenitor cells, at least $7\times10^5$ progenitor cells, at least $8\times10^5$ progenitor cells, at least $9\times10^5$ progenitor cells, at least $1\times10^6$ progenitor cells, at least $2\times10^6$ progenitor cells, at least $3\times10^6$ progenitor cells, at least $4\times10^6$ progenitor cells, at least $5\times10^6$ progenitor cells, at least $6\times10^6$ progenitor cells, at least $7\times10^6$ progenitor cells, at least $8\times10^6$ progenitor cells, at least $9\times10^6$ progenitor cells, or multiples thereof. The progenitor cells are derived from one or more donors, or are obtained from an autologous source. In some embodiments of the aspects described herein, the progenitor cells are expanded in culture prior to administration to a subject in need thereof.

As discussed above, even modest and incremental increases in the levels of HbF expressed in cells of patients having a hemoglobinopathy can be beneficial for ameliorating one or more symptoms of the disease, for increasing long-term survival, and/or for reducing side effects associated with other treatments. Upon administration of such cells to human patients, the presence of RBCs that are producing increased levels of HbF is beneficial. In some embodiments, effective treatment of a subject gives rise to at least about 9% HbF relative to total Hb in the treated subject. In some embodiments, HbF will be at least about 14% of total Hb. In some embodiments HbF will be at least about 20% to 30% of total Hb. Similarly, the introduction of even relatively limited subpopulations of cells having significantly elevated levels of HbF (referred to as "F-cells") can be beneficial in various patients since in some situations normalized cells will have a selective advantage relative to diseased cells. However, even modest levels of circulating RBCs with elevated levels of HbF can be beneficial for ameliorating one or more aspects of hemoglobinopathy in patients. In some embodiments, about 10%, about 20%, about 30%, about 40%, about 50%, about 60%, about 70%, about 80%, about 90% or more of the RBCs in patients to whom such cells are administered are producing increased levels of HbF as described herein.

As used herein, "administered" refers to the delivery of a progenitor cell composition as described herein into a subject by a method or route which results in at least partial localization of the cell composition at a desired site. A cell composition can be administered by any appropriate route which results in effective treatment in the subject, i.e. administration results in delivery to a desired location in the subject where at least a portion of the composition delivered, i.e. at least $1\times10^4$ cells are delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the route is intravenous. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of progenitor cells other than directly into a target site, tissue, or organ, such that it enters, instead, the subject's circulatory system and, thus, is subject to metabolism and other like processes.

The efficacy of a treatment comprising a composition as described herein for the treatment of a hemoglobinopathy can be determined by the skilled clinician. However, a treatment is considered "effective treatment," as the term is used herein, if any one or all of the signs or symptoms of, as but one example, levels of fetal hemoglobin are altered in a beneficial manner (e.g., increased by at least 10%), other clinically accepted symptoms or markers of disease are improved or ameliorated. Efficacy can also be measured by failure of an individual to worsen as assessed by hospitalization or need for medical interventions (e.g., reduced transfusion dependence, or progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present invention ameliorates one or more symptoms associated with a β-hemoglobinopathy by increasing the amount of fetal hemoglobin in the individual. Symptoms and signs typically associated with a hemoglobinopathy, include for example, anemia, tissue hypoxia, organ dysfunction, abnormal hematocrit values, ineffective erythropoiesis, abnormal reticulocyte (erythrocyte) count, abnormal iron load, the presence of ring sideroblasts, splenomegaly, hepatomegaly, impaired peripheral blood flow, dyspnea, increased hemolysis, jaundice, anemic pain crises, acute chest syndrome, splenic sequestration, priapism, stroke, hand-foot syndrome, and pain such as angina pectoris.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise.

Certain numerical values presented herein are preceded by the term "about." The term "about" is used herein to provide literal support for the numerical value the term "about" precedes, as well as a numerical value that is approximately the numerical value, that is the approximating unrecited numerical value may be a number which, in the context it is presented, is the substantial equivalent of the specifically recited numerical value.

When a range of numerical values is presented herein, it is contemplated that each intervening value between the lower and upper limit of the range, the values that are the upper and lower limits of the range, and all stated values with the range are encompassed within the disclosure. All the possible sub-ranges within the lower and upper limits of the range are also contemplated by the disclosure.

EXAMPLES

The invention will be more fully understood by reference to the following examples, which provide illustrative non-limiting embodiments of the invention.

The examples describe the use of the CRISPR/Cas system as an illustrative genome editing technique to create defined therapeutic genomic deletions or single base substitutions, collectively termed "genomic modifications" herein, in the β-globin gene cluster that lead to the upregulation of the expression of HbF. Exemplary therapeutic modifications are genetically and/or functionally similar or identical to those observed in hematopoietic cells of individuals with hemoglobinopathy such as sickle cell or β-thalassemia in which the modifications de-repress, or lead to the re-expression of, γ-globin and thus fetal hemoglobin. Introduction of the defined therapeutic modifications represents a novel therapeutic strategy for the potential amelioration of hemoglobinopathies as described and illustrated herein.

Example 1

Creation of Deletions Proximal to Chr11:5224779-5237723

In this example, we illustrate use of the methods described herein to generate certain deletions that are proximal to the region Chr11:5224779-5237723. Deletions in this region have been observed in human patients designated as HPFH-5 (or "HPFH Sicilian") described in Camaschella et al., *Haematologica*, 75(Suppl 5):26-30 (1990). The 13 kb deletion variant in the human β-globin locus observed in the human patients was associated with the clinical phenotype of hereditary persistence of fetal hemoglobin (HPFH), in which the presence of fetal hemoglobin can complement the defect in adult hemoglobin synthesis or function, and ameliorate disease, in sickle cell anemia or β-thalassemia.

In this example, we illustrate that the CRISPR/Cas system can be used to create deletions functionally resembling those associated with natural HPFH alleles such as HPFH-5. Guide RNAs were designed to eliminate the pathogenic sickle cell allele by deleting the δ and β globin genes as well as substantial portion of the γ globin gene 3' region. FIG. 1A shows the human globin locus with hollow boxes highlighting the HPFH-5 5' and 3' target sites. The 13 kb deletion starts 3 kb 5' to the ψβ1 gene and ends 1.7 kb 3' to the end of the β gene (690 bp downstream from the β gene polyA signal). See FIG. 1B. In addition, guide RNAs were designed to target sites throughout the 13 kb region in order to determine the therapeutic potential of smaller deletions within this locus.

Experimental Methods
Selection of Target Sites

Regions of the β-globin gene cluster were scanned for target sites, including the 5' and 3' regions associated with hereditary persistence of fetal hemoglobin-5 (HPFH-5). Each area was scanned for protospacer adjacent motifs (PAMs) having the sequence NGG and/or NRG. Guide strands corresponding to the PAMs were identified.

For this illustrative example, candidate guides were screened and selected in a multi-step process that involved both theoretical binding and experimentally assessed activity. By way of illustration, candidate guides having sequences that match a particular on-target site with adjacent PAM can be assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended. Candidates predicted to have relatively lower potential for off-target activity can then be assessed experimentally to measure their on-target activity, and then off-target activities at various sites. Preferred guides have sufficiently high on-target activity to achieve desired levels of gene editing at the selected locaus, and relatively lower off-target activity, to reduce the likelihood of alterations at other chromosomal loci. The ratio of on-target to off-target activity is often referred to as the "specificity" of a guide.

For initial screening of predicted off-target activities, there are a number of bioinformatics tools known and publicly available that can be used to predict the most likely off-target sites; and since binding to target sites in the Crispr Cas9 nuclease system is driven by Watson-Crick base pairing between complementary sequences, the degree of dissimilarity (and therefore reduced potential for off-target binding) is essentially related to primary sequence differences: mismatches and bulges, i.e. bases that are changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr dot bme dot gatech dot edu) compiles such similarities.

The following bioinformatics output summary was obtained for specific guide RNA spacer sequences chosen for use in cells.

|  |  | Candidate Sites | Scoring |
|---|---|---|---|
| HPFH5-5' gRNA target sites | | | |
| GCTGAGTTCTAAAATCATCG (SEQ ID NO: 4) | HPFH5-4 | 55 | 0 |
| GCTAAAATCATCGGGGATTT (SEQ ID NO: 5) | HPFH5-5 | 58 | 2 |
| GTAAAATCATCGGGGATTTT (SEQ ID NO: 6) | HPFH5-6 | 95 | 4 |
| HPFH5-3' gRNA target sites | | | |
| GTGTCTTATTACCCTGTCAT (SEQ ID NO: 15) | HPFH5-15 | 77 | 6 |
| GTTGGGGTGGGCCTATGACA (SEQ ID NO: 19) | HPFH5-19 | 76 | 3 |
| GTTTGGGGTGGGCCTATGAC (SEQ ID NO: 20) | HPFH5-20 | 64 | 1 |

The location of the guide RNA target sites relative to the 5' and 3' target regions for the deletion is shown in FIGS. 1C&D.

CRISPR Cloning

Plasmids expressing the Cas9 protein and guide strand RNA were assembled using a vector that expressed humanized Cas9 from *S. pyogenes* and the single-molecule guide RNA. Complementary oligonucleotides corresponding to the guide strand were obtained (Operon or IDT), kinased, annealed and cloned into the vector. Guide RNAs comprising the following spacer sequences were tested in cells:

```
HPFH5-4:
5'-GCTGAGTTCTAAAATCATCG-3'      (SEQ ID NO: 4)

HPFH5-5:
5'-GCTAAAATCATCGGGGATTT-3'      (SEQ ID NO: 5)

HPFH5-6:
5'-GTAAAATCATCGGGGATTTT-3'      (SEQ ID NO: 6)

HPFH5-15:
5'-GTGTCTTATTACCCTGTCAT-3'      (SEQ ID NO: 15)
```

-continued

HPFH5-19:
5'-GTTGGGGTGGGCCTATGACA-3'      (SEQ ID NO: 19)

HPFH5-20:
5'-GTTTGGGGTGGGCCTATGAC-3'      (SEQ ID NO: 20)

The first three spacer sequences target the 5' boundary of the region to be deleted, and the last three target the 3' boundary of the region to be deleted, as described in FIGS. 1C&D.

Cell Transfection

K-562 cells were cultured in RPMI media supplemented with 10% FBS and 2 mM fresh L-glutamine and passaged as they approached a confluency of 1×10$^5$/ml. An Amaxa Nucleofector 4D was used to transfect 200,000 K-562 cells with 1 μg vector expressing HPFH5 targeting sgRNAs, and 1000 ng of plasmid expressing Cas9 following manufacturer's instructions. The genomic DNA was harvested after 3 days using QuickExtract DNA extraction solution (Epicentre, Madison, WI), as described.

Hek293T cells were seeded 24 hours prior to transfection in 24-well plates at a density of 80,000 cells per well and cultured in DMEM media supplemented with 10% FBS and 2 mM fresh L-glutamine. Cells were transfected with 1000 ng of plasmid expressing Cas9 and gRNA using 2 μl of Lipofectamine 2000 (Life technologies), according to manufacturer's instructions. Genomic DNA was harvested at 72 hours after transfection using QuickExtract DNA Extraction Solution (Epicenter).

On- and Off-Target Mutation Detection by Sequencing

To sequence the on-target sites and putative off-target sites, the appropriate amplification primers were identified and reactions were set up with these primers using the genomic DNA harvested using QuickExtract DNA extraction solution (Epicentre) from treated cells three days post-transfection. The amplification primers contain the gene specific portion flanked by adapters. The forward primer's 5' end includes a modified forward (read1) primer-binding site. The reverse primer's 5' end contains a combined modified reverse (read2) and barcode primer-binding site, in opposite orientation. The individual PCR reactions were validated by separating on agarose gels, then purified and re-amplified. The second round forward primers contain the Illumina P5 sequence, followed by a proportion of the modified forward (read1) primer binding site. The second round reverse primers contain the Illumina P7 sequence (at the 5' end), followed by the 6-base barcode and the combined modified reverse (read2) and barcode primer binding site. The second round amplifications were also checked on agarose gels, then purified, and quantitated using a NanoDrop spectrophotometer. The amplification products were pooled to match concentration and then submitted to the Emory Integrated Genomic core for library prepping and sequencing on an Illumina Miseq machine.

The sequencing reads were sorted by barcode and then aligned to the reference sequences supplied by bioinformatics for each product. Insertion and deletion rates in the aligned sequencing reads were detected in the region of the putative cut sites using software previously described; see, e.g., Lin et al., *Nucleic Acids Res.*, 42: 7473-7485 (2014). The levels of insertions and deletions detected in this window were then compared to the level seen in the same location in genomic DNA isolated from in mock transfected cells to minimize the effects of sequencing artifacts.

Mutation Detection Assays

The on- and off-target cleavage activities of Cas9 and guide RNA combinations were measured using the mutation rates resulting from the imperfect repair of double-strand breaks by NHEJ.

On-target loci were amplified using AccuPrime Taq DNA Polymerase High Fidelity (Life Technologies, Carlsbad, CA) following manufacturer's instructions for 40 cycles (94° C., 30 s; 52-60° C., 30 s; 68° C., 60 s) in 50 μl reactions containing 1 μl of the cell lysate, and 1 μl of each 10 μM amplification primer. T7EI mutation detection assays were performed, as per manufacturers protocol [Reyon et al., *Nat. Biotechnol.*, 30: 460-465 (2012)], with the digestions separated on 2% agarose gels and quantified using ImageJ [Guschin et al., *Methods Mol. Biol.*, 649: 247-256 (2010)]. The assays determine the percentage of insertions/deletions ("indels") in the bulk population of cells.

Detecting Inversions and Deletions by End-Point PCR

All end-point PCR reactions were performed using Accu Prime Taq DNA Polymerase High Fidelity (Life Technologies) following manufacturer's instructions for 40 cycles (94° C., 30 s; 60° C., 30 s; 68° C., 45 s) in a 50 μl reaction containing 1 μl of the cell lysate, and 1 μl of each 10 μM target region amplification primer.

Deletion Quantification Using Drop Digital PCR (ddPCR)

The level of joined chromosomal ends, indicating the intended chromosomal deletions, was quantitated using the BioRad (Hercules, CA) drop digital PCR machine (ddPCR) QX200. The machines allow absolute quantification by breaking individual PCR reactions into 20,000 droplets that are individually tested by end-point PCR using a Cyber green-like reagent and a reader that can effectively differentiate between PCR-positive and PCR-negative droplets. Genomic DNA for ddPCR was extracted from K-562 cells using the QiaAMP DNA mini kit (Qiagen, Valencia, CA). PCR reactions contained 2× ddPCR EvaGreen supermix, 200 ng of genomic DNA, primers, and HindIII (1 U/reaction). Reactions were run for 40 cycles (94° C., 30 s; 55-65° C., 30 s; 72° C., 90 s).

Experimental Data

Figure 2A:
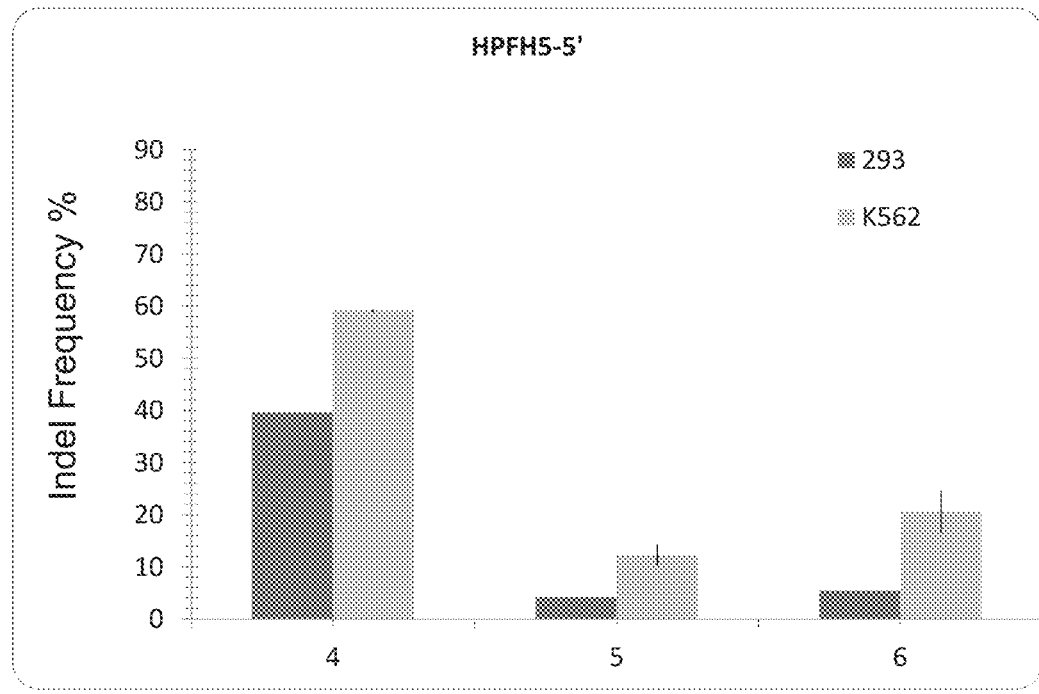
Figure 2B:
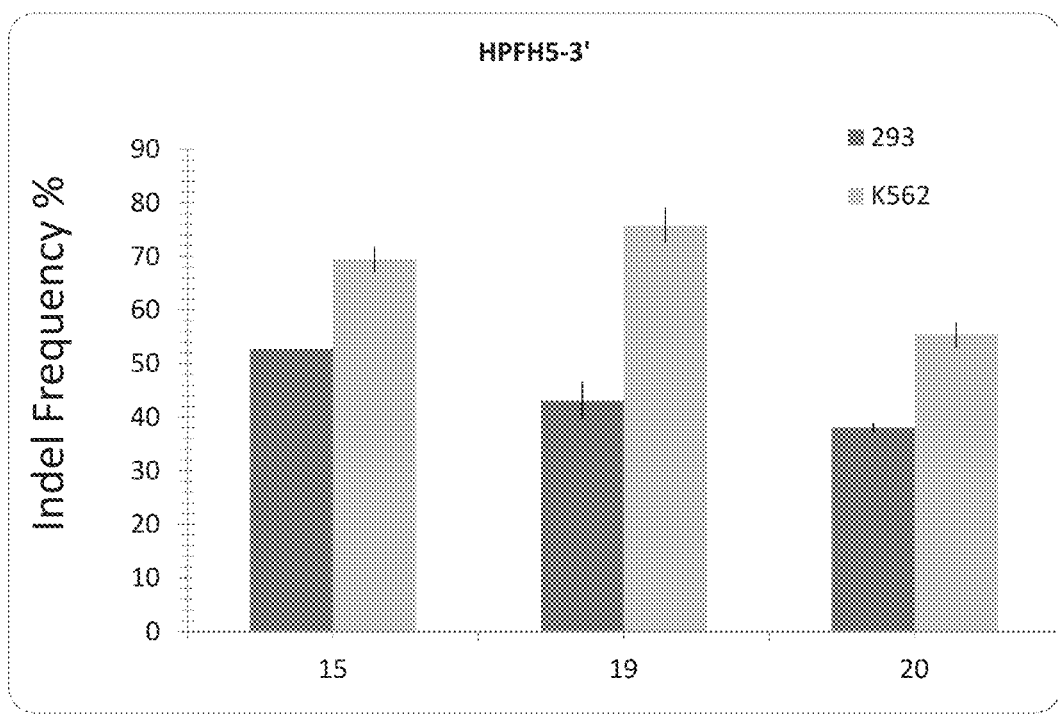

Analysis of the on-target cleavage efficiency with each guide RNA at the 5' and 3' targets sites in both K562 and Hek293 cells is shown in FIGS. 2A&B. All guide RNAs showed activity in both cell types. In K562 cells the highest activity at the 5' and 3' sites was seen with HPFH5-4 (59%) and HPFH5-19 (76%), respectively. Sequence analysis of the indels at the HPFH5-4 site demonstrated a variety of indel mutations consistent with cleavage and NHEJ-mediated mis-repair (FIG. 2C).

Figure 3A:
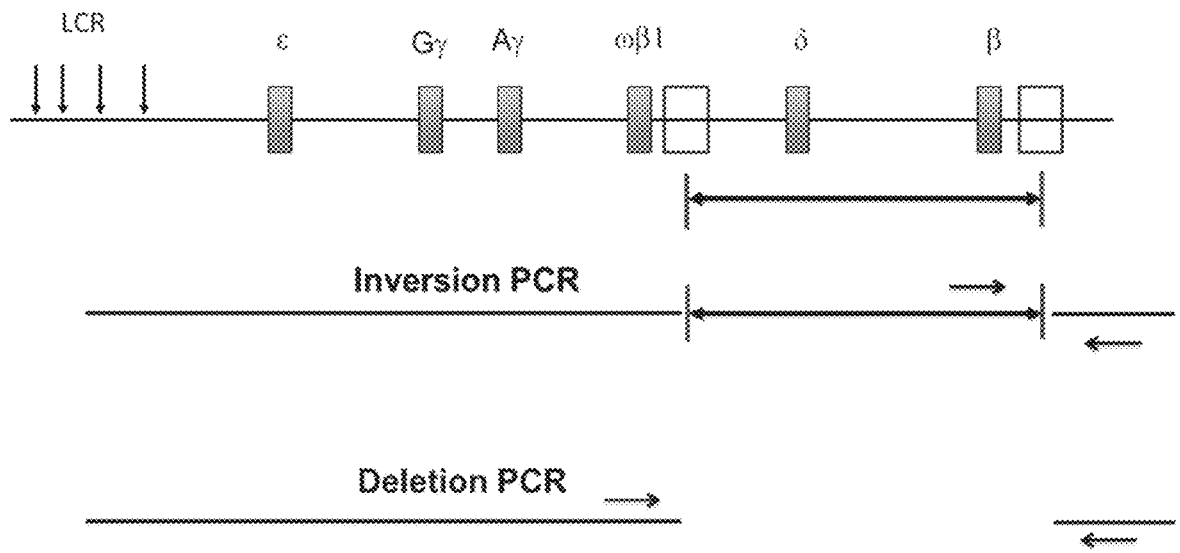
FIGS. 3A-B show results of detecting the outcome of genome editing for pairs of guide RNAs together targeting the 5' and 3' boundaries of the indicated genomic region.
Figure 3B:
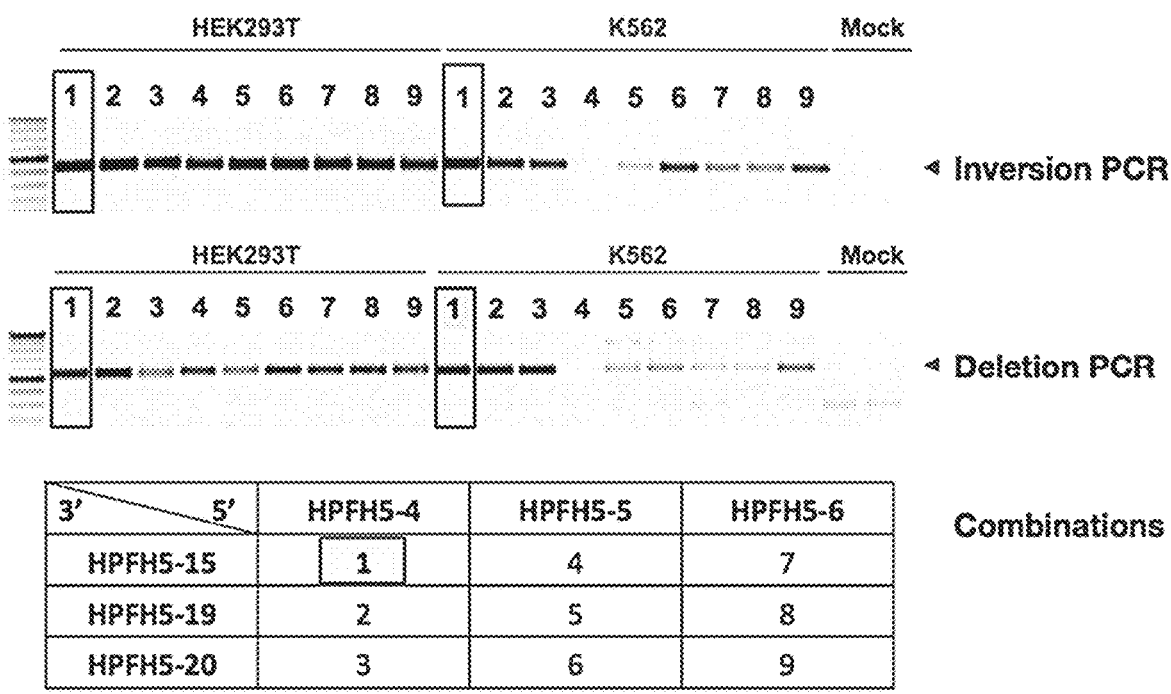

Pairs of guide RNAs from the 5' and 3' target sites were delivered to both K562 and Hek293 cells along with plasmid expressing Cas9, and the genomic DNA was subsequently analyzed by PCR for the presence of deletion or inversion of the 13 kb fragment. FIGS. 3A&B shows that both the deletion and inversion events were detected for all guide RNA combinations. Sequence analysis of the deletion events resulting from the use of the HPFH5-4 and HPFH5-15 guide RNAs confirms the expected 13 kb deletion and shows the prevalent junction sequence created upon joining of the remaining chromosomal ends (FIG. 4).

The efficiency of generating the desired 13 kb deletion allele using different pairs of guide RNAs was quantitated using ddPCR. FIG. 5 shows that the deletion was achieved with all pairs of guides, with a maximum efficiency of ~12% achieved in both cell types by the HPFH5 4-15 guide combination.

The HPFH5-4 and HPFH5-15 guides were examined individually for off-target cleavage activity. Bioinformatics was used to predict the most likely off-target sites (FIG. 6A). The frequency of genome editing at these predicted sites was interrogated using deep sequencing. Data in FIG. 6B showed no evidence of off-target genome modification beyond background for either guide RNA, despite high levels of on-target activity (64% and 91%, respectively). This indicates high specificity for each of these two guide RNAs.

Figure 7B:
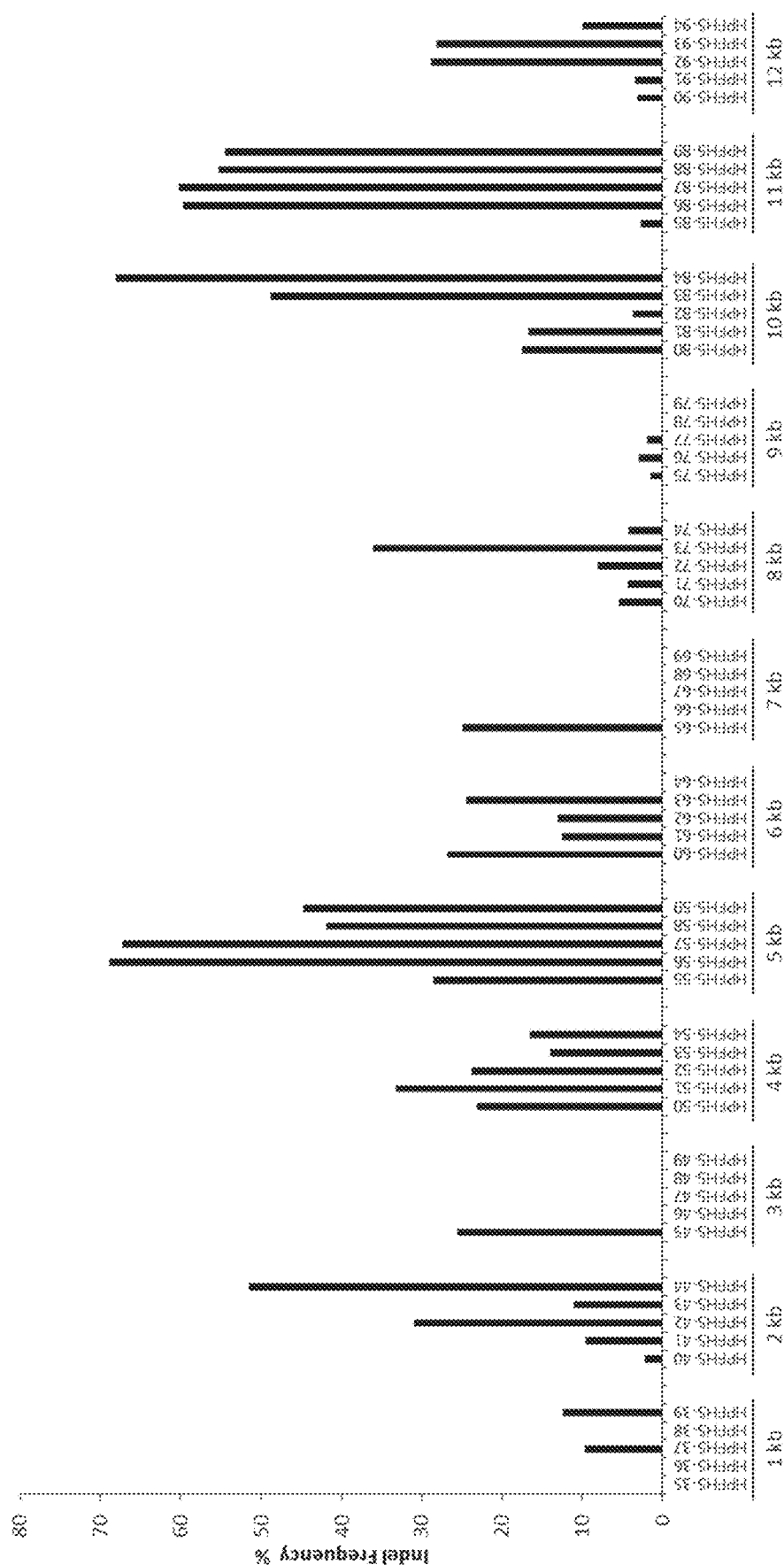

Within the 13 kb HPFH-5 deletion sequence it is possible that smaller subregions are responsible for the phenotype associated with this genomic variant and that deletion of these smaller regions might represent an alternative therapeutic strategy. To test this concept, additional guide RNAs were designed to target sites located throughout the length of the 13 kb sequence (FIG. 7A) and were tested individually for gene editing efficiency. FIG. 7B shows multiple guide RNAs enable high levels of gene editing (up to 70%) at additional regions throughout the 13 kb fragment. It is contemplated that these guides can be paired with each other to create smaller deletions with potential therapeutic utility.

Example 2

Creation of Deletions Proximal to Chr11:5233055-5240389

Figure 8:
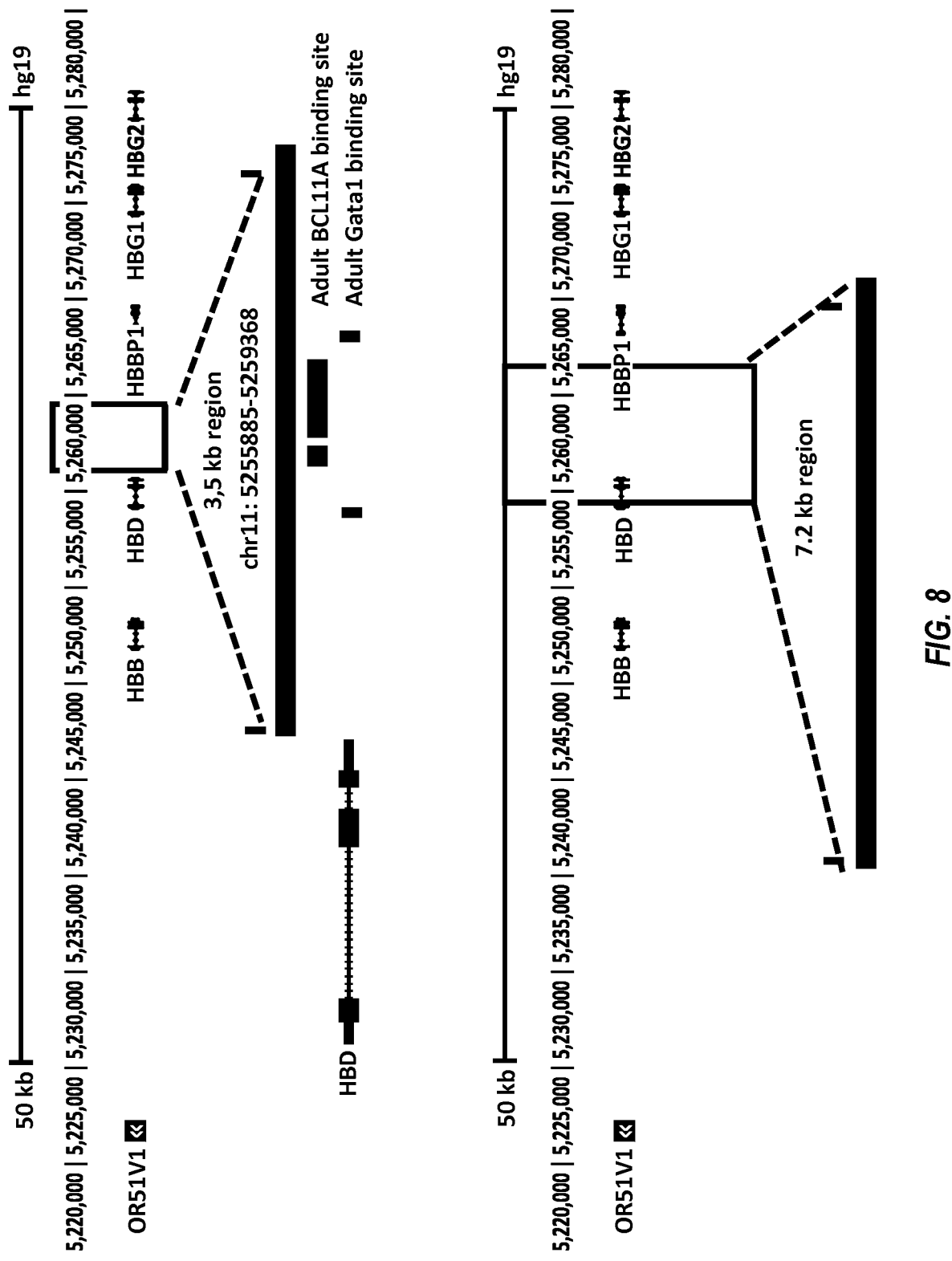
FIG. 8 shows a schematic of the genomic location of HPFH Corfu 3.5 kb (top panel) and 7.2 kb (bottom panel) deletions.

In this example, we illustrate use of the methods described herein to generate certain deletions that are proximal to the region Chr11:5233055-5240389. Deletions in this region have been observed in human patients with a 7.2 kb deletion in the human β-globin locus on chromosome 11 that is referred to herein as the "Corfu long" deletion. In the homozygous state, such a deletion is associated with a complete absence of hemoglobin A and A2 and a high level of fetal hemoglobin and HPFH [Wainscoat et al, *Ann. NY Acad Sci* 445:20 (1985) and Kulozik et al, *Blood* 71:457 (1988)]. This deletion is depicted in FIG. 8. We further determined that known binding sites for key regulators of γ-globin—BCL11a and Gata1—are located within a 3.5 kb subregion within the 7.2 kb region (FIG. 8). It is contemplated that deletion of this smaller region alone (deletion in chromosome 11 within region Chr11:5233055-5240389) might be sufficient to confer an HPFH phenotype comparable to that seen with the larger deletion and, moreover, may be achievable at a higher efficiently of genome editing than for the larger deletion. CRISPR guide RNAs were designed to effect cleavage at each end of the 7.2 kb and 3.5 kb regions and their ability to effect deletion of the intervening fragment was validated.

Figure 10A:
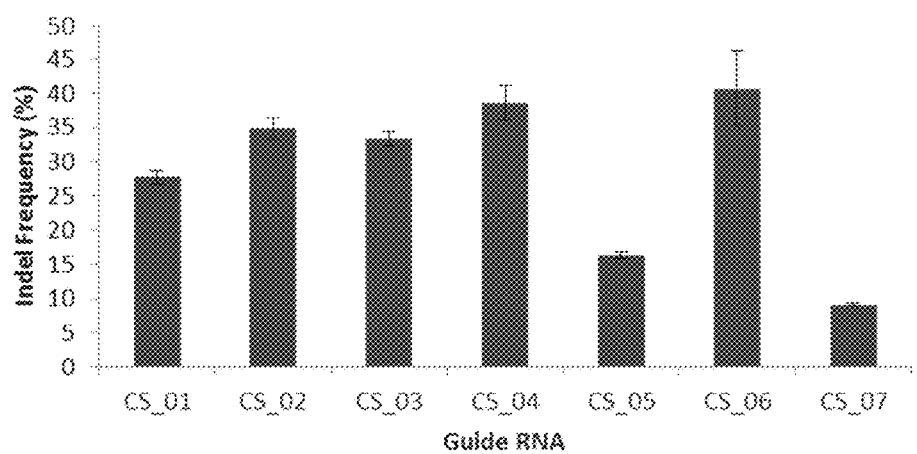
FIGS. 10A-C show the CRISPR-mediated genome modification efficiency of gRNAs targeting the HPFH Corfu locus in Hek293 cells.
Figure 10B:
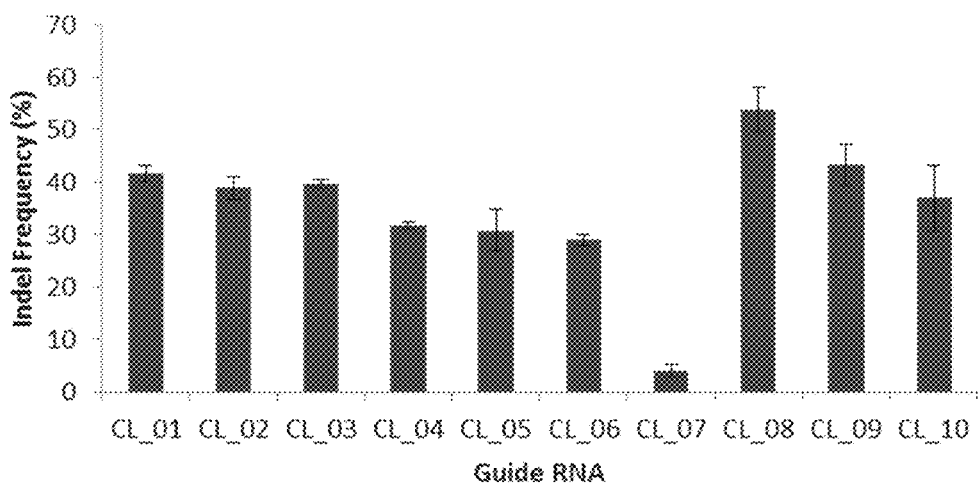
Figure 10C:
Figure 11A:
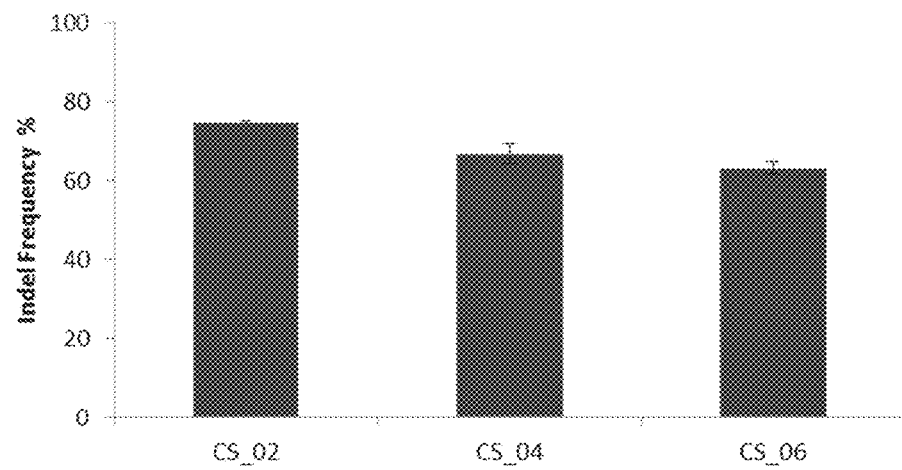
FIGS. 11A-C show the CRISPR-mediated genome modification efficiency of gRNAs targeting the HPFH Corfu locus in K562 cells.
Figure 11B:
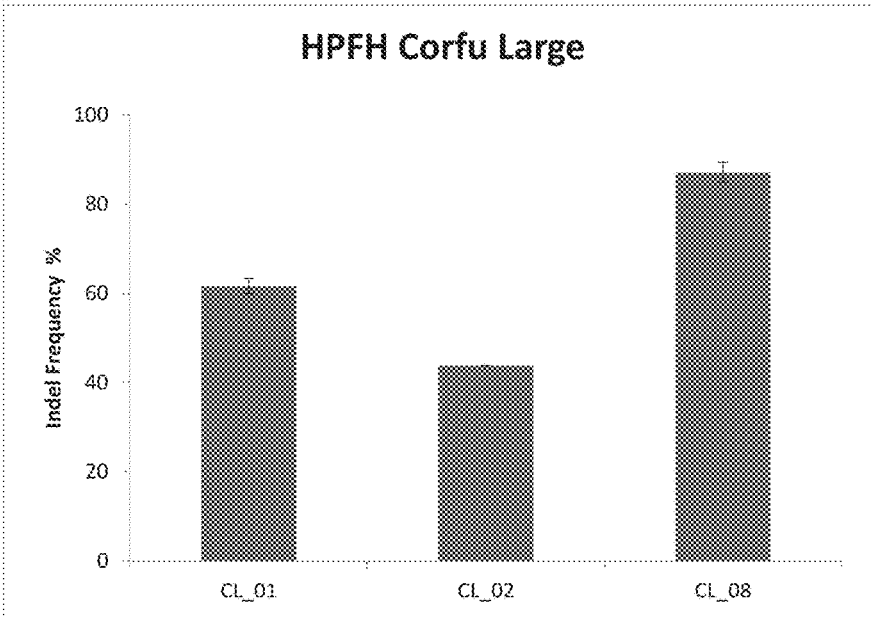
Figure 11C:
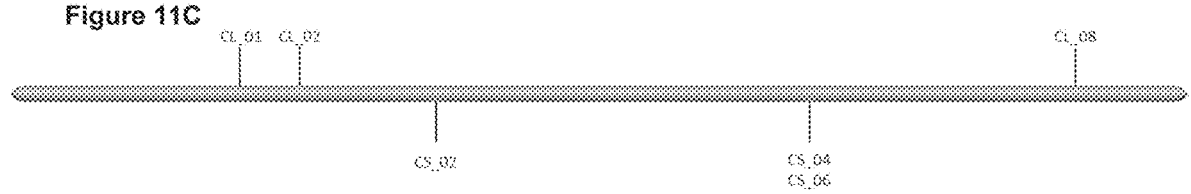
Figures 12A, 12B:
FIGS. 12A-B show the results of detecting genome editing events for pairs of guide RNAs together targeting the 5' and 3' boundaries of the indicated genomic region.

Individual guide RNAs directed towards the boundaries of each of the Corfu deletions were tested for their efficiency of gene editing. The spacer sequences for the guide RNAs are shown in FIG. 9. Vectors encoding the guide RNAs were generated and introduced into cells as described in Example 1. Data in FIGS. 10A-C demonstrate that multiple functional guides were obtained for each boundary that achieve 25-50% genome editing in Hek293 cells. Even higher levels of genome editing activity (40-80%) were seen in K562 cells (FIGS. 11A-C). Co-delivery of pairs of guide RNAs resulted in deletion and inversion of the intervening fragments (FIGS. 12A&B).

Example 3

Creation of Deletions Proximal to Chr11:5226631-5249422

Figures 13A, 13B:
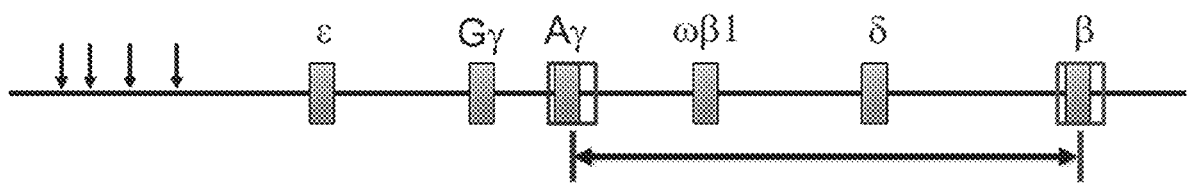
FIGS. 13A-C show the location and activity of the HPFH Kenya deletion guide RNAs in HEK293 cells.

In this example, we illustrate use of the methods described herein to generate certain deletions that are proximal to the region Chr11:5226631-5249422. Deletions in this region have been observed in human patients with a large deletion in the human β-globin locus on chromosome 11 that is referred to herein as the HPFH Kenya-like variant [Huisman et al, *Arch. Biochem. Biophys.* 152:850 (1972) and Ojwang et al, *Hemoglobin* 7:115 (1983)]. The naturally-occurring variant appears to have resulted from non-homologous crossing over between amino acids 80-87 of the $^A\gamma$ and β-globin genes and deletion of the intervening ~23 kb of sequence in chromosome 11 within region Chr11:5226631-5249422. The Kenya fusion protein contains amino acid residues 1-80 of the $^A\gamma$ chain and 87-146 of the β chain. CRISPR guide RNAs used to effect cleavage at each boundary of the ~23 kb region (FIGS. 13A and 1B) were designed and validated. Vectors encoding the guide RNAs were generated and introduced into cells as described in Example 1.

Figure 13C:
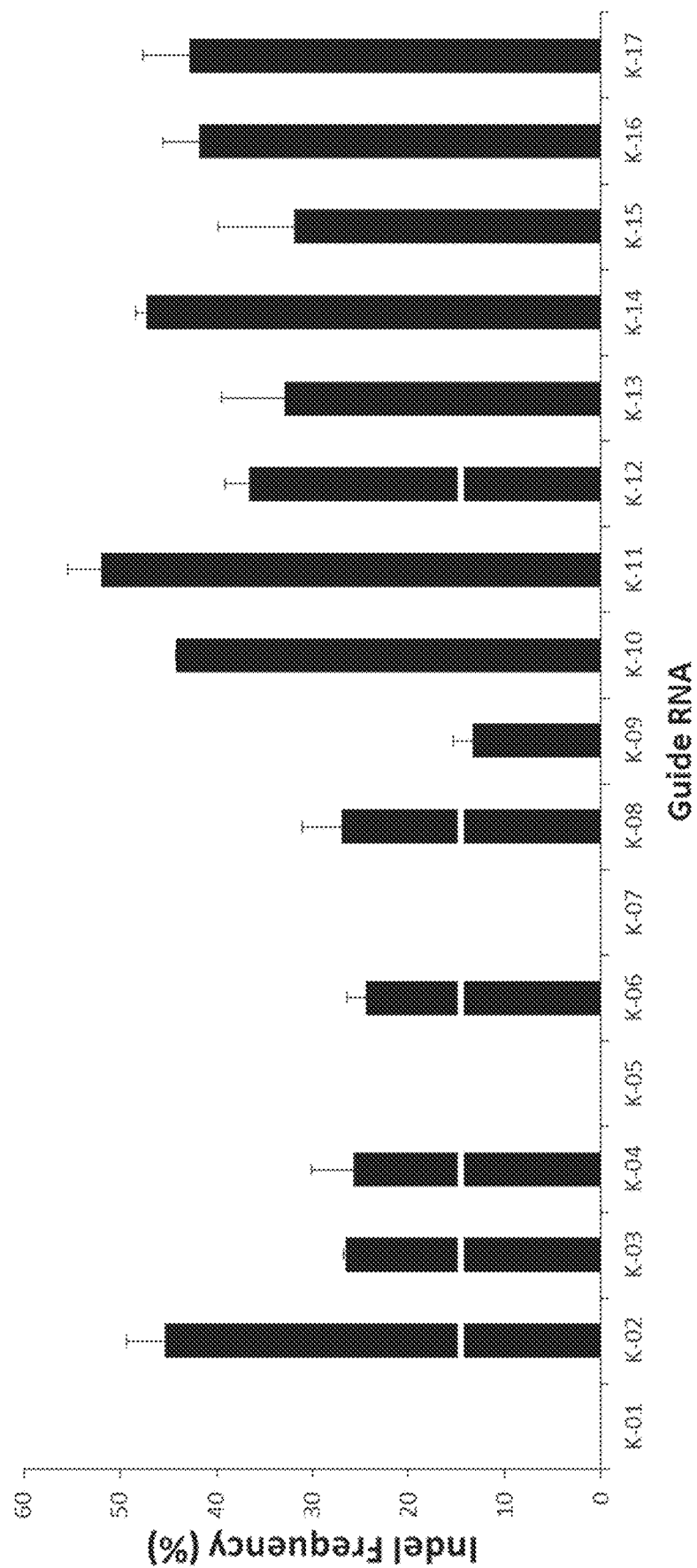

Functional analysis of the guide RNAs demonstrates robust cleavage efficiency is achieved at both the 5' and 3' boundaries of the target locus (FIG. 13C). Combinations of these guides are expected to achieve the desired deletion.

Example 4

Creation of Deletions Proximal to Chr11:5249959-5249971

In this example, we illustrate use of the methods described herein to generate certain deletions that are proximal to the region Chr11:5249959-5249971. Deletions in this region have been observed in human patients with a small deletion variant of the β-globin locus in chromosome 11 within region Chr11:5249959-5249971 that was identified and shown to be associated with HPFH [Gilman et al, *Nucleic acids Research* 16(22):10635 (1988)]. This deletion spans-102 to -114 of the γ-globin gene and encompasses the distal CCAAT box believed important for regulation of the γ-gene promoter (FIG. 14A).

One approach is to cleave this locus within the 13 bp region and allow NHEJ to mis-repair the lesion with the expectation that in some instances the exact 13 bp deletion might be recapitulated. However, the repair outcome by NHEJ alone cannot be assured and it is unlikely that the precise 13 bp deletion will occur at a clinically significant frequency—rather than additional deletions or insertions, which may themselves have the desired therapeutic consequence. Alternatively, the DSB could be repaired by HDR in the presence of a co-delivered repair template donor that specifies the precise 13 bp deletion.

A third approach to creating the 13 bp deletion could be taken that makes use of microhomology at the intended mutation site and the repair pathway of MMEJ. In the present example analysis of the sequence encompassing and adjacent to the 13 bp deletion site revealed the presence of two 8 bp repeat sequences which we predicted would likely recombine during MMEJ-mediated repair to produce the 13 bp deletion in the presence of a single double-strand break (FIG. 14B). We designed guide RNAs to cleave in close proximity to these repeats (FIGS. 14B&C) and tested them in Hek293 cells for their capacity to drive creation of the 13 bp deletion in cells. Vectors encoding the guide RNAs were generated and introduced into cells as described in Example 1.

Figure 15A:
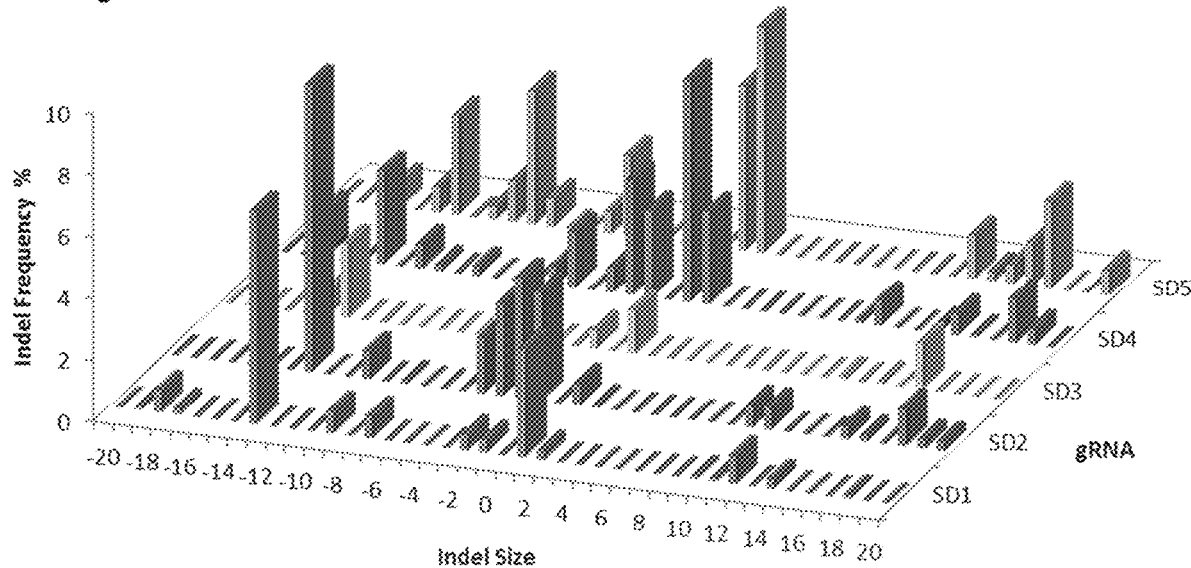
Figure 15B:
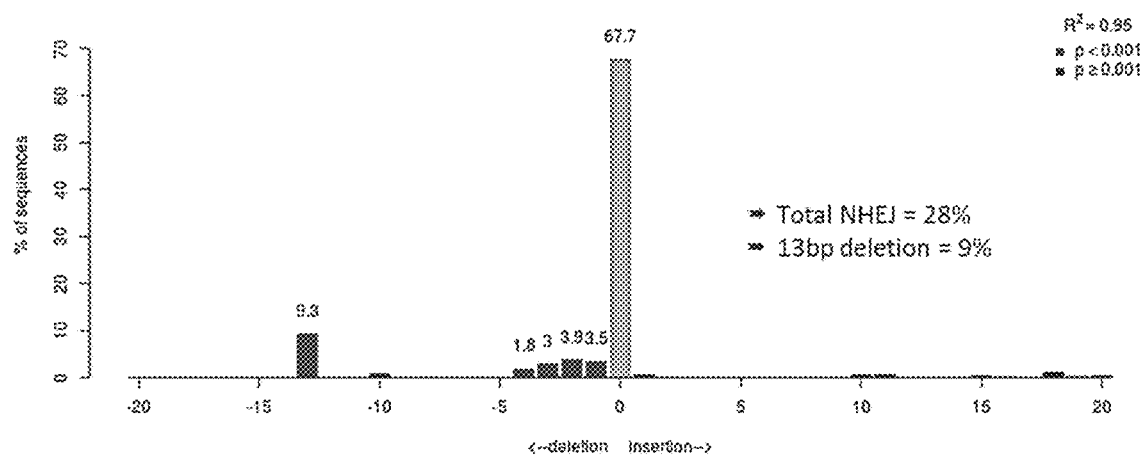

Sequence analysis of the resulting genome editing events revealed that two of the guides, SD1 and SD2, mediated DNA cleavage and repair events for which the 13 bp deletion was the most frequent outcome (FIGS. 15A&B). For the guide SD2, the total allelic frequency of DNA modification was 28%, with a third of these events (9.3% of alleles) being comprised of the 13 bp deletion. The bulk of the remaining modifications were deletions of 1-4 nucleotides, though other events were also detected and sequence-confirmed (FIG. 15C). These data teach that microhomology can be harnessed to enable a single DNA cleavage event to create a therapeutically relevant mutation in the endogenous human β-globin locus.

Example 5

Creation of Deletions Proximal to Chr11:5196709-5239223

In this example, we illustrate use of the methods described herein to generate certain deletions that are proximal to the region Chr11:5196709-5239223. Deletions in this region have been observed in human patients with a large deletion in the human β-globin locus on chromosome 11 that is referred to as the HPFH-4 (or "HPFH Italian") allele [Camaschella et al, *Haematologia* 75(5):26 (1990)] and is characterized by a 40 kb deletion (FIG. 16A) in chromosome 11 within region Chr11:5196709-5239223 that fully encompasses the shorter (13 kb) HPFH-5 allele. It is contemplated that genome editing technologies such as CRISPR can be used to create a targeted deletion of the corresponding or similar genomic region, or subset thereof, in hematopoietic cells of individuals with hemoglobinopathy such as sickle cell or β-thalassemia to de-repress, or lead to the re-expression of, γ-globin and thus fetal hemoglobin.

Example 6

Creation of Deletions Proximal to Chr11:5225700-5236750

In this example, we illustrate use of the methods described herein to generate certain deletions that are proximal to the region Chr11:5225700-5236750. Deletions in this region have been observed in human patients with the HPFH Black allele [Anagnou et al., *Blood* 65:1245 (1985)], which is characterized by a large deletion (FIG. 16B) in chromosome 11 within region Chr11:5225700-5236750 that overlaps completely with the HPFH-4 and HPFH-5 deletions. It is contemplated that genome editing technologies such as CRISPR can be used to create a targeted deletion of the corresponding or similar genomic region, or subset thereof, in hematopoietic cells of individuals with hemoglobinopathy such as sickle cell or β-thalassemia to de-repress, or lead to the re-expression of, γ-globin and thus fetal hemoglobin.

Example 7

Creation of HPFH-Associated Non-Deletion Mutations

The −175 (T to C) point mutation in the $^G\gamma$ or $^A\gamma$ gene of β-globin locus is associated with a phenotype of pancellular HPFH, i.e. across many cells with fairly uniform distribution; see, e.g., Ottolenghi et al., *Blood* 71:815 (1988) and Surrey et al., *Blood* 71:807 (1988). The HPFH phenotype is believed to be due to disruption of one or more cis-elements to which regulatory factors normally bind and repress γ-globin expression, or to enhancement of binding of regulatory factors that upregulate γ-globin expression. It is contemplated that genome editing technologies such as CRISPR can be used to create the point mutation, or other modification resulting in changes in regulatory factor binding, in hematopoietic cells of individuals with hemoglobinopathy such as sickle cell or β-thalassemia to de-repress, or lead to the re-expression of, γ-globin and thus fetal hemoglobin.

Multiple putative PAM sequences for *S. pyogenes* Cas9 are located adjacent to this target site (FIG. 16C).

Example 8

Clinical Studies and Pharmacology

It is well established that an increase in HbF levels reduces HbS polymerization and thereby ameliorates the phenotype of SCA, reducing clinical complications.

In the context of the CRISPR/Cas9 technology, or by using other endonucleases for gene editing as described herein, the main objectives of primary pharmacodynamic studies in human subjects/patients will be to demonstrate successful de-repression of γ-globin and concomitant increases and beneficial effects of HbF, and to determine the safety and efficacy of such genetic modifications for the treatment of hemoglobinopathies.

Cell-based studies can include both wild-type cells, such as normal CD34+ hHSCs, which do not normally express high levels of HbF, but are edited as described herein to increase their levels of HbF; as well as cells such as CD34+ cells that are derived from patients having a hemoglobinopathy such as β-thalassemia or SCD.

Total red cell HbF will be measured by cationic HPLC and the distribution of HbF in red cells will be quantified in F-cells (cells with detectable HbF levels) using FACS. Although even small incremental increases in HbF have been shown to have beneficial effects in the context of SCD, as discussed above, in some embodiments at least about 9% of total Hb in a subject will be HbF, which is associated with decreased mortality in SCD; see, e.g., Platt et al., *N Engl J Med.* 330(23): 1639-1644 (1994). In some embodiments, HbF will be at least about 14%, which is associated with additional clinical benefits, and in some embodiments HbF will be at least about 20% to 30%, which is associated with substantial normalization of phenotype in the context of SCD. Similarly, the introduction of even relatively limited subpopulations of cells having significantly elevated levels of HbF (referred to as "F-cells") can be beneficial in various patients since in some situations normalized cells will have a selective advantage relative to diseased cells. Even modest levels of circulating RBCs with elevated levels of HbF can be beneficial for ameliorating one or more aspects of hemoglobinopathy in patients. However, it is generally contemplated that at least one tenth of circulating red blood cells (RBCs) will have elevated levels of HbF, more than one quarter of circulating RBCs will have elevated levels of HbF, or at least one third of circulating RBCs will have elevated levels of HbF. In some embodiments, at least about one half, and in some embodiments at least about three quarters or more of circulating RBCs will have elevated levels of HbF.

Example 9

Biodistribution

A preliminary feasibility study (non-GLP) will be performed to demonstrate engraftment of CD34+ hHSCs in NOD/SCID IL2Rγ mice. A GLP biodistribution and persistence study will be performed in immune-compromised NOD/SCID IL2Rγ mice. CRISPR/Cas9-modified human CD34+ HSCs will be administered by i.v. injection (or other routes, e.g. intraosseous) to NOD/SCID IL2Rγ mice. Non-modified CD34+ hHSCs will be used as a control.

Example 10

In Vivo Pharmacology Study

In an illustrative example of in vivo pharmacology, gene-edited HSCs are introduced into immunodeficient mice, and results such as HSC engraftment are assessed. For example, "NSG" or NOD scid gamma (NOD.Cg-Prkdcscid 112rgtm1Wjl/SzJ), is a strain of inbred laboratory mice, among the most immunodeficient described to date; see, e.g., Shultz et al., *Nat. Rev. Immunol.* 7(2): 118-130 (2007). Another immune-compromised mouse model applicable for investigating hematopoietic stem cell transplantation is the NOD/MrkBomTac-Prkdc$^{scid}$ mouse (www dot Taconic dot com/NODSC).

One illustrative approach employing an immune-compromised mouse model is to inject CRISPR/Cas9-modified CD34+ human HSCs into immune-compromised NOD/SCID/IL2rγ mice to demonstrate homing and engraftment capabilities.

It is also possible to consider studies in model animals, provided such models are reasonably predictive of one or more aspects of conditions in human patients. Development of animal models providing information relevant to certain aspects of various diseases continues to be the subject of regular improvements in the art, and the use of CRISPR/Cas-9 gene editing is greatly facilitating the more rapid creation of such disease-relevant animal models.

Example 11

Use of Edited Cells for the Amelioration of β-thalassemia

Using the methods described and illustrated herein, human cells expressing increased levels of HbF can be produced. Such cells can include, for example, human hematopoietic stem cells (human HSCs) that are capable of giving rise to cells of the erythroid lineage such as red blood cells (RBCs). Such HSCs can therefore be used to ameliorate one or more synptoms associated with β-thalassemia.

For example, when the genome editing procedure is applied to increase the levels of HbF in cells of a patient suffering from a β-thalassemia, one or more symptoms or complications of the β-thalassemia can be ameliorated, as a result of the combination of two beneficial effects. First, HbF provides a functional form of hemoglobin that can play a significant role in ameliorating the anemia and associated clinical conditions of β-thalassemia (i.e. in β-thalassemia major and β-thalassemia intermedia), in which the adult β-globin chains that would normally be expressed from the HBB gene are absent or reduced. Second, the level of unpaired α-globin chains, which is a cause of a number of other problems associated clinically β-thalassemia, are reduced because the α-globin chains can be paired with β-globin chains encoded by the γ-globin genes, expression of which is increased as described herein.

As also noted herein, β-thalassemia RBCs have selective disadvantages compared to normal RBCs in terms of survival and other factors; and treatment of cells as described herein overcomes certain disadvantages by, e.g., increasing the levels of HbF, and concomitantly decreasing the levels of unpaired α-globin chains.

In addition, other techniques can be applied to enhance the delivery, expansion and/or persistence of cells modified by genome editing as described herein. These include ablation techniques in which some resident cells are eliminated prior to the introduction of cells. Such techniques are routinely used, for example, in the context of bone marrow transplantation and other procedures in which normal or corrected cells are introduced into patients. Numerous such procedures are known in the art and routinely practiced in connection with the treatment of human patients.

One illustrative and nonlimiting example of the use of such techniques for the amelioration of β-thalassemia is as follows.

In an autologous procedure, genome editing is performed on cells derived from a patient with β-thalassemia. Since the patient's own cells are already matched, they do not therefore raise the potential issues associated with use of allogeneic cells. Correction of such cells ex vivo followed by their reintroduction into the patient presents a means of ameliorating the disease.

As one illustrative example of cells that can be used, peripheral blood stem cells (PBSCs) from a patient with β-thalassemia can be derived from the bloodstream. A process called apheresis or leukapheresis can be used to obtain the PBSCs. For 4 or 5 days before apheresis, the patient may be given a medication to increase the number of stem cells released into the bloodstream. In apheresis, blood is removed through a large vein in the arm or a central venous catheter (a flexible tube that is placed in a large vein in the neck, chest, or groin area). The blood goes through a machine that removes stem cells.

As another illustrative example of cells that can be used, hematopoietic stem cells (HSCs) can be harvested from the patient's bone marrow using well known techniques.

CD34 is an antigen associated with hematopoietic stem cells, and isolation of CD34+ HSCs can likewise be accomplished by well-known and clinically-validated methods. For example, a magnetic bead separation process that has been FDA-approved for use in various transplantation contexts and that is available commercially from Miltenyi Biotec, along with preparations for the handling and maintenance of such cells, can be used.

For treating a human patient with β-thalassemia as described herein, a population of CD34+ HSCs adjusted to reflect the patient's weight can be used, e.g. a population comprising about ten million CD34+ HSCs per kilogram of weight. This population of cells is then modified using the genome editing methods described herein. By way of illustration, if Cas9 is the genome editing endonuclease, the protein can be introduced into the CD34+ HSCs by transfection of mRNA using various known techniques; along with the introduction, potentially simultaneously in the transfection, of guide RNAs (which can be single-molecule guides or double-molecule guides) that target loci as described herein. Depending on the procedure used, a portion of the cells (e.g., half the original cells) may then be used for reintroduction into the patient. If ablation is to be used to enhance engraftment of the newly-introduced cells, the patient may be subject to, e.g., mild bone marrow conditioning prior to introduction of the genome edited HSCs. Following any conditioning, the population of genome edited HSCs can be reintroduced into the patient, e.g., by transfusion. Over time, the HSCs give rise to cells of the erythroid lineage, including red blood cells (RBCs).

In the resulting RBCs, genome editing in the case of β-thalassemia results in an increase in the level of HbF, and a concomitant decrease in unpaired α-globin chains; as a result of which one or more symptoms or complications associated with the β-thalassemia are ameliorated.

Example 12

Use of Edited Cells for the Amelioration of Sickle Cell Anemia

Using the methods described and illustrated herein, human cells expressing increased levels of HbF can be produced. Such cells can include, for example, human hematopoietic stem cells (human HSCs) that are capable of giving rise to cells of the erythroid lineage such as red blood cells (RBCs). Such HSCs can therefore be used to ameliorate one or more symptoms associated with Sickle Cell Disease, such as Sickle Cell Anemia.

For example, when the genome editing procedure is applied to increase the levels of HbF in cells of a patient suffering from a Sickle Cell Anemia (SCA), one or more symptoms or complications of SCA can be ameliorated. In certain embodiments, at least one copy of the mutant β-globin gene is knocked down or eliminated, resulting in combination of two beneficial effects. First, HbF provides a functional form of hemoglobin that can play a significant role in ameliorating the anemia and associated clinical conditions of SCA. Second, the level of sickle cell hemoglobin (HbS) expressed from the mutant β-globin is reduced or eliminated. The presence of HbS causes a number of the problems associated clinically with SCA, and even modest reductions in the presence of HbS can be used to reduce or essentially prevent sickling, as described herein and in the art.

As also noted herein, sickle cell RBCs have selective disadvantages compared to normal RBCs in terms of survival and other factors; and treatment of cells as described herein overcomes certain disadvantages by, e.g., increasing the levels of HbF, and, in embodiments in which the mutant β-globin gene is knocked down or eliminated, concomitantly decreasing the levels of HbS.

In addition, other techniques can be applied to enhance the delivery, expansion and/or persistence of cells modified by genome editing as described herein. These include ablation techniques in which some resident cells are eliminated prior to the introduction of cells. Such techniques are routinely used, for example, in the context of bone marrow transplantation and other procedures in which normal or corrected cells are introduced into patients. Numerous such procedures are known in the art and routinely practiced in connection with the treatment of human patients.

One illustrative and nonlimiting example of the use of such techniques for the amelioration of SCA is as follows.

In an autologous procedure, genome editing is performed on cells derived from a patient with SCA. Since the patient's own cells are already matched, they do not therefore raise the potential issues associated with use of allogeneic cells. Correction of such cells ex vivo followed by their reintroduction into the patient presents a means of ameliorating the disease.

As one illustrative example of cells that can be used, PBSCs from a patient with SCA can be derived from the bloodstream, or HSCs can be harvested from the patient's bone marrow, each as described above in the preceding example using well-known techniques. CD34+ cells can then be derived, using procedures as described in the preceding example and well-known techniques.

For treating a human patient with SCA as described herein, a population of CD34+ HSCs adjusted to reflect the patient's weight can be used, e.g. a population comprising about ten million CD34+ HSCs per kilogram of weight. This population of cells is then modified using the genome editing methods described herein. By way of illustration, if Cas9 is the genome editing endonuclease, the protein can be introduced into the CD34+ HSCs by transfection of mRNA using various known techniques; along with the introduction, potentially simultaneously in the transfection, of guide RNAs (which can be single-molecule guides or double-molecule guides) that target loci as described herein. Depending on the procedure used, a portion of the cells (e.g., half the original cells) may then be used for reintroduction into the patient. If ablation is to be used to enhance engraftment of the newly-introduced cells, the patient may be subject to, e.g., mild bone marrow conditioning prior to introduction of the genome edited HSCs. Following any conditioning, the population of genome edited HSCs can be reintroduced into the patient, e.g., by transfusion. Over time, the HSCs give rise to cells of the erythroid lineage, including red blood cells (RBCs).

In the resulting RBCs, genome editing in the case of SCA results in an increase in the level of HbF, and in embodiments in which the mutant β-globin gene is knocked down or eliminated, concomitantly decreasing the levels of HbS; as a result of which one or more symptoms or complications associated with the β-thalassemia are ameliorated.

Example 13

Use of Modified RNAs

As described herein, modified RNAs can be used to encode one or more elements of a genome editing complex that is used to treat a human genetic disease, including by way of illustration a hemoglobinopathy as described above, as well as other human diseases, which can likewise be treated or ameliorated by genome editing of one or more chromosomal loci. In addition to using genome editing to cause deletions of one or more regions as exemplified in the case of treating various hemoglobinopathies, genome editing can also be used to insert sequences into selected positions in a chromosome, which techniques can make use of, for example, homology directed repair (HDR) to insert a sequence of interest, provided through use of a "donor" polynucleotide, as well as other genome modifications. A number of such genome editing techniques that can be performed using the Crispr-Cas9 system were described, for example, in US20140068797.

As described herein, one or more components of the genome editing complex can be encoded by modified polynucleotides. Such polynucleotides can comprise one or more modifications that are used, for example, to enhance activity, stability or specificity, alter delivery, reduce innate immune responses in host cells, or for other enhancements, as further described herein and known in the art.

By way of nonlimiting example in the context of Crispr-Cas9 genome editing, guide RNAs (either single-molecule guides or double-molecule guides) and/or a DNA or an RNA encoding a Cas endonuclease introduced into a cell can be modified, as described herein. Modifications of guide RNAs can be used, for example, to enhance the formation or stability of the Crispr-Cas genome editing complex; to enhance the initiation, stability or kinetics of interactions between the genome editing complex with the target sequence in the genome (which can be used for example to enhance on-target activity); and/or to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half life in the cell to be increased. Modifications enhancing guide RNA half life can be particularly useful in embodiments in which a Cas endonuclease such as a Cas9 is introduced into the target cell via an RNA that needs to be translated in order to generate Cas9 endonuclease, since increasing the half of guide RNAs introduced at the same time as the RNA encoding the endonuclease can be used to increase the time that the guide RNAs and the encoded Cas endonuclease co-exist in the cell.

Modifications can also or alternatively be used to decrease the likelihood or degree to which RNAs introduced into cells elicit innate immune responses.

One or more types of modifications can also be made to RNAs encoding an endonuclease such as Cas9 that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of Crispr-Cas, for example, one or more types of modifications can be made to guide RNAs (including those exemplified above), and/or one or more types of modifications can be made to RNAs encoding Cas endonuclease (including those exemplified above).

By way of further illustration, guide RNAs used in the Crispr-Cas system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduced the likelihood or degree of innate immune response, and/or enhance other attributes, as described further below and in the art; and new types of modifications are regularly being developed.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation as illustrated in publications by Kormann et al. and Warren et al., and other publications provided in the detailed description herein, particularly in the section entitled "Modified Polynucleotides."

A large variety of such modifications are described herein and in the art, and new modifications are regularly being developed, which can be used in the context of genome editing procedures employing Cas endonuclease, as well as ZFNs, TALENS and other endonucleases. These modifications may be introduced during transcription or synthesis of the RNA or may be incorporated in downstream steps.

Such genome editing materials and methods comprising modified polynucleotides as described and illustrated can be used for ameliorating hemoglobinopathies, as an exemplary human genetic disease illustrated herein, as well as other human genetic diseases.

Note Regarding Illustrative Embodiments

While the present disclosure provides descriptions of various specific embodiments for purpose of illustrating various aspects of the present invention and/or its potential applications, it is understood that variations and modifications will occur to those skilled in the art. Accordingly, the invention or inventions described herein should be understood to be at least as broad as they are claimed, and not as more narrowly defined by particular illustrative embodiments provided herein.

All documents cited in this application are hereby incorporated by reference in their entirety, with particular attention to the disclosure for which they are referred.

I claim:

1. A method of gene editing, the method comprising introducing Cas9 endonuclease, a first guide RNA (gRNA), and a second gRNA into a human cell to effect a pair of double-strand breaks (DSBs) within the δβ-globin region of human chromosome 11, wherein the first gRNA comprises a spacer sequence that hybridizes to the same target sequence of the δβ-globin region of human chromosome 11 as a nucleic acid having the nucleic acid sequence of any one of SEQ ID NO: 1-117 and 129-137, the second gRNA comprises a spacer sequence that hybridizes to the same target sequence of the δβ-globin region of human chromosome 11 as a nucleic acid having the nucleic acid sequence of any one of SEQ ID NO: 1-117 and 129-137, and wherein the first gRNA hybridizes to a different target sequence than the second gRNA.

2. The method of claim 1, wherein the method comprises introducing into the cell one or more polynucleotides encoding the Cas9 endonuclease.

3. The method of claim 1, wherein the method comprises introducing into the cell one or more RNAs encoding the Cas9 endonuclease.

4. The method of claim 3, wherein the one or more RNAs are modified RNAs.

5. The method of claim 1, wherein the first gRNA and/or the second gRNA are single-molecule gRNAs (sgRNAs).

6. The method of claim 1, wherein the human cell is an isolated progenitor cell.

7. The method of claim 6, wherein the isolated progenitor cell is a hematopoietic progenitor cell.

8. The method of claim 7, wherein the hematopoietic progenitor cell is capable of giving rise to cells of the erythroid lineage.

9. The method of claim 1, wherein there is a deletion of the chromosomal DNA between the pair of DSBs within the δβ-globin region of human chromosome 11.

10. The method of claim 1, wherein the human cell is from a patient with a β-hemoglobinopathy which is a sickle cell disease or a β-thalassemia.

11. The method of claim 10, wherein the β-hemoglobinopathy is sickle cell disease.

12. The method of claim 10, wherein the β-hemoglobinopathy is a β-thalassemia.

13. The method of claim 1, wherein:
 (a) the first gRNA comprises a spacer sequence that is complementary to SEQ ID NO: 4 and the second gRNA comprises a spacer sequence that is complementary to SEQ ID NO: 19; or
 (b) the first gRNA comprises a spacer sequence that is complementary to SEQ ID NO: 4 and the second gRNA comprises a spacer sequence that is complementary to SEQ ID NO: 20; or
 (c) the first gRNA comprises a spacer sequence that is complementary to SEQ ID NO: 83 and the second gRNA comprises a spacer sequence that is complementary to SEQ ID NO: 43; or
 (d) the first gRNA comprises a spacer sequence that is complementary to SEQ ID NO: 83 and the second gRNA comprises a spacer sequence that is complementary to SEQ ID NO: 15; or
 (e) the first gRNA comprises a spacer sequence that is complementary to SEQ ID NO: 83 and the second gRNA comprises a spacer sequence that is complementary to SEQ ID NO: 43.

14. The method of claim 1, wherein the first gRNA and/or the second gRNA comprises a spacer sequence that hybridizes to the same target sequence of the δβ-globin region of human chromosome 11 as a nucleic acid having the nucleic acid sequence of any one of SEQ ID NOs: 4, 5, 6, 15, 19, and 20.

* * * * *

SEQUENCE LISTING

<160> NUMBER OF SEQ ID NOS: 192

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcttccattc taacccacat                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtactgagtt ctaaaatcat                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gactgagttc taaaatcatc                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gctgagttct aaaatcatcg                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gctaaaatca tcgggattt                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtaaaatcat cggggatttt                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaaatcatc ggggattttg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggagatttca cattaaatgt                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatgccaatg tgggttagaa                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gattagtgta atgccaatgt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcatttaatg tgaaatctca                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaattagtgt aatgccaatg                                                 20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gggactgaga agaatttgaa                                                20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gctgagaaga atttgaaagg                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gtgtcttatt accctgtcat                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggtcataggc ccaccccaaa                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gggaagtccc attcttcctc                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gatgtttaag attagcattc                                                20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttggggtgg gcctatgaca                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtttggggtg ggcctatgac                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgggacttc catttggggt                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gatgggactt ccatttgggg                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagaatggga cttccatttg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaagaatggg acttccattt                                              20

<210> SEQ ID NO 25
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaagaatgg gacttccatt                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gaaacatcct gaggaagaat                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gtaaacatcc tgaggaagaa                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggctaatctt aaacatcctg                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gtggtatggg aggtatacta                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gatctcgaac tcctaacatc                                                   20

<210> SEQ ID NO 31
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 ggtataccte ccataccatg                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggagtgcaat ggcatgatcc                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gagcattgct atggttgccc                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggaattcacc ccaccagtgc                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gacagaccag cacgttgccc                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcagctcctg ggcaacgtgc                                              20

<210> SEQ ID NO 37
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
gttagcaaaa gggcctagct                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gattattctg agtccaagct                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ggctgctggt ggtctaccct                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggtagaccac cagcagccta                                                    20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gtagaccacc agcagcctaa                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gccaccagca gcctaagggt                                                    20

<210> SEQ ID NO 43
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
gggtgggaaa atagaccaat                                                 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcccaaagtg tgactatcaa                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gcccattgat agtcacactt                                                 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gccaaagtgt gactatcaat                                                 20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gctatcaatg gggtaatcag                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtaatcagt ggtgtcaaat                                                 20

<210> SEQ ID NO 49
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
gacctgtctc aaccctcatc                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gacctgatga gggttgagac                                                   20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gcacacacgc agaaagtgtt                                                   20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gtggttcttc tatggctatc                                                   20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtgcctatgt atgattatag                                                   20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtatcagaat ggccctagtc                                                   20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 55
gatcagaatg gccctagtct                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gtctaagtat acccagacta                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gctctaagta tacccagact                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gctagtctgg gtatacttag                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gttcagtatg tctgaatgaa                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gaaattaaag ccaaatcttg                                              20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ggaattaatt cctcaagatt                                              20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gttaaaacaa agtataggaa                                              20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ggtacatgta caagttatat                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gacacattgt cagtatattc                                              20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gatccttcta attttaccta                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gtgccatagg taaaattaga                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gtgagcacca tttttgccat                                                   20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gatggcaaaa atggtgctca                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gcacccatta atgccttgta                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gaaccgtaca aggcattaat                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaaccgtac aaggcattaa                                                   20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gaaagcaagg gaaccgtaca                                                   20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gtccctatct gtagagcctc                                                   20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gagcctctcc catacccatg                                                   20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctccacatg ggtatgggag                                                   20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gtgtctctcc acatgggtat                                                   20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gttgtctctc cacatgggta                                                   20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gttctaagtg cagaattagc                                                   20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
ggcggtgggg agatatgtag         20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtgctgaaag agatgcggtg         20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gctgctgaaa gagatgcggt         20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gactgctgaa agagatgcgg         20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggtgttttag gctaatatag         20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gtcaaatttt ggtggtgata         20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gtacaatagt ataacccctt         20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gcatttgtgg atactattaa                                            20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gtaatagtat ccacaaatgc                                            20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gatcaagcat ccagcatttg                                            20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gtgtcatttt taacaggtag                                            20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggtaaattct taaggccatg                                            20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ggatcaaata acagtcctca                                            20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtctgttaat tccaaagact                                            20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gctgaaatga ttttacacat                                            20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gaggatgagc cacatggtat                                            20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gatgagccac atggtatggg                                            20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggaggtatac taaggactct                                            20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gtttggggtg ggcctatgac                                            20

-continued

```
<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ggtaggtaga tgctagattc                                                  20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gtcttattca atacctaggt                                                  20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gcaccataag ggacatgata                                                  20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gatgtccctt atggtgcttc                                                  20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcagtagagg tatggtttcc                                                  20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gatctagcat ctacctacct                                                  20

<210> SEQ ID NO 104
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gattactggt ggtctaccct                                               20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtagaccacc agtaatctga                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcctaccctc agattactgg                                               20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtggtatggg aggtatacta                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gatctcgaac tcctaacatc                                               20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggtatacctc ccataccatg                                               20

<210> SEQ ID NO 110
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gctaaaatca tcggggattt                                                     20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ggtgtgctgg cccgcaactt                                                     20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtggggcaga agtcgttgct                                                     20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gctggcccgc aactttggca                                                     20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gaaccgtaca aggcattaat                                                     20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gaaagcaagg gaaccgtaca                                                     20

<210> SEQ ID NO 116
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 116
ggaaccgtac aaggcattaa                                              20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gtcaatggta cttgtgagcc                                              20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gccactcaag agatatggtg                                              20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcaagccccc tgtttggatc                                              20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtgcctacaa gccccctgtt                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gcctcgagac taaaggcaac                                              20

<210> SEQ ID NO 122
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 122
gtcttcagcc tacaacatac                                                 20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gcccttcaag cactagtcac                                                 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggccagtgac tagtgcttga                                                 20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gctcgaggca acttagacaa                                                 20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gccagtgact agtgcttgaa                                                 20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gctcgagact aaaggcaaca                                                 20

<210> SEQ ID NO 128
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 128
gcagtgacta gtgcttgaag                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gttagcaaaa gggcctagct                                              20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gtgcctagta cattactatt                                              20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gacagaccag cacgttgccc                                              20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gtacacatat tgaccaaatc                                              20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gcagctcctg ggcaacgtgc                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 134
gacgaatgat tgcatcagtg                                           20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gattattctg agtccaagct                                           20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggtgtgctgg cccatcactt                                           20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gttaagttca tgtcatagga                                           20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gtttgccttg tcaaggctat                                           20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gttgtcaagg ctattggtca                                           20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gttgaccaat agccttgaca                                           20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gaaggctatt ggtcaaggca                                           20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gctattggtc aaggcaaggc                                           20

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, t, g, unknown or other
<220> FEATURE:
<221> NAME/KEY: misc_feature
<222> LOCATION: (1)..(21)
<223> OTHER INFORMATION: n is a, c, g, or t

<400> SEQUENCE: 143
nnnnnnnnnn nnnnnnnnnn nrg                                       23

<210> SEQ ID NO 144
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
aaaatcgata ctgagttcta aaatcatcgg ggattttggg gactatgtct tacttca      57

<210> SEQ ID NO 145
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
gaaggtaaac cccacccgga tactgtccca ttattctgtc atcactta             48

<210> SEQ ID NO 146
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
aagacatagt ccccaaaatc cccgatgatt ttagaactca gtatcgattt taa        53

<210> SEQ ID NO 147
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
aagacatagt ccccaaaatc cctgatttta gaactcagta tcgattttaa             50

<210> SEQ ID NO 148
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
aagacatagt ccccaaaatc cccgatttta gaactcagta tcgattttaa             50

<210> SEQ ID NO 149
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aagacatagt ccccaaaatc cccgatttta gaactcagta tcgattttaa             50

<210> SEQ ID NO 150
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
aagacatagt ccccaaaatc cccgattaga actcagtatc gattttaa               48

<210> SEQ ID NO 151
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aagacatagt ccccaaaatc cccgtgattt tagaactcag tatcgatttt aa          52

<210> SEQ ID NO 152

```
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tgtgaaatct caaggaagta tgaagtaaga catagtcccc aaaatccccg atcataggcc    60
caccccaaat ggaagtccca ttcttcctca ggat                               94

<210> SEQ ID NO 153
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgtgaaatct caaggaagta tgaagtaaga catagtcccc aaaatccccg atcataggcc    60
caccccaaat ggaagtccca ttcttcctca ggat                               94

<210> SEQ ID NO 154
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
tgtgaaatct caaggaagta tgaagtaaga catagtcccc aaaatccccg atcataggcc    60
caccccaaat ggaagtccca ttcttcctca ggat                               94

<210> SEQ ID NO 155
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tgtgaaatct caaggaagta tgaagtaaga catagtcccc aaaatccccg atcataggcc    60
caccccaaat ggaagtccca ttcttcctca ggat                               94

<210> SEQ ID NO 156
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tgtgaaatct caaggaagta tgaagtaaga catagtcccc aaaatccccg atcataggcc    60
caccccaaat ggaagtccca ttcttcctca ggat                               94

<210> SEQ ID NO 157
<211> LENGTH: 94
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 157
tgtgaaatct caaggaagta tgaagtaaga catagtcccc aaaatcccg atcataggcc      60 caccccaaat ggaagtccca ttcttcctca ggat                                 94

<210> SEQ ID NO 158
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tgtgaaatct caaggaagta tgaagtaaga catagtcccc aaaatcccag acataggccc     60
accccaaatg gaagtcccat tcttcctcag gat                                  93

<210> SEQ ID NO 159
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgtgaaatct caaggaagta tgaagtaaga catagtcccc aataggccca ccccaaatgg     60
aagtcccatt cttcctcagg at                                              82

<210> SEQ ID NO 160
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tgtgaaatct caaggaagta tgaagtaaga catagtcccc aaaatcccg atgcataggc      60 ccaccccaaa tggaagtccc attcttcctc agga                                 94

<210> SEQ ID NO 161
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgtgaaatct caaggaagta tgaagtaaga catagtcccc aaaatcccg attttcatag      60 gcccacccca aatggaagtc ccattcttcc tcag                                 94

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
actgagttct aaaatcatcg ggg                                          23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cctgatctct taaatcatcg tgg                                          23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
ctgtcttatt accctgtcat agg                                          23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
tttgcttatt accctgtcat aag                                          23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
ctgatttata accctgtcat cgg                                          23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
atgtgtcatc accctgtcat cag                                          23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168

```
gtgtcttctt tccctgtcat tgg                                              23
```

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169

```
gtgtcttctt ccctgtcat gag                                               23
```

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170

```
tactcttatt ccctgtcat cag                                               23
```

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171

```
cttttttatt aacctgtcat tgg                                              23
```

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172

```
atgagttatt agcctgtcat tgg                                              23
```

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173

```
cattcttatt acactgtcat cag                                              23
```

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174

```
tagttttatt acactgtcat cag                                              23
```

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
atgtcttgat agcctgtcat aag                                          23

<210> SEQ ID NO 176
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ccttgccttg ac                                                      12

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ccttgccttg accaatagcc t                                            21

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aaggcaaact tgaccaat                                                18

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tgacaaggca aacttgacca at                                           22

<210> SEQ ID NO 180
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gccggcccct ggcctcactg gatactctaa gactattggt caagtttgcc ttgtcaaggc    60
tattggtcaa ggcaaggctg gccaacccat gggtggagtt tagccaggga                                    110

<210> SEQ ID NO 181
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
tccctggcta aactccaccc atgggttggc cagccttgcc ttgaccaata gccttgacaa          60
ggcaaacttg accaatagtc ttagagtatc cagtgaggcc aggggccggc                    110

<210> SEQ ID NO 182
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aagactattg gtcaagtttg ccttgtcaag gctattggtc aaggcaaggc tggccaaccc          60
atgggtggag tttag                                                          75

<210> SEQ ID NO 183
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aagactattg gtcaagtttg cctgggtgga gtttag                                   36

<210> SEQ ID NO 184
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aagactattg gtcaagtttg ccttgatcaa ggcaaggctg gccaacccat gggtggagtt          60
tag                                                                       63

<210> SEQ ID NO 185
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aagactattg gtcaagtttg ccttgtcaag gcaaggctgg ccaacccatg gtggagttt          60 ag                                                                        62

<210> SEQ ID NO 186
<211> LENGTH: 61
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 186
aagactattg gtcaagtttg ccttgtcaag gctagctggc caacccatgg gtggagttta    60
g                                                                    61

<210> SEQ ID NO 187
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aagactattg gtcaagtttg ccttgtcaag gcaaggcaag gctggccaac ccatgggtgg    60
agtttag                                                              67

<210> SEQ ID NO 188
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aagactattg gtcaagtttg ccttgtcaag gcttcaaggc aaggctggcc aacccatggg    60
tggagtttag                                                           70

<210> SEQ ID NO 189
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aagactattg gtcaagtttg ccttgtcaag gctattcaag gcaaggctgg ccaacccatg    60
ggtggagttt ag                                                        72

<210> SEQ ID NO 190
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aagactattg gtcaagtttg ccttgtcaag gctattggca aggcaaggct ggccaaccca    60
tgggtggagt ttag                                                      74

<210> SEQ ID NO 191
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 191
gggggcccct tccccacact atctcaatgc aaatatctgt ctgaaagggt ccctggctaa        60
actccaccca tgggttgg                                                      78

<210> SEQ ID NO 192
<211> LENGTH: 9
<212> TYPE: PRT
<213> ORGANISM: Unknown
<220> FEATURE:
<223> OTHER INFORMATION: Description of Unknown: Homing endonuclease
      sequence

<400> SEQUENCE: 192

Leu Ala Gly Leu Ile Asp Ala Asp Gly
1               5
```